US009911031B2

(12) United States Patent
Whelan et al.

(10) Patent No.: US 9,911,031 B2
(45) Date of Patent: Mar. 6, 2018

(54) OBTAINING METRICS FOR A POSITION USING FRAMES CLASSIFIED BY AN ASSOCIATIVE MEMORY

(71) Applicant: The Boeing Company, Chicago, IL (US)

(72) Inventors: John Desmond Whelan, Burien, WA (US); Glenn Alan Hancock, St. Louis, MO (US)

(73) Assignee: THE BOEING COMPANY, Chicago, IL (US)

( * ) Notice: Subject to any disclaimer, the term of this patent is extended or adjusted under 35 U.S.C. 154(b) by 173 days.

(21) Appl. No.: 14/573,591

(22) Filed: Dec. 17, 2014

(65) Prior Publication Data

US 2016/0070958 A1    Mar. 10, 2016

Related U.S. Application Data

(63) Continuation of application No. 14/478,475, filed on Sep. 5, 2014.

(51) Int. Cl.
*G06T 7/20*    (2017.01)
*G06K 9/62*    (2006.01)
(Continued)

(52) U.S. Cl.
CPC ............ *G06K 9/00335* (2013.01); *A61B 5/11* (2013.01); *A61B 5/1123* (2013.01);
(Continued)

(58) Field of Classification Search
CPC ......... A61B 5/742; A61B 5/11; A61B 5/7275; A61B 5/7282; A61B 5/1114;
(Continued)

(56) References Cited

U.S. PATENT DOCUMENTS 4,144,564 A * 3/1979 Lamb ................ G06F 17/30982
4,149,262 A    4/1979 Lamb et al.
(Continued)

OTHER PUBLICATIONS

Office Action, dated Mar. 10, 2016, regarding U.S. Appl. No. 14/478,475, 14 pages.
(Continued)

*Primary Examiner* — Dismery Mercedes
(74) *Attorney, Agent, or Firm* — Yee & Associates, P.C.

(57) ABSTRACT

A method for identifying a motion of interest of an individual. The method includes receiving input data from a non-invasive motion sensor measuring movements of a person. The method also includes collecting motion sensor data for an interval of time. The illustrative embodiments also provide for analyzing the motion sensor input data using an analysis application having a set of classified pre-determined motions. The analysis application classifies a movement captured during the interval of time as a motion corresponding to particular a pre-determined motion among a plurality of pre-determined motions. Classification is performed based on shared relative values among the motion sensor input data and the particular pre-determined motion. The illustrative embodiments also provide for generating an output that provides a translation of the movement for identification of a predetermined motion of interest that represents an undesirable ergonomic aspect.

16 Claims, 30 Drawing Sheets

(51) Int. Cl.
*A61B 5/11* (2006.01)
*G06K 9/00* (2006.01)
*G06F 3/01* (2006.01)
*G06T 1/60* (2006.01)
*G06F 12/0817* (2016.01)
*A61B 5/00* (2006.01)
*G06T 7/70* (2017.01)

(52) U.S. Cl.
CPC ............ *A61B 5/7275* (2013.01); *G06F 3/017* (2013.01); *G06F 12/082* (2013.01); *G06K 9/00342* (2013.01); *G06K 9/6201* (2013.01); *G06K 9/6267* (2013.01); *G06K 9/6285* (2013.01); *G06T 1/60* (2013.01); *G06T 7/20* (2013.01); *G06T 7/70* (2017.01); *A61B 5/1116* (2013.01); *A61B 2503/20* (2013.01); *G06F 12/0822* (2013.01); *G06T 2207/20081* (2013.01); *G06T 2207/30196* (2013.01)

(58) Field of Classification Search
CPC ... A61B 5/1116; A61B 5/1123; A61B 5/7264; A61B 2503/20; A61B 5/746; A61M 2230/63; G06T 2207/20081; G06T 2207/30196; G06T 7/0012; G06T 7/20; G06T 1/60; G06F 3/013; G06F 19/3487
See application file for complete search history.

(56) References Cited

U.S. PATENT DOCUMENTS

| | | | |
|---|---|---|---|
| 5,014,327 A | 5/1991 | Potter et al. | |
| 7,591,793 B2 * | 9/2009 | Orito | A61B 5/1114 128/923 |
| 7,670,303 B2 * | 3/2010 | Sato | A61B 5/1118 377/24.2 |
| 8,525,687 B2 * | 9/2013 | Tran | G06F 19/3418 340/506 |
| 8,560,267 B2 * | 10/2013 | Jangle | A61B 5/1116 702/141 |
| 8,680,991 B2 | 3/2014 | Tran | |
| 8,914,604 B2 * | 12/2014 | Whelan | G06F 17/30286 711/108 |
| 8,996,332 B2 * | 3/2015 | Kahn | A61B 5/1123 702/141 |
| 9,044,172 B2 * | 6/2015 | Baxi | A61B 5/1116 |
| 9,269,151 B2 * | 2/2016 | Zahand | G06T 7/0046 |
| 9,275,276 B2 * | 3/2016 | Kawaguchi | G06T 7/251 |
| 9,298,269 B2 | 3/2016 | Whelan et al. | |
| 2005/0270163 A1 * | 12/2005 | Littell | A61B 5/103 340/573.7 |
| 2006/0267780 A1 | 11/2006 | Adams | |
| 2007/0229663 A1 * | 10/2007 | Aoto | G06K 9/00335 348/155 |
| 2008/0214360 A1 | 9/2008 | Stirling et al. | |
| 2009/0043230 A1 | 2/2009 | Davis-Havill et al. | |
| 2009/0083207 A1 * | 3/2009 | Aparicio, IV | G06N 3/0445 706/46 |
| 2009/0135009 A1 * | 5/2009 | Little | G06Q 10/00 340/540 |
| 2009/0319221 A1 * | 12/2009 | Kahn | A61B 5/1123 702/141 |
| 2010/0176952 A1 * | 7/2010 | Bajcsy | A61B 5/11 340/573.1 |
| 2010/0217533 A1 * | 8/2010 | Nadkarni | A61B 5/1117 702/19 |
| 2011/0066383 A1 * | 3/2011 | Jangle | A61B 5/1116 702/19 |
| 2011/0246123 A1 | 6/2011 | Dellostritto et al. | |
| 2011/0245688 A1 | 10/2011 | Arora et al. | |
| 2011/0275042 A1 * | 11/2011 | Warman | A61B 5/1114 434/247 |
| 2012/0116548 A1 | 5/2012 | Goree et al. | |
| 2012/0146789 A1 * | 6/2012 | De Luca | G08B 21/12 340/540 |
| 2012/0214594 A1 * | 8/2012 | Kirovski | A63F 13/06 463/36 |
| 2012/0302900 A1 | 11/2012 | Yin et al. | |
| 2013/0110011 A1 * | 5/2013 | McGregor | A61B 5/1118 600/595 |
| 2013/0178960 A1 | 7/2013 | Sheehan et al. | |
| 2013/0278501 A1 * | 10/2013 | Bulzacki | G06F 3/017 345/157 |
| 2014/0368658 A1 | 12/2014 | Costa et al. | |
| 2015/0015399 A1 * | 1/2015 | Gleckler | A61B 5/1116 340/573.7 |
| 2015/0262612 A1 | 9/2015 | Kawahara et al. | |
| 2017/0245806 A1 * | 8/2017 | Elhawary | A61B 5/1116 |

OTHER PUBLICATIONS

Prokopenko et al., "Optimizing Associative Information Transfer Within Content-addressable Memory," International Journal of Unconventional Computation, vol. 3, Issue 3, Special issue: "Towards Theory of Unconventional Computing," 2008, pp. 273-296.

Extended European Search Report, dated Feb. 16, 2016, regarding application No. EP15179309.8, 7 pages.

Final Office Action, dated Jul. 14, 2016, regarding U.S. Appl. No. 14/478,475, 25 pages.

Notice of Allowance, dated Nov. 30, 2016, regarding U.S. Appl. No. 14/478,475, 14 pages.

\* cited by examiner

FIG. 10

ENTITIES LIKE: NEW OBSERVATION — 1000

| SCORE | OUTCOME | COMMON ATTRIBUTES |
|---|---|---|
| 1.00 | reaching | _center_top_fairly_farther_south_fairly_west; _center_middle_fairly_near_south_somewhat_east; _center_middle_moderately_near_south; _center_top_fairly_north; _center_middle_near_south_fairly_west; _center_top_fairly_north; _center_bottom_somewhat_near_north_somewhat_east; _center_top_nearest_south_moderately_east; _center_top_fairly_farther_south_nearest_west; _center_middle_fairly_near_south_somewhat_west; _center_top_moderately_north_fairly_west; _center_top_nearer_south; _center_top_extremely_south_fairly_east; _center_middle_nearer_north_fairly_west; _center_top_somewhat_south; _center_top_fairly_farther_south_somewhat_east; _center_top_fairly_north; _center_top_fairly_far_south_somewhat_east; _center_top_fairly_east; _center_top_fairly_farthest_south_fairly_east; _center_top_extremely_farther_south_moderately_east |

1006 — SCORE
1008 — OUTCOME
1002 — COMMON ATTRIBUTES
1004 — (outcome label)

| SCORE | LABEL | ENTITIES LIKE: NEW OBSERVATION |
|---|---|---|
| | | COMMON ATTRIBUTES <u>2604</u> |
| 1.00 | <u>OVERHEAD</u> <u>2602</u> | _center_top_fairly_farther_south_fairly_west;<br>_center_middle_fairly_near_south_somewhat_east;<br>_center_middle_moderately_near_south; _center_top_fairly_north;<br>_center_middle_near_south_fairly_west; _center_top_fairly_north;<br>_center_bottom_somewhat_near_north_somewhat_east;<br>_center_top_nearest_south_moderately_east;<br>_center_top_fairly_farther_south_nearest_west;<br>_center_middle_fairly_near_south_somewhat_west;<br>_center_top_moderately_north_fairly_west; _center_top_nearer_south;<br>_center_top_extremely_south_fairly_east;<br>_center_middle_nearer_north_fairly_west; _center_top_somewhat_south;<br>_center_top_fairly_farther_south_somewhat_east;<br>_center_top_fairly_far_south_somewhat_east; _center_top_fairly_north;<br>_center_top_fairly_farthest_south_fairly_east;<br>_center_top_extremely_farther_south_moderately_east |

OBTAINING METRICS FOR A POSITION USING FRAMES CLASSIFIED BY AN ASSOCIATIVE MEMORY

This application is a continuation-in-part application of U.S. patent application Ser. No. 14/478,475 filed on Sep. 5, 2014.

BACKGROUND INFORMATION

1. Field

The present disclosure relates to methods and devices for determining which movements, of a person or object, metrics are to be generated.

2. Background

Classification systems receive data, analyze the data, and then assign the data to a known set using a classifier, where one or more elements of the data correspond to one or more elements of the known set. For example, in a human motion detection classification system, sensors may measure actions of a human. These sensors may input their data to a classification system, which then analyze the data to determine which action the data most resembles. Examples of such a classification may be to classify whether the human sits, stands, walks, holds a phone, bends over, or takes some other action. In another example, a classification system could analyze the input from sensors on an aircraft and then classify some aspect of the aircraft's operation, such as whether the aircraft executes a turn or whether flaps have been deployed.

However, in some cases, measuring additional metrics regarding a person may not be desirable. For example, it may not be desirable to track metrics on the motions of a person due to the unnecessary data that is generated. Thus, methods and devices are desirable that are able to determine for which motions, of a person or object, metrics should be obtained.

SUMMARY

The illustrative embodiments provide for a method for identifying a motion of interest of an individual. The method includes collecting, at a computer, motion sensor input data of motions of the individual from a motion sensor for an interval of time. The method further includes analyzing, using the computer, the motion sensor input data using an analysis application having a set of classified predetermined motions of interest. The analysis application classifies a movement captured during the interval of time as a motion corresponding to one of a plurality of pre-determined motions of interest based on shared relative attributes. The method further includes generating an output providing notice of an identified predetermined motion of interest to a monitoring system.

The illustrative embodiments also provide for an apparatus for identifying a motion of interest of an individual. The apparatus includes a motion sensor and a computer in communication with the motion sensor. The computer is configured to collect motion sensor data from the motion sensor on motions of the individual for an interval of time. The apparatus further includes a non-transitory computer readable storage medium storing an analysis application having a set of classified pre-determined motions of interest. The analysis application is further configured such that when executed by the computer, the analysis application classifies a movement of the individual captured during the interval of time as a motion corresponding to one of a plurality of predetermined motions of interest based on shared relative attributes. The analysis application is further configured, when executed, to generate an output providing notice of an identified predetermined motion of interest to a monitoring system.

The illustrative embodiments also provide for a system. The system includes a kinematic measurement device having one or more sensors configured to detect a plurality of physical positions of a part of an object. The system further includes an associative memory, in communication with the kinematic measurement device, and comprising a plurality of data and a plurality of associations among the plurality of data, wherein the plurality of data is collected into associated groups, wherein the associative memory is configured to be queried based on at least indirect relationships among the plurality of data. The system further includes a processor, in communication with the associative memory and the kinematic measurement device, and configured to receive motion input data of the object from the kinematic measurement device, compare, in conjunction with the associative memory, the motion input data to a plurality of pre-determined motions stored in the associative memory, classify the motion input data as a particular motion selected from the plurality of pre-determined motions, and to notify a monitoring system when the particular motion matches one of a subset of the plurality of pre-determined motions.

The illustrative embodiments also provide for a method for identifying a motion of interest of an individual. The method includes receiving input data from a non-invasive motion sensor measuring movements of a person. The method also includes collecting motion sensor data for an interval of time. The illustrative embodiments also provide for analyzing the motion sensor input data using an analysis application having a set of classified pre-determined motions. The analysis application classifies a movement captured during the interval of time as a motion corresponding to particular a pre-determined motion among a plurality of pre-determined motions. Classification is performed based on shared relative values among the motion sensor input data and the particular pre-determined motion. The illustrative embodiments also provide for generating an output that provides a translation of the movement for identification of a predetermined motion of interest that represents an undesirable ergonomic aspect.

The illustrative embodiments also provide for an apparatus for identifying a motion of interest of an individual. The apparatus includes a non-invasive motion sensor and a processor in communication with the motion sensor, being configured to collect motion sensor data of a person for an interval of time. The apparatus includes an associative memory configured to analyze the motion sensor input data, the associative memory storing a set of classified predetermined motions. The associative memory is configured to classify a movement captured during the interval of time as a motion corresponding to a particular pre-determined motion among a plurality of pre-determined motions. Classification is performed by comparing shared relative values among the motion sensor input data and the particular pre-determined motion.

The illustrative embodiments also provide for a method for assisting physical therapy for a motion of interest of an individual. The method includes receiving input data of movements of the individual from a non-invasive motion sensor. The method further includes collecting motion sensor data for an interval of time. The method further includes analyzing the motion sensor data using an analysis application having a set of classified pre-determined motions of interest. The analysis application classifies a movement of the individual captured during the interval of time by comparing the movement to a pre-determined motion of interest among the set of classified pre-determined motions of interest. Classification is performed by comparing shared relative attributes among the movement and a pre-determined motion of interest in the set of classified pre-determined motions of interest. The method further includes determining whether the movement captured during the interval of time corresponds to a predetermined therapeutic movement. The method further includes generating an output indicating whether the individual has correctly performed the predetermined therapeutic motion.

BRIEF DESCRIPTION OF THE DRAWINGS

The novel features believed characteristic of the illustrative embodiments are set forth in the appended claims. The illustrative embodiments, however, as well as a preferred mode of use, further objectives and features thereof, will best be understood by reference to the following detailed description of an illustrative embodiment of the present disclosure when read in conjunction with the accompanying drawings, wherein:

FIG. 10 illustrates an example of an entity comparison with outcomes as a result category, in accordance with an illustrative embodiment;

FIG. 26 illustrates an example of an entity comparison using an associative memory, in accordance with an illustrative embodiment;

DETAILED DESCRIPTION

Figure 1:
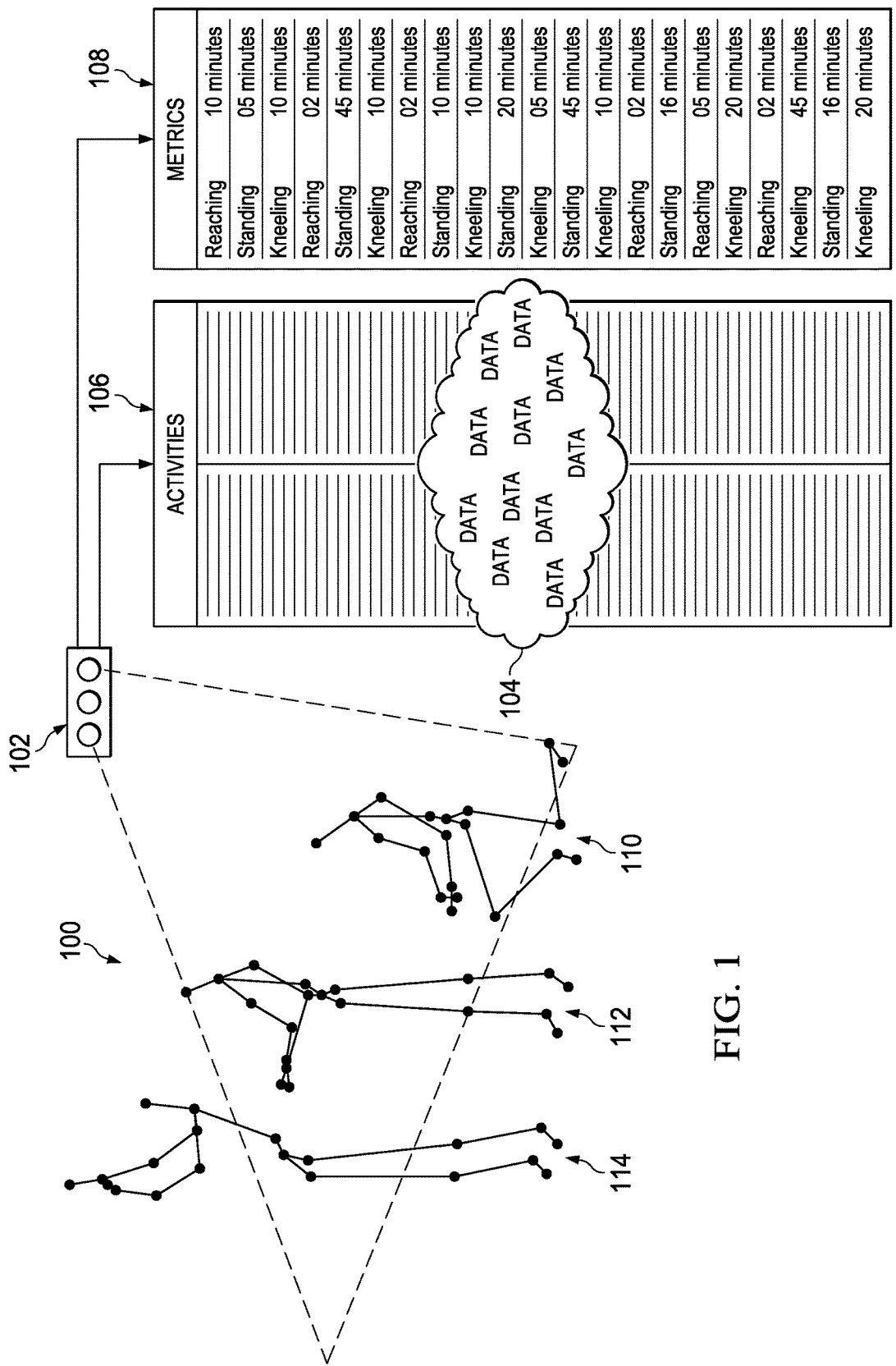
FIG. 1 illustrates one use of a kinematic detection system, in accordance with an illustrative embodiment.

The illustrative embodiments recognize and take into account that obtaining accurate measurements or metrics regarding a particular position of a person is often difficult to gather without having someone physically present to watch. For example, it may be desirable to identify how long an individual maintains an awkward position in order to educate the individual to minimize the potential harm which could occur while the person is in that position. Moreover, many positions can cause harm if done repeatedly or incorrectly. The possibility of undesirable results for poor posture may increase within manufacturing facilities, where employees are asked to bend, reach, and extend when installing equipment and parts. One goal of the illustrative embodiments is to help us understand how long employees are in these kinds of positions, in hopes of educating employees as to undesirable physical behaviors of which they may not be conscious.

The illustrative embodiments also recognize that certain body positions may be hard to identify, due to their nature. Such body positions may be difficult to measure. The illustrative embodiments can single out difficult to measure positions to monitor. The illustrative embodiments may accomplish this goal by capturing difficult to describe behaviors by having a person demonstrate such behaviors and their positions captured. Demonstrated behaviors are used to train a classification system. Thus, a detailed mathematical description of the position may be avoided. This function is described further below.

In the past, monitoring a person's body position in a manufacturing setting involves having someone watch another person as they perform a particular activity. Typically, the observer's role is to collect metrics concerning a certain position as an activity is performed. An example of these metrics is how long a person is in a given type of body position.

This solution does not work very well. First, additional manpower is required to observe, possibly an undesirable amount of additional manpower. Second, because the person being observed often knows they're being observed, the person tends not to carry out the activity in the same manner as if they were alone. Additionally, a human observer is prone to error when observing for long periods of time. Yet further, a human observer may have a cognitive bias which may distort the collected metrics.

Another past monitoring technique was to monitor activities through the use of video cameras. However, this solution still required a human monitor and tended to be less personal than having someone physically present. While cameras can capture a lot of information with regards to specific positions, there still needs to be someone on the other end of the camera to interpret the results. Furthermore, in many situations, the use of video cameras is discouraged or not allowed. Still further, people do not like video cameras watching them, while in the workplace.

The illustrative embodiments recognize these past disadvantages and provide methods and devices for overcoming these disadvantages. Specifically, the illustrative embodiments monitor activities with a motion sensing input device, as opposed to a camera, though the illustrative embodiments could be implemented using a camera if desired. As used herein, a motion sensing input device is an apparatus used to detect the change in position of an object relative to its surroundings or the change in the surroundings relative to an object.

At desired intervals, the motion sensing input device may record a frame or frames of an individual in a certain position and then feeds that information into an associative memory in order to classify the position against previously recorded activities. While the term "associative memory" is defined more formally below, in the context of data processing system 1500 of FIG. 15, briefly an associative memory is a device in which information is collected into associated groups in the interest of gaining new insight based on relationships rather than direct correlation. "Classification" is the task of identifying to which of a set of categories a new observation belongs, on the basis of a training set of data containing observations (or instances) whose category membership is already known. The illustrative embodiments use this information to provide metrics concerning the monitored physical activity of willing users.

One novel aspect of the illustrative embodiments is the ability to use frames collected from a motion sensing input device to detect what position a person is in and determine if metrics for that position should be gathered. After the frames are captured, the illustrative embodiments use an associative memory classification in order to match the frames with a pre-recorded activity. If the classification matches a one of a specific set of positions, metrics pertaining to that position may be generated. Otherwise, monitoring may continue without generating metrics, thereby saving time and data resources.

Thus, the illustrative embodiments use frames, coupled with an associative memory, to identify a particular position and accurately measure it by means of classifying it with pre-recorded activities. The illustrative embodiments do not perform a direct match of a mathematically described position, but instead attempts to match a position's attributes.

Stated differently, a novel aspect of the illustrative embodiments is the ability to interpret a person's position and determine if that position is one that should be measured based on activities previously identified by the user. This ability allows for the quantification of activities which might otherwise be difficult to measure or capture.

The illustrative embodiments have other advantages. For example, the illustrative embodiments may operate in an unobtrusive fashion, being nearly invisible to the participant being observed. While the user should be informed of the observation ahead of time, the operation of the illustrative embodiments may feel less invasive. In another example, the illustrative embodiments make use of inexpensive hardware and centralized software. In another example, the illustrative embodiments are flexible because the illustrative embodiments can function in many situations without being programmed. In another example, the distinctions the illustrative embodiments use to measure different activities can be updated, changed, or improved as needed, possibly in real time. In another example, once configured, no human intervention is needed. The illustrative embodiments may be completely automated.

In another example, the illustrative embodiments are not limited to just monitoring human movement, but could be applied to other non-human movements as well. For example, the illustrative embodiments could be used to track animal movements or the movement of robots, assuming these movements can be detected by an input device.

The illustrative embodiments have the ability to learn by improving its classifications. The illustrative embodiments may replace older and more-cumbersome techniques of monitoring activities. The illustrative embodiments are subject matter independent and universally deployable.

The illustrative embodiments describe a novel application of a motion sensing input device using an associative memory classification rather than the basic licensed core technologies that one uses to accomplish these processes. The illustrative embodiments include the ability to classify an observation, using an example of an associative memory classification. However, the illustrative embodiments could be accomplished with any sort of classification mechanism and is not limited to only the use of an associative memory.

The illustrative embodiments include the ability to detect movements by using an interface to a motion sensing input device. This interface can vary in scope and functionality, but preserves the job of defining the coordinates of a movement in whatever capacity the motion sensing input device can handle.

The illustrative embodiments do not limit what type of activity or position the invention can monitor. The illustrative embodiments do not limit what type of metrics the invention can collect with concerns to said activity or position. The illustrative embodiments do not limit the number of people the invention can monitor with concerns to said activity or position. The illustrative embodiments do not define time constraints on the interval cycle during the monitoring phase.

FIG. 1 illustrates one use of a kinematic detection system, in accordance with an illustrative embodiment. The use of kinematic detection system 102 shown in FIG. 1 does not necessarily limit the claimed inventions, but rather only shows one possible use of the illustrative embodiments. Additional uses for the illustrative embodiments are described below.

In brief summary, the illustrative embodiments monitor activities of one or more individuals 100 with kinematic detection system 102 (which may also be characterized as a motion sensing input device). At set intervals, kinematic detection system 102 records a frame or frames of one or more individuals 100 in certain positions and then feeds that information into associative memory 104 in order to classify that information against previously recorded activities 106. The illustrative embodiments use this information to provide metrics concerning certain activities that are desired to be monitored. In an illustrative embodiment, metrics 108 will be taken only for only certain activities that are considered desirable to monitor.

In more detail, the exemplary use illustrated in FIG. 1 includes using data collected from kinematic detection system 102 to track movements or measured positions of one or more individuals 100. One or more individuals 100 could be a single individual demonstrating multiple positions over time, or could be multiple people in multiple different positions (each of whom is tracked).

The measured positions are fed into associative memory 104 using semantics that associative memory 104 best understands. Thus, for example, kinematic detection system 102 might not send mathematical position data to associative memory 104, but instead send qualitative descriptions of relative positions to associative memory 104. In a more specific example, kinematic detection system 102 could send input that describes the position of the right knee of a person as "somewhat_below_hip." Associative memory 104 can then take this and other qualitative descriptors and compare them to training data, as described further below, to classify the person as kneeling. An example of kneeling is demonstrated by person 110 in FIG. 1. In turn, person 112 demonstrates standing and person 114 demonstrates reaching. In alternative illustrative embodiments, some other intervening hardware or software, or the associative memory itself, could obtain mathematical position or coordinate data from kinematic detection system 102 and translate such data into qualitative descriptors as described above.

In order to reduce processing and data storage requirements, or simply to reduce the amount of reports generated, it may be desirable that only certain positions or movements be monitored. Thus, the illustrative embodiments may be triggered to take metrics 108 on a specific set of positions or movements for which metrics may be desired. Metrics 108 may be, for example, an amount of time a person spends in a particular position, a total amount of time over the course of work day a person spends in a particular person, the longest time spent in a particular position, an average time spent in a particular position, or any other desirable metrics.

For example, without necessarily limiting the claimed inventions, the illustrative embodiments may be used to determine whether a detected movement refers to texting, talking on the phone, walking, bending over, stretching, using a handrail, or any other particular physical activity. The set of possible outcomes may be "texting, talking on the phone, walking, or using a handrail." A determination is made whether the detected movement refers to one member of this set. This determination may be made using an associative memory on the basis of a training set of data containing observations or instances whose category membership is known. In other words, the associative memory has been trained to recognize a particular set of input data as being associated with "texting" or some other position, motion, or activity.

In an illustrative embodiment, metrics 108 are only desired for the activity of "kneeling." So long as the classified position is "kneeling", metrics 108 may then be taken regarding the person's motions over time. Otherwise, metrics 108 are not taken. Alternatively, it may be desirable to take metrics 108 for three activities: standing, kneeling, and reaching, but not for other activities. Again, metrics 108 may be, for example, an amount of time a person spends in a particular position, a total amount of time over the course of a work day a person spends in a particular position, the longest time spent in a particular position, an average time spent in a particular position, or any other desirable metrics.

Turning to the devices used in the illustrative embodiments, kinematic detection system 102 may be any apparatus used to detect changes in position of an object relative to its surroundings or the change in the surroundings relative to an object. In a specific example, which does not necessarily limit the claims, kinematic detection system 102 may be a product that is commercially available off the shelf. Kinematic detection system 102 may be normally used for playing video games, such as in FIG. 3 for example. However, kinematic detection system 102 may be an accelerometer, a camera system, or any other suitable technology for detecting the movement of one or more persons or objects in an area. Thus, for example, kinematic detection system 102 may be used to track positions of a robot. In this case, the illustrative embodiments may determine whether movements of the robot are within design parameters.

Figure 2:
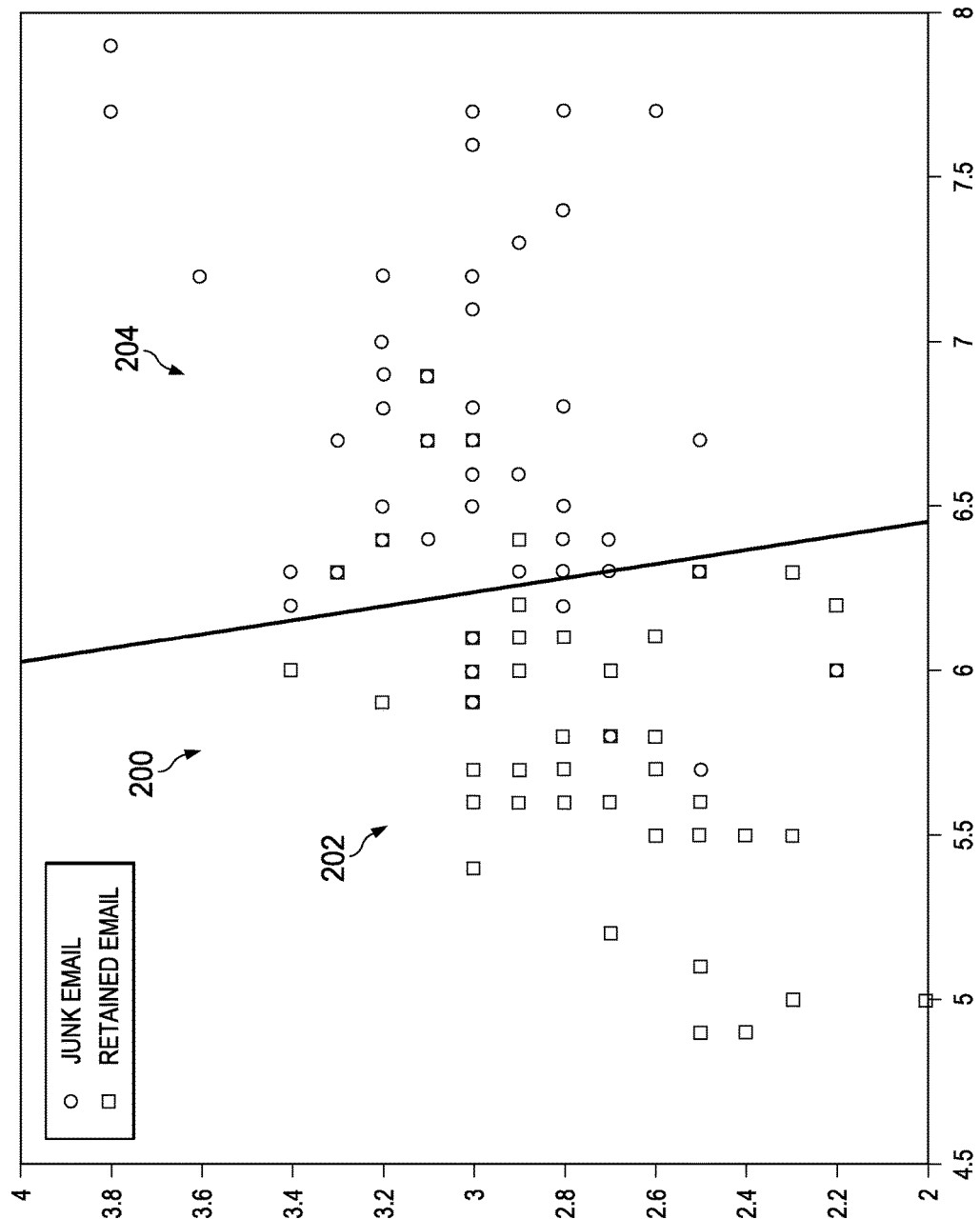
FIG. 2 illustrates an example of a classification system, in accordance with an illustrative embodiment.

FIG. 2 illustrates an example of a classification system, in accordance with an illustrative embodiment. Classification 200 of FIG. 2 illustrates the principles of classification as used herein, not necessarily the illustrative embodiments. In other words, classification 200 illustrates principles of classification that may be used for implementing the illustrative embodiments with respect to determining when to take metrics for particular motions, positions, or activities of users or devices, as described with respect to FIG. 1.

Attention is first turned to what is meant by the term "classification". "Classification," as used herein, is defined as the ability to identify, or the act of identifying, to which group of objects a new observation belongs by comparing a new observation's characteristics to a known set of characteristics. As used in the illustrative embodiments, the known characteristics are established by training the system. "Training the system," as used herein, is defined as providing to the system the characteristics of the known members of the set. Stated differently, training the system instructs the system regarding what a particular position "looks like"; or rather, what the characteristics of the particular position are. When the system is trained, the system may then quickly compare a new observation's characteristics to the set of known members' characteristics, and then equate the new observation as being the one of the known members of the set which most closely matches the new observation's characteristics. As used herein, "the system" or "the illustrative embodiments" refers to a processor, an application specific integrated circuit (ASIC), and/or other physical equipment used or usable to implement the illustrative embodiments, including possibly a non-transitory computer readable storage medium storing program code for implementing the motion capture and classification system described herein.

Returning to FIG. 2, this figure illustrates an example of classification with respect to an email system. In this case, the system classifies incoming email as either retained email or junk email based on certain characteristics. Thus, classification 200 has two known members in the set of known members. These known members are retained email 202 and junk email 204. The system has been trained by establishing first characteristics of retained email 202 and second characteristics of junk email 204. The system is then programmed to compare third characteristics of a new observation, which is an incoming email, to the first characteristics of retained email 202 and the second characteristics of junk email 204. The new observation is then classified as either belonging to retained email 202 or junk email 204.

Again, the characteristics that make up each category, retained email 202 or junk email 204, are already known. For example, retained email 202 typically comes from a recognized sender. Thus, retained email 202 has, as one characteristic, a recognized sender. Other characteristics are also possible. Conversely, junk email 204 typically has a characteristic that it does not come from a recognized sender. Junk email 204 often also has other characteristics, such as the presence of words used in solicitation to sell a product or service. Depending on the number of common matches between characteristics of the new observation and characteristics of the known set of members, the system will establish the appropriate category to place the incoming email.

In the terminology of machine learning, a classification system is considered an instance of supervised learning; that is, learning where a training set of correctly-identified observations is available. The corresponding unsupervised procedure is known as clustering or cluster analysis. Cluster analysis may involve grouping data into categories based on some measure of inherent similarity. An example of measures includes the distance between instances, considered as vectors in a multi-dimensional vector space.

Figure 3:
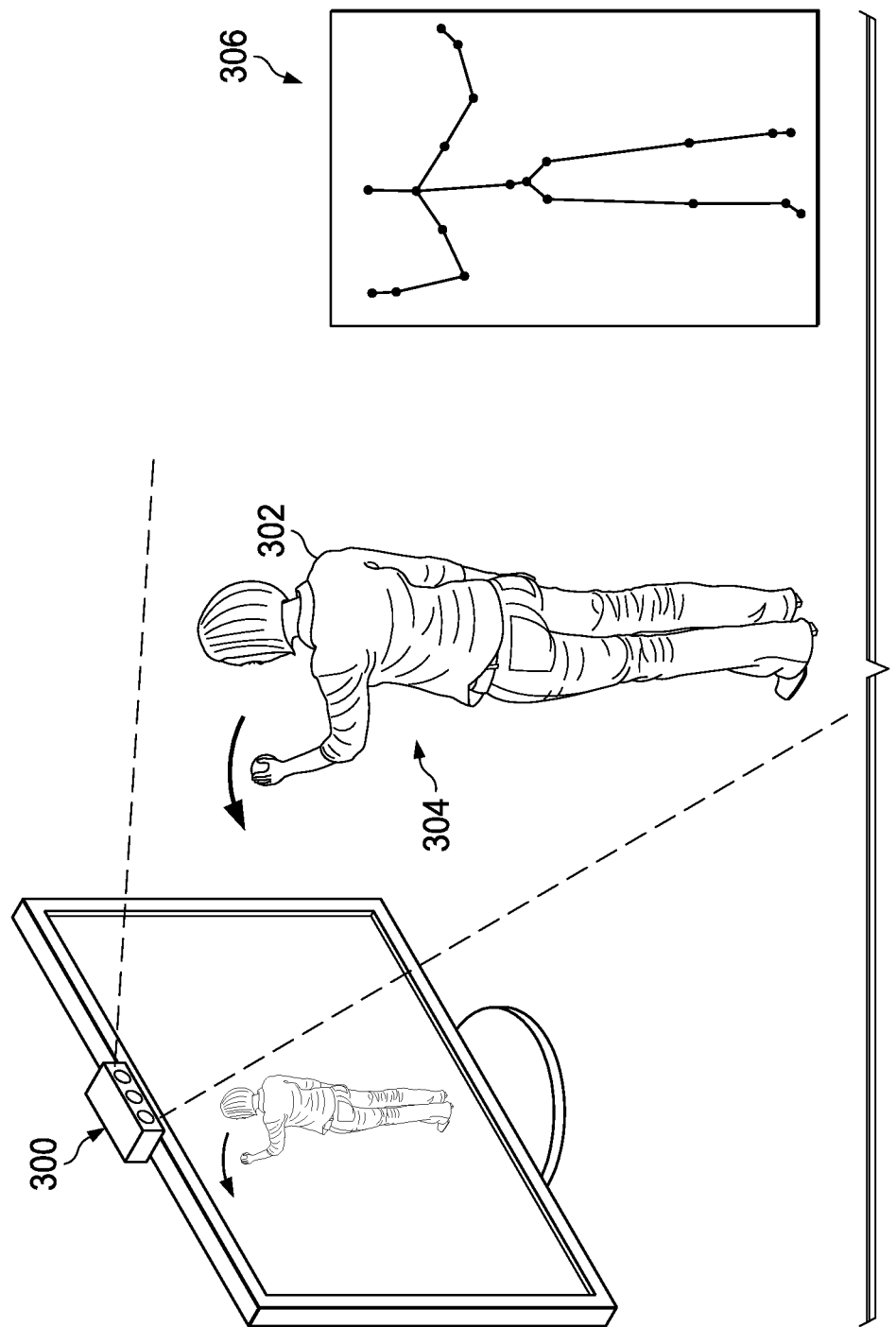
FIG. 3 illustrates an example of a kinematic detection system in use, in accordance with an illustrative embodiment.

FIG. 3 is an example of a kinematic detection system in use, in accordance with an illustrative embodiment. Kinematic detection system 300 may be kinematic detection system 102 of FIG. 1. The movements of user 302 may be classified by the system using a classification system, in a manner analogous to that shown by classification 200 of FIG. 2.

As described above, the illustrative embodiments may use kinematic detection system 300 to movements of user 302. Motion sensing input devices, such as kinematic detection system 102 of FIG. 1, may be used as part of kinematic detection system 300 to detect a change in position of user 302 relative to his or her surroundings 304.

Typically, motion sensing input devices such as kinematic detection system 300 include software which displays the Cartesian coordinates of where the detected movement took place. This display could take the form of a stick person, such as stick person 306, or may not be visually represented at all. In either case, the illustrative embodiments may use the measured coordinates to calculate the movements of user 302.

In order to gauge the subject's movements, the illustrative embodiments may correlate the coordinates of a position shared by all parties, that is to say the illustrative embodiments may compare hand movements to hand movements. The measurements can be further normalized if desired. For example, the illustrative embodiments could also use the distance between parts of the body which are relatively static, such as the center hip to the spine, in normalizing the measurements.

Figure 4:
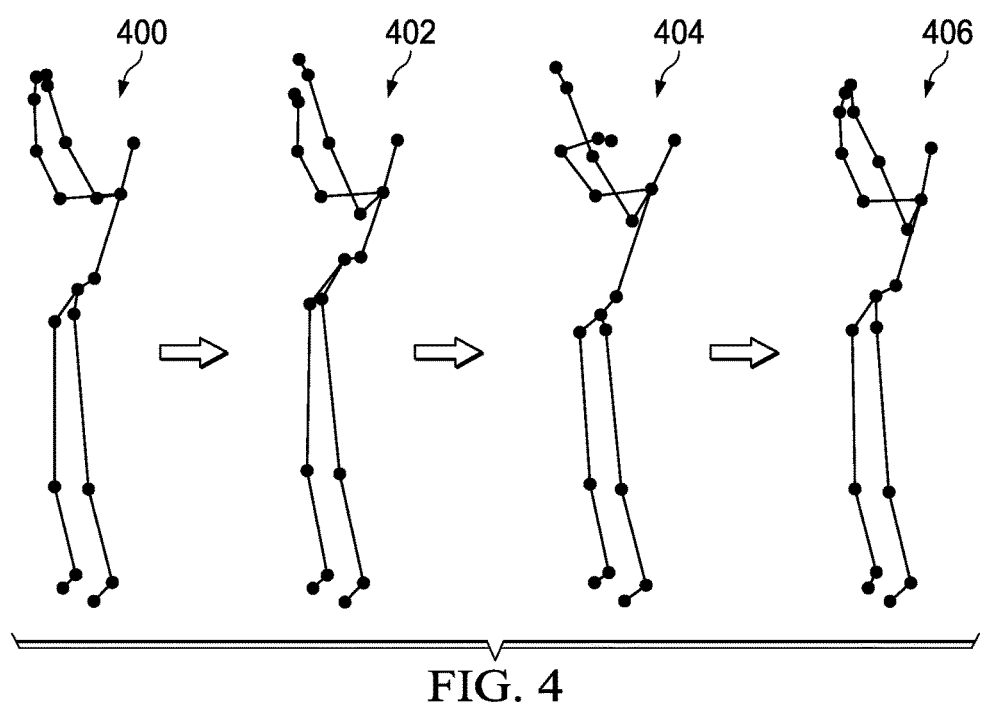
FIG. 4 illustrates an example a pre-recorded activity classified as reaching, in accordance with an illustrative embodiment.
Figure 5:
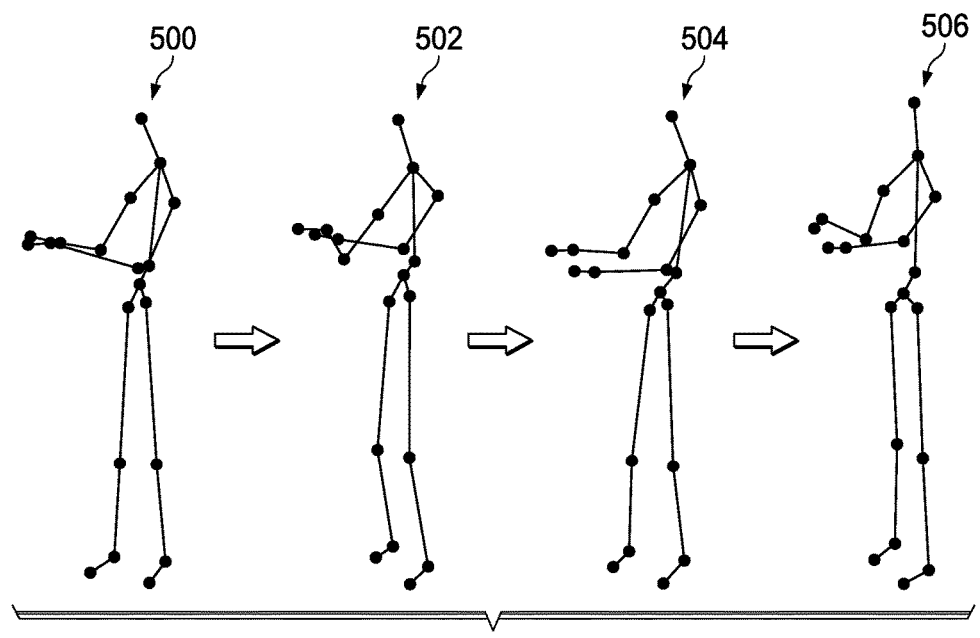
FIG. 5 illustrates an example of a pre-recorded activity classified as standing, in accordance with an illustrative embodiment.
Figure 6:
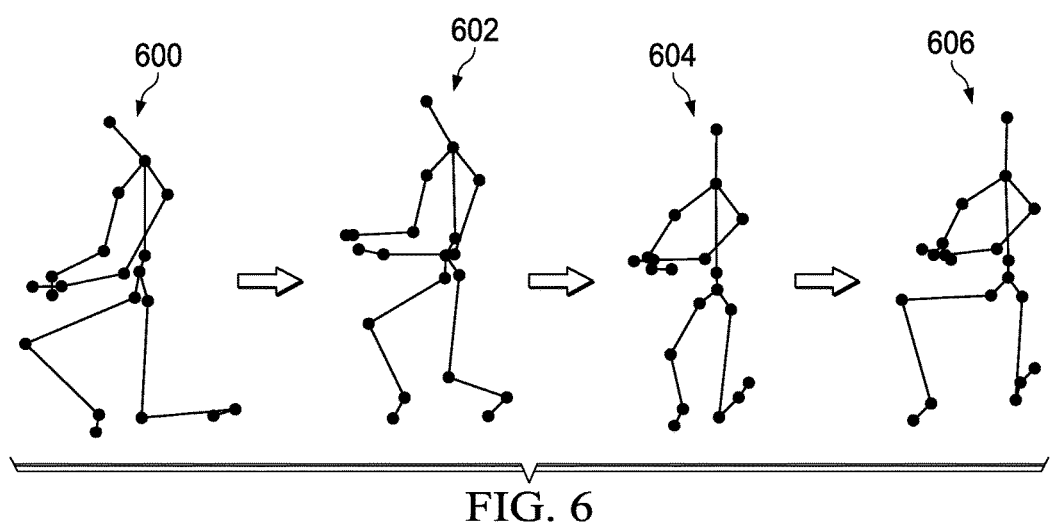
FIG. 6 illustrates an example of a pre-recorded activity classified as kneeling, in accordance with an illustrative embodiment.

FIG. 4, FIG. 5, and FIG. 6 all illustrate examples of pre-recorded activities. Pre-recorded activities are used to train an associative memory, such as associative memory 104 of FIG. 1, so that the associative memory or processor can compare unknown input data to known pre-recorded activities in order to classify the unknown input data as one of the pre-recorded activities. An example of classification is shown in FIG. 2. The input data can be derived from a motion input device, such as kinematic detection system 300 of FIG. 3.

More specifically, FIG. 4 illustrates an example a pre-recorded activity classified as reaching, in accordance with an illustrative embodiment. FIG. 5 illustrates an example of a pre-recorded activity classified as standing, in accordance with an illustrative embodiment. FIG. 6 illustrates an example of a pre-recorded activity classified as kneeling, in accordance with an illustrative embodiment.

In order to improve the quality of matching of unknown input data to a pre-recorded activity, the associative memory can be trained with multiple examples of what constitutes a given activity of interest. Thus, for example, position 400, position 402, position 404, and position 406 are all examples of reaching, even though as shown in FIG. 4 all four positions are somewhat different from each other. Similarly, position 500, position 502, position 504, and position 506 are all examples of standing, even though as shown in FIG. 5 all four positions are somewhat different from each other. Similarly, position 600, position 602, position 604, and position 606 are all examples of kneeling, even though as shown in FIG. 6 all four positions are somewhat different from each other. Note that in the case of FIG. 6, examples of kneeling are taken at different angles relative to the kinematic detection system so that the associative memory can recognize the same position from different angles.

Attention is now turned to what is done once the associative memory has successfully classified an unknown input to one of the positions of interest, such as those shown in FIG. 4 through FIG. 6. A purpose of the illustrative embodiments is to detect if an individual is in a particular position using a kinematic detection system or other motion sensing input device and to gather metrics concerning that position. To achieve this particular purpose, the illustrative embodiments may use an associative memory to store a pre-recorded list of activities. Each activity contains the position or positions for which the user wishes to collect metrics.

Then, during the monitoring phase, an individual's movements may be periodically tested by an associative memory classification to see if they match any of the positions in the pre-recorded activities. If there is a match, the illustrative embodiments collect metrics concerning that position for as long as the individual being monitored maintains the particular position.

The overall process involves a few logical steps. For the purpose of clarity, the following example will describe each step using an example of monitoring an individual installing some equipment, which involves the positions of kneeling, standing, and reaching. The illustrative embodiments will gather metrics with respect to these positions. For this example, the metrics collected will be the duration the individual maintains each position. Note, however, that this specific example does not necessarily limit the claimed inventions or the other illustrative embodiments described herein; many other examples are possible as explained elsewhere herein.

In this particular illustrative embodiment, the first step is to identify the positions for which a user wants to collect metrics. These positions could be part of an overall movement or activity, such as "tying a shoe" or they could be as simple as a stationary position, such as "kneeling".

In either case, in the next, second step the user will demonstrate each move in front of a motion sensor and record them respectively. These recordings will become the basis for the associative memory's classification. For this installation example, the positions for which metrics are to be identified would be kneeling, standing, and reaching. The metrics for these positions would be their durations.

The purpose of recording the activities described in this second step is to tell the classification system which position or positions need metrics collected. During this second step, a user need only demonstrate each activity to the extent that a particular position is captured.

For example, if one desired to gather metrics pertaining to someone reaching, one could demonstrate reaching, by extending one's body a few times in a reaching motion, as conceptualized in FIG. 4. For example, a user could simulate the installation of a luggage rack into an airplane's cabin. The user would repeat this process for the other positions, standing and kneeling, as conceptualized in FIG. 5 and FIG. 6, respectively.

Each activity could be demonstrated a few times, using different people and recorded from different angles. Multiple demonstrations by each of multiple different people will provide the associative memory a rich description for each desired outcome.

Figure 7:
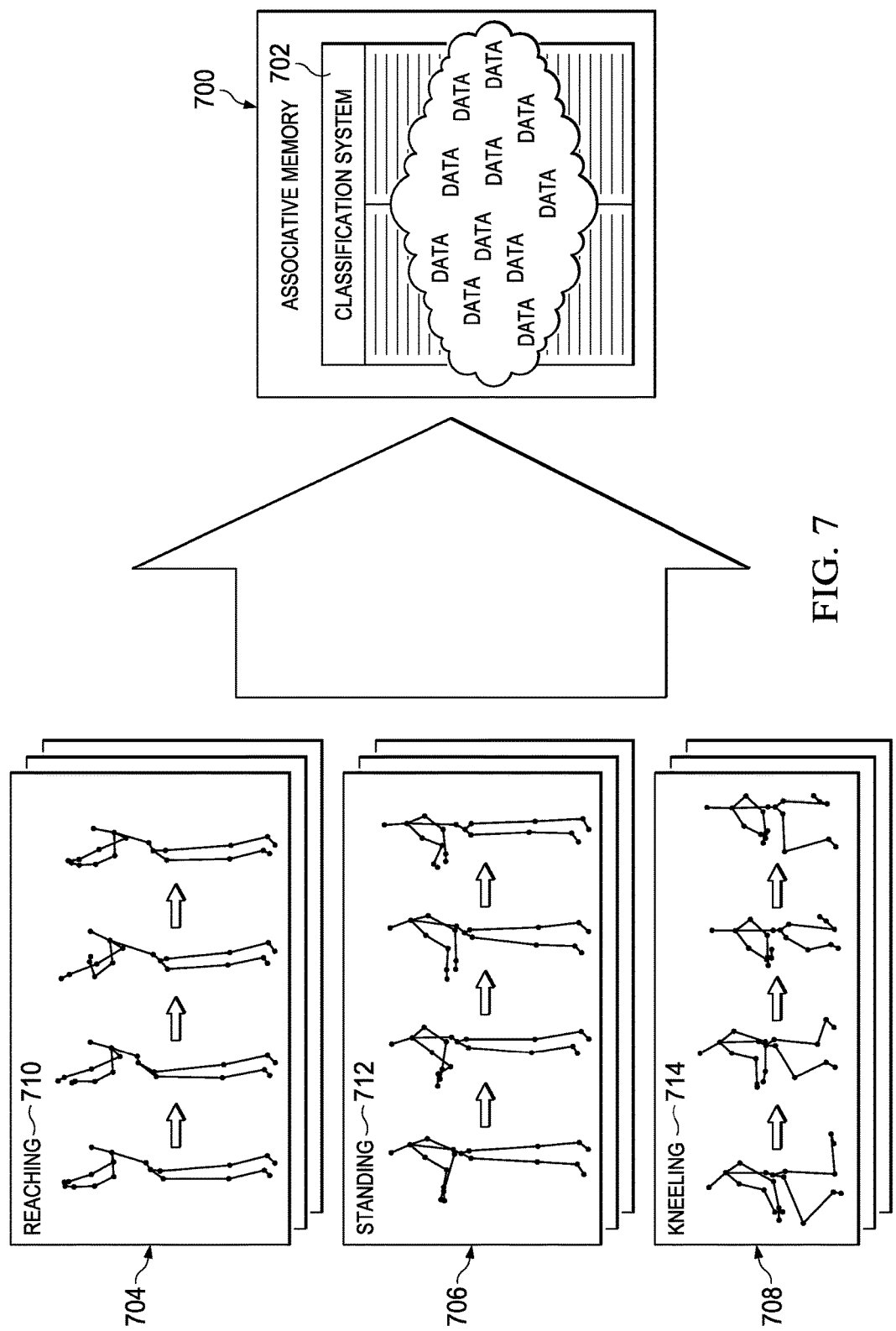
FIG. 7 illustrates an example of inserting activities into a classification system, in accordance with an illustrative embodiment.

FIG. 7 illustrates an example of inserting activities into a classification system, in accordance with an illustrative embodiment. FIG. 7 illustrates a third step in the process started above, which is training the associative memory. The first step (identifying the positions of interest) and the second step (demonstrating examples of positions to train the associative memory) are described above with respect to FIG. 4 through FIG. 6. Associative memory 700 may be, for example, associative memory 104 of FIG. 1. Classification system 702 may be used, for example, to perform classification 200 of FIG. 2. The demonstrated input of reaching 704, standing 706, and kneeling 708 may be, for example, those shown in FIG. 4, FIG. 5, and FIG. 6, respectively.

As stated similarly above, the pre-recorded activities, described in step 2, represent truth data used to train the classification system, which may be classification system 702 of associative memory 700. Each recording is accompanied by an outcome, such as outcome 710, outcome 712, and outcome 714, describing the intent of the movement. During the training phase, associative memory 700 associates each recording's outcome with all the corresponding positions captured, in order to classify the captured corresponding positions. The outcome is what the classification returns, if there is a match. In this case, the outcome is known as the "classifier".

Because the illustrative embodiments capture the positions as a series of movements, the underlying classification is more flexible. This technique allows a match to occur at any point during the activity in order to conclude that the individual was in fact doing the activity. As a result, the illustrative embodiments place the emphasis on the mechanics of the activity, rather than its nuances. Thus, this technique uses less processing power than tracking the precise positions of body parts of the individual. Once the training is complete, the illustrative embodiments insert the captured data into an associative memory, where new observations can then be classified against the collected data to determine a particular outcome and gather metrics if necessary.

For the installation example, the classification system would use the pre-record activities of kneeling, standing, and reaching to train the system. This training is, again, the third step in the process. The complete set would be inserted into classification system 702 of associative memory 700 as demonstrated in FIG. 7.

Figure 8:
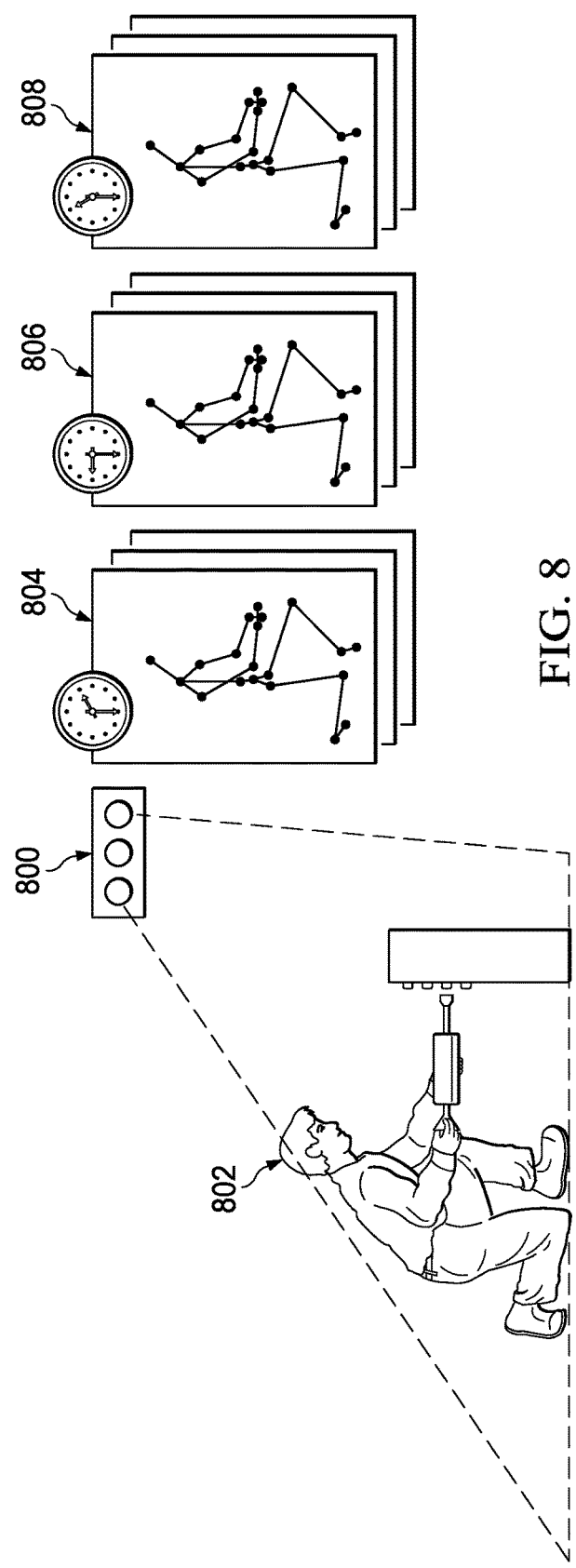
FIG. 8 illustrates an example of monitoring activities, in accordance with an illustrative embodiment.

FIG. 8 illustrates an example of monitoring activities, in accordance with an illustrative embodiment. Monitoring represents a fourth step in the process began above, with the first and second steps described with respect to FIG. 4 through FIG. 6 and the third step described with respect to FIG. 7. Kinematic detection system 800 may be, for example, kinematic detection system 300 of FIG. 3. Kinematic detection system 800 may also be referred-to as a motion sensing input device.

During the fourth step of monitoring, the system periodically collects information from kinematic detection system 800. The system may collect this information as a single frame or multiple frames, depending how the system is configured. The frame or frames provide a current snapshot of what the motion sensor sees at the time the sensor is queried. The goal is to determine whether an individual is in some position, perhaps the pre-identified position for which metrics can be collected.

The fifth step is to identify the captured position using an associative memory classification or some other classification system. The associative memory classifies the position of human 802 by matching the characteristics of an unknown position of human 802 with those characteristics of the known position previously recorded. Note that human 802 need not have been the same person who demonstrated the positions within the training, for example, the pre-recorded activities. In any case, the system will classify the unknown position accordingly. If the classification system does not match any of the pre-recorded activities, then the classification system will return an empty result and accordingly no metrics will be collected.

FIG. 8 shows that human 802 is kneeling. Kinematic detection system 800 will classify human 802 as kneeling. Because the time kneeling (the metric of interest) is to be recorded during the collection of metrics in step 6, the amount of time that human 802 spends kneeling will be tracked. This time need not be contiguous. For example, human 802 could kneel for a time, stand for a time such that metrics are no longer recorded, kneel again during which the time spent kneeling is recorded, reach for a time such that metrics are no longer recorded, and then kneel a third time during which the time spent kneeling is recorded. Thus, FIG. 8 shows three different times during which the amount of time spent kneeling is recorded, time 804, time 806, and time 808.

The collection of metrics continues for as long as the individual being monitored maintains a position of interest.

When not collecting, the method returns to monitoring phase, outlined in step 3, and continues until the system is asked to stop.

Figure 9:
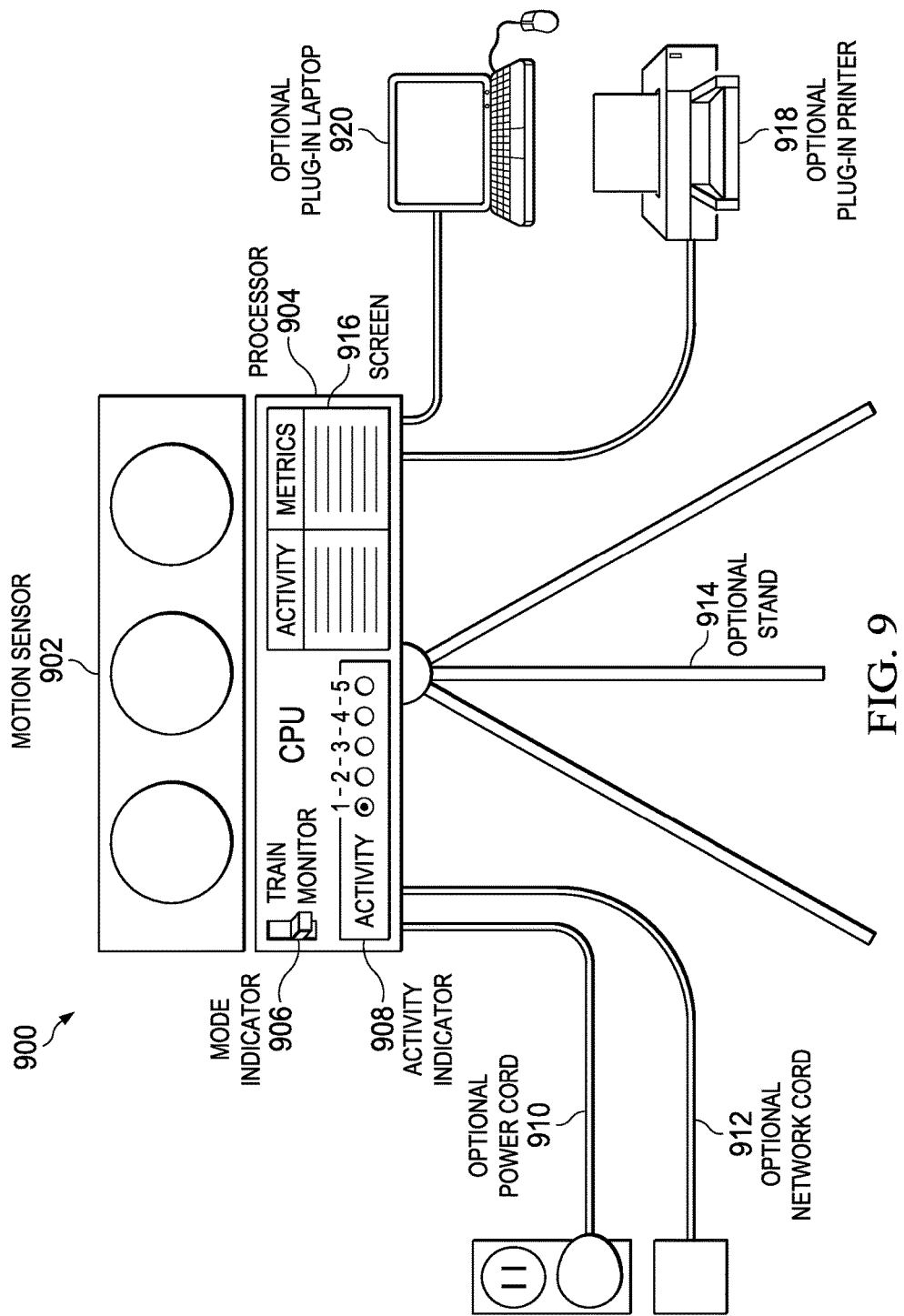
FIG. 9 illustrates an example of a system for collecting metrics using an associative memory, in accordance with an illustrative embodiment.

FIG. 9 illustrates an example of a system for collecting metrics using an associative memory, in accordance with an illustrative embodiment. Kinematic detection system 900 may be, for example, kinematic detection system 102 of FIG. 1 or kinematic detection system 300 of FIG. 3 or kinematic detection system 800 of FIG. 8. The computer or processors used in kinematic detection system 900 may be implemented using data processing system 1500 of FIG. 15.

One possible physical embodiment of the illustrative embodiments is illustrated in FIG. 9, though other physical embodiments are possible. As shown, kinematic detection system 900 uses motion sensor 902 connected to processor 904 that executes the software used to implement the illustrative embodiments, including possibly an associative memory. The computer containing processor 904 may include mode indicator 906 used to indicate whether the device is in training mode or monitor mode. The computer may also include activity indicator 908 to indicate which activity is to be trained.

Kinematic detection system 900 could include optional power cord 910 or a battery. Kinematic detection system 900 could also include optional network cord 912 or a wireless device connecting kinematic detection system 900 to a network. In any case, kinematic detection system 900 may communicate with an associative memory, database, or any other system used to implement the illustrative embodiments. However, in some illustrative embodiments, all the software used may be contained within processor 904 itself. In other illustrative embodiments, the software may instead be embodied as an application specific integrated circuit (ASIC).

Kinematic detection system 900 may include other optional devices or objects. For example, kinematic detection system 900 may include optional stand 914 or be placed somewhere motion sensor 902 could easily observe movements. Kinematic detection system 900 also could include screen 916, or some other output device such as printer or other indicator, used to report or display output. Optionally, plug-in printer 918 may be provided to print out reports, metrics, or other output.

Finally, optional plug-in laptop 920, tablet, mobile phone, or other computer system could be used to help configure or optimize kinematic detection system 900. In addition, plug-in laptop 920 could also be used to update software as desired.

Either processor 904 or plug-in laptop 920 could be used as part of a system for collecting metrics on positions of a person or of an object. Thus, for example, either of processor 904 or plug-in laptop 920 could be used in conjunction with an associative memory connected to either of these devices to monitor a person or object, classify positions of the person or object, and then collect metrics on specific positions of the person or object, as described above.

Stated differently, one possible embodiment of the illustrative embodiments is illustrated in FIG. 9. As shown, kinematic detection system 900 uses motion sensor 902 connected to a CPU device containing software useful for implementing the illustrative embodiments. The CPU device may have mode indicator 906 used to switch modes. For example, the CPU device could be set to training or monitoring. Activity indicator 908 may allow the user to select a predetermined activity for the purpose of identifying which activity the system is training for. For example, these indicators could correspond to a supplementary list which explains which activities are captured.

The illustrative embodiment could include optional power cord 910 or a battery. The illustrative embodiment could also include optional network cord 912 or a wireless device connecting it to a network, so an associative memory, database or any other system credentials could be accessed. However, it is possible to place all the necessary software for the illustrative embodiments within the CPU device itself.

The illustrative embodiments could include optional stand 914 or be placed somewhere else secure. The illustrative embodiments could include a report output, such as screen 916, used for displaying the results of the metrics it gathered. Optional plug-in laptop 920 could be used to help configure, update or optimize the illustrative embodiments. Another option would be to include optional plug-in printer 918, allowing user access to hard copies of reports or metrics on site.

The illustrative embodiments shown in FIG. 9 are not meant to imply physical or architectural limitations to the manner in which different illustrative embodiments may be implemented. Other components in addition to and/or in place of the ones illustrated may be used. Some components may be unnecessary in some illustrative embodiments. Also, the blocks are presented to illustrate some functional components. One or more of these blocks may be combined and/or divided into different blocks when implemented in different illustrative embodiments.

FIG. 10 illustrates an example of an entity comparison with outcomes as a result category, in accordance with an illustrative embodiment. Entity comparison 1000 is an example of how an associative memory, such as associative memory 104 of FIG. 1, can classify an unknown input against a set of training positions, as described above with respect to FIG. 4 through FIG. 9.

One possible implementation of the illustrative embodiments is to use an inexpensive motion sensor to capture the activities of interest and a structured query language (SQL) database to record them. Then an associative memory could be used to classify new observations, supplied by the motion sensor, against the pre-recorded ones.

For this implementation, a user would setup a predefined database and insert the training data, captured by the motion sensor. The training data's outcome would be labeled accordingly, corresponding to each position for which metrics were desired. Then, using an associative memory, a user would ingest this data into the associative memory for the purpose of classifying new observations against it. The data's outcome would be used as the general classifier.

Once ingested, the user could have the system periodically capture movement data from a motion sensor and perform an entity comparison on the captured data to locate other movements like it. The result category of the entity comparison would be set to the "outcome". As a result, the new observation would adopt the outcome of the movement with which it most identifies, as shown in FIG. 10. Thus, for example, set of common attributes 1002 that belong to the outcome 1004 of "reaching" match those attributes of new observation 1006. Score 1008 may be on a scale from zero to one, and represents the closeness of match of the unknown input's attributes to the demonstrated position or activity's attributes. Other score forms or scales could be used for score 1008.

Typically, the results of an entity comparison are an ordered list of entities that are "like" or "similar to" the original or sought entity. An associative memory collects all the matching attributes among these entities to formulate the list. The order of that list depends on the significance of the matching attributes. Additionally, its ranking or score correlates to the number of attributes found.

For a clearer result, the system can perform an entity comparison using a predefined outcome as a result category. The memory can be preconfigured to have each entity associate itself with a particular outcome, such kneeling, standing, or reaching. This technique is an effective way of classifying new observations using a result category, in this case, the outcome as the general classifier.

The illustrative embodiments may be applicable to private companies, governments, or other organizations that are interested in collecting metrics with concerns relating to how employees are performing their daily tasks. The illustrative embodiments allow large scale manufactures to collect such metrics non-invasively.

For example, any company which employs a union contracted staff or is subject to union regulations could utilize the illustrative embodiments. The data is collected without being intrusive and is recorded in a way in which identifying specific individuals is physically impossible. These advantages allow for monitoring and metric gathering in work environments where video monitoring of individuals is prohibited.

The illustrative embodiments provide an efficient way to monitor and measure activities in areas where doing so might be difficult. Furthermore, the illustrative embodiments can provide metrics for positions which are difficult to measure any other way.

The illustrative embodiments provide a cost efficient way of collecting metrics on how long an employee maintains a potentially undesirable position, thereby helping to avoid increased medical costs. The illustrative embodiments could be used to gather safety metrics, which a company could use to quantify results when trying to measure safety goals. The illustrative embodiments could be used within a factory to benchmark safety goals and showcase examples of good versus bad posture. The illustrative embodiments could be used to measure the frequency of repetitive motion injuries, in hopes of preventing them. The illustrative embodiments could be used to measure how often incorrect ergonomics occur within an office building in hopes of educating employees. The illustrative embodiments can provide metrics on positions which are otherwise impossible to measure. This fact could be utilized in places where supervisors suspect certain manufacturing tasks might be causing harm. Other advantages exist.

Figure 11:
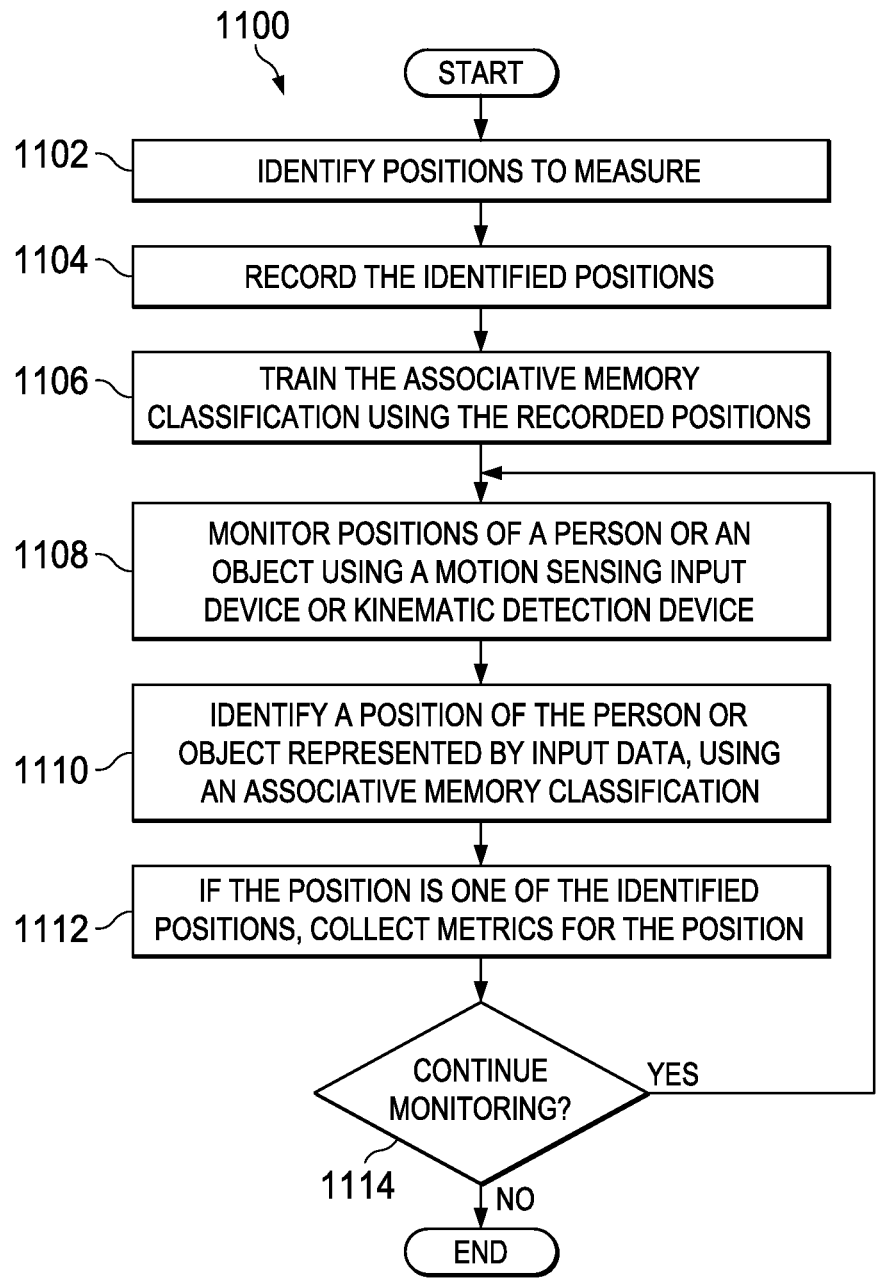
FIG. 11 is a flowchart of a method for identifying a motion of interest of an individual, in accordance with an illustrative embodiment.

FIG. 11 is a flowchart of a method for identifying a motion of interest of an individual, in accordance with an illustrative embodiment. Method 1100 may be a synthesis of the six steps described with respect to FIG. 4 through FIG. 8. However, more or fewer operations may be performed. Method 1100 may be implemented using any of the systems described in FIG. 1 through FIG. 3, as well as FIG. 8 and FIG. 9. For example, reference to "the system" may be to system 900 of FIG. 9, though may refer to another device for carrying out the operations described below.

Method 1100 may begin with the system identifying positions to measure (operation 1102). These positions may be positions or activities of a person or object. The system then records the identified positions (operation 1104). The identified positions may be recorded by a user or an object performing the positions or activities which are to be monitored later.

Method 1100 continues by training the associative memory classification using the recorded positions (operation 1106). The associative memory may be trained by commanding the associative memory to ingest the recorded positions.

Next, the system monitors positions of a person or an object using a motion sensing input device or kinematic detection device (operation 1108). These operations are described with respect to FIG. 8. The system then identifies a position of the person or object represented by input data, using an associative memory classification (operation 1110). This operation is also described with respect to FIG. 8. If the position is one of the identified positions, then metrics are collected for the position (operation 1112). This operation is also described with respect to FIG. 8.

A determination is then made whether to continue monitoring (operation 1114). If monitoring is to continue, then method 1100 returns to operation 1108 and continues. If monitoring is not to continue, then the process may terminate.

The illustrative embodiments shown in FIG. 11 are not meant to imply physical or architectural limitations to the manner in which different illustrative embodiments may be implemented. Other components in addition to and/or in place of the ones illustrated may be used. Some components may be unnecessary in some illustrative embodiments. Also, the blocks are presented to illustrate some functional components. One or more of these blocks may be combined and/or divided into different blocks when implemented in different illustrative embodiments.

Figure 12:
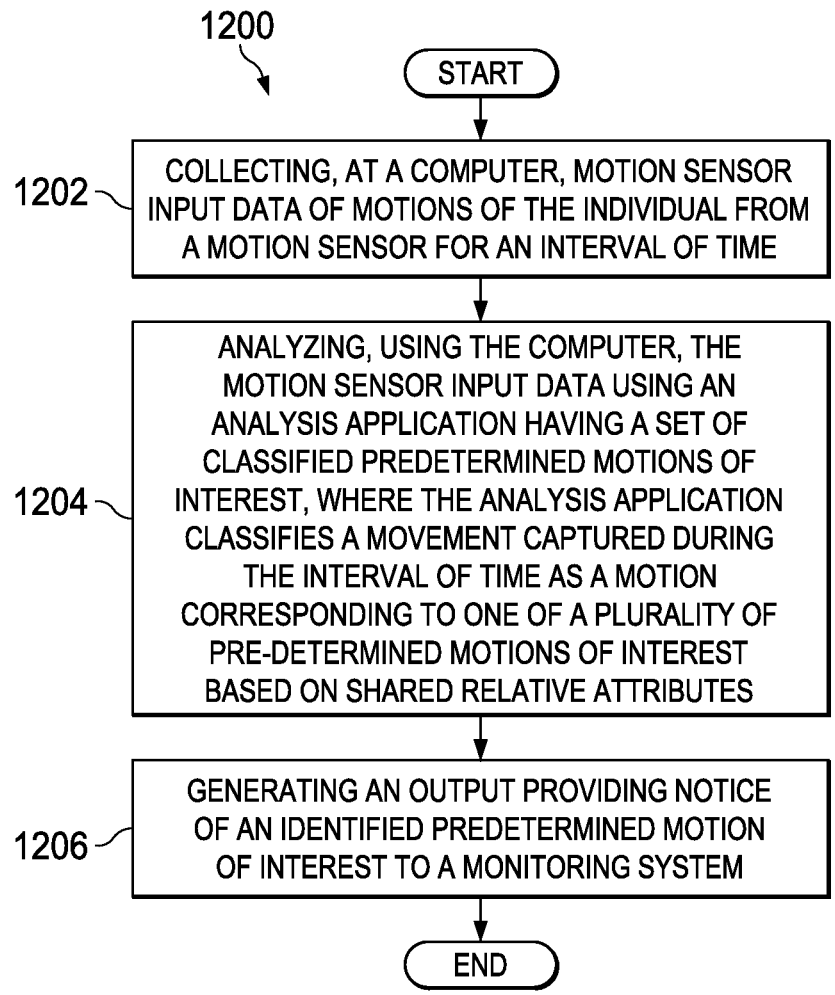
FIG. 12 is another flowchart of a method for identifying a motion of interest of an individual, in accordance with an illustrative embodiment.

FIG. 12 is another flowchart of a method for identifying a motion of interest of an individual, in accordance with an illustrative embodiment. Method 1200 is a variation of method 1100. Thus, method 1100 may be a synthesis of the six steps described with respect to FIG. 4 through FIG. 8. However, more or fewer operations may be performed. Method 1100 may be implemented using any of the systems described in FIG. 1 through FIG. 3, as well as FIG. 8 and FIG. 9. For example, reference to "the system" may be to system 900 of FIG. 9, though may refer to another device for carrying out the operations described below.

Method 1200 may be characterized as a method for identifying a motion of interest of an individual. Method 1200 may include collecting, at a computer, motion sensor input data of motions of the individual from a motion sensor for an interval of time (operation 1202). Next, method 1200 may include analyzing, using the computer, the motion sensor input data using an analysis application having a set of classified predetermined motions of interest, where the analysis application classifies a movement captured during the interval of time as a motion corresponding to one of a plurality of pre-determined motions of interest based on shared relative attributes (operation 1204). Next, method 1200 may include generating an output providing notice of an identified predetermined motion of interest to a monitoring system (operation 1206). The process may terminate thereafter.

However, method 1200 may be varied, and may include more or fewer operations. For example, method 1200 may further include the system generating an alarm output when an identified predetermined motion of interest exceeds a predetermined threshold. Method 1200 may further include, responsive to receiving the notice, collecting metrics on the motion of interest. Method 1200 may further include, responsive to receiving the notice, collecting metrics on additional movements by the individual.

The illustrative embodiments shown in FIG. 12 are not meant to imply physical or architectural limitations to the manner in which different illustrative embodiments may be implemented. Other components in addition to and/or in place of the ones illustrated may be used. Some components may be unnecessary in some illustrative embodiments. Also, the blocks are presented to illustrate some functional components. One or more of these blocks may be combined and/or divided into different blocks when implemented in different illustrative embodiments.

Figure 13:
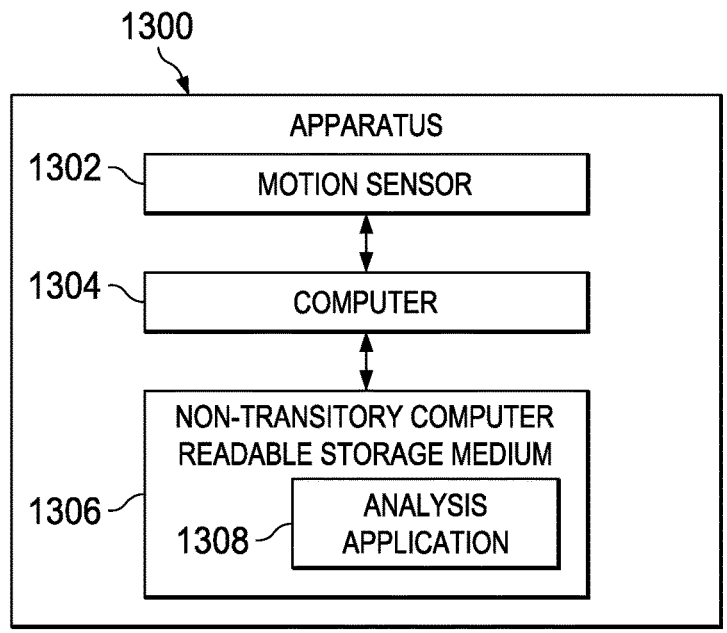
FIG. 13 is an apparatus for identifying a motion of interest of an individual, in accordance with an illustrative embodiment.

FIG. 13 is an apparatus for identifying a motion of interest of an individual, in accordance with an illustrative embodiment. Apparatus 1300 may be a variation of system 900 of FIG. 9. Apparatus 1300 may be characterized as an apparatus for identifying a motion of interest of an individual.

Apparatus 1300 may include motion sensor 1302. Motion sensor 1302 may be non-invasive. Apparatus 1300 may also include computer 1304 in communication with the motion sensor, computer 1304 being configured to collect motion sensor data from motion sensor 1302 on motions of the individual for an interval of time. Computer 1304 may be, for example, data processing system 1500 of FIG. 15.

Apparatus 1300 may also include non-transitory computer readable storage medium 1306 storing analysis application 1308 having a set of classified pre-determined motions of interest. Analysis application 1308 may be further configured such that when executed by computer 1304, analysis application 1308 classifies a movement of the individual captured during the interval of time as a motion corresponding to one of a plurality of predetermined motions of interest based on shared relative attributes. Analysis application 1308 may be further configured, when executed, to generate an output providing notice of an identified predetermined motion of interest to a monitoring system.

Apparatus 1300 may be varied. For example, the processor may be further configured to generate an alarm output when an identified predetermined motion of interest exceeds a pre-determined threshold. Computer 1304 may be further configured, responsive to receiving the notice, to collect metrics on the motion of interest. Computer 1304 may be further configured, responsive to receiving the notice, to collect metrics on additional movements by the individual.

The illustrative embodiments shown in FIG. 13 are not meant to imply physical or architectural limitations to the manner in which different illustrative embodiments may be implemented. Other components in addition to and/or in place of the ones illustrated may be used. Some components may be unnecessary in some illustrative embodiments. Also, the blocks are presented to illustrate some functional components. One or more of these blocks may be combined and/or divided into different blocks when implemented in different illustrative embodiments.

Figure 14:
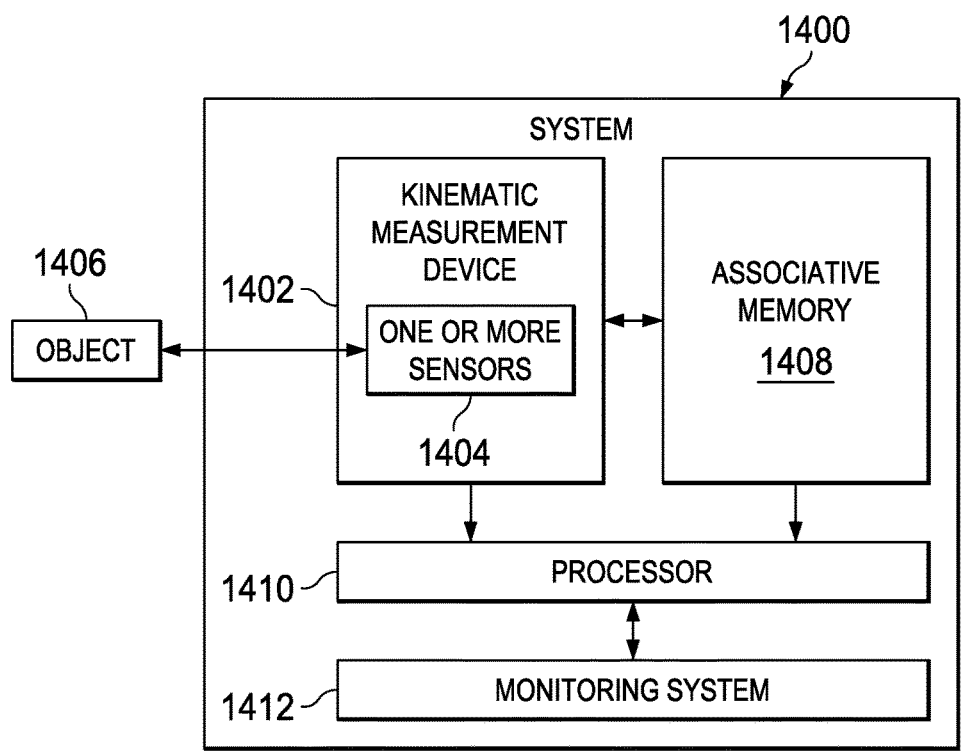
FIG. 14 is a system for notifying a monitoring system when a particular motion matches one of a subset of the plurality of pre-determined motions, in accordance with an illustrative embodiment.

FIG. 14 is a system for notifying a monitoring system when a particular motion matches one of a subset of the plurality of pre-determined motions, in accordance with an illustrative embodiment. System 1400 may be a variation of system 900 of FIG. 9 and system 1400 of FIG. 14.

System 1400 may include kinematic measurement device 1402 having one or more sensors 1404 configured to detect a plurality of physical positions of a part of an object 1406. System 1400 may also include associative memory 1408 in communication with kinematic measurement device 1402. Associative memory 1408 may include a plurality of data and a plurality of associations among the plurality of data. The plurality of data is collected into associated groups. The associative memory is configured to be queried based on at least indirect relationships among the plurality of data.

System 1400 may further include processor 1410. Processor 1410 may be in communication with associative memory 1408 and kinematic measurement device 1402. Processor 1410 may be configured to receive motion input data of the object from kinematic measurement device 1402, compare, in conjunction with associative memory 1408, the motion input data to a plurality of pre-determined motions stored in associative memory 1408, classify the motion input data as a particular motion selected from the plurality of pre-determined motions, and to notify monitoring system 1412 when the particular motion matches one of a subset of the plurality of pre-determined motions. Monitoring system 1412 may be configured to monitor metrics for the pre-determined motions.

For example, processor 1401 may be further configure to cause monitoring system 1412 to measure additional motions of the object when the particular motion matches the one of the subset of the plurality of pre-determined motions. Monitoring system 1412 may be configured to monitor an amount of time the object spends in the pre-determined position.

In another illustrative embodiment, processor 1410 in conjunction with associative memory 1408 may be configured to output an assessment of the additional motions the object. In an illustrative embodiment, the subset may be based on a criteria selected by a user.

In an illustrative embodiment, the object may be a person. In an illustrative embodiment, the subset may be at least one undesirable body position of the person. In an illustrative embodiment, the additional motions may be all motions of the person during an interval of time. In an illustrative embodiment, the additional motions may be only those motions that are within the subset during an interval of time.

In an illustrative embodiment, monitoring system 1412 may monitor motions of an individual body part of the person. In an illustrative embodiment, processor 1410 may be further configured to notify monitoring system 1412 when the motions of the person are no longer in the subset.

In an illustrative embodiment, processor 1410 may be further configured to command monitoring system 1412 to cease monitoring the person when the motions of the person are outside of the subset. In an illustrative embodiment, associative memory 1408 may be configured to be trained to include an additional pre-determined motion within the plurality of pre-determined motions and to include a further motion in the subset of the plurality of pre-determined motions.

Other alternatives are also possible. Thus, the illustrative embodiments shown in FIG. 14 are not meant to imply physical or architectural limitations to the manner in which different illustrative embodiments may be implemented. Other components in addition to and/or in place of the ones illustrated may be used. Some components may be unnecessary in some illustrative embodiments. Also, the blocks are presented to illustrate some functional components. One or more of these blocks may be combined and/or divided into different blocks when implemented in different illustrative embodiments.

Figure 15:
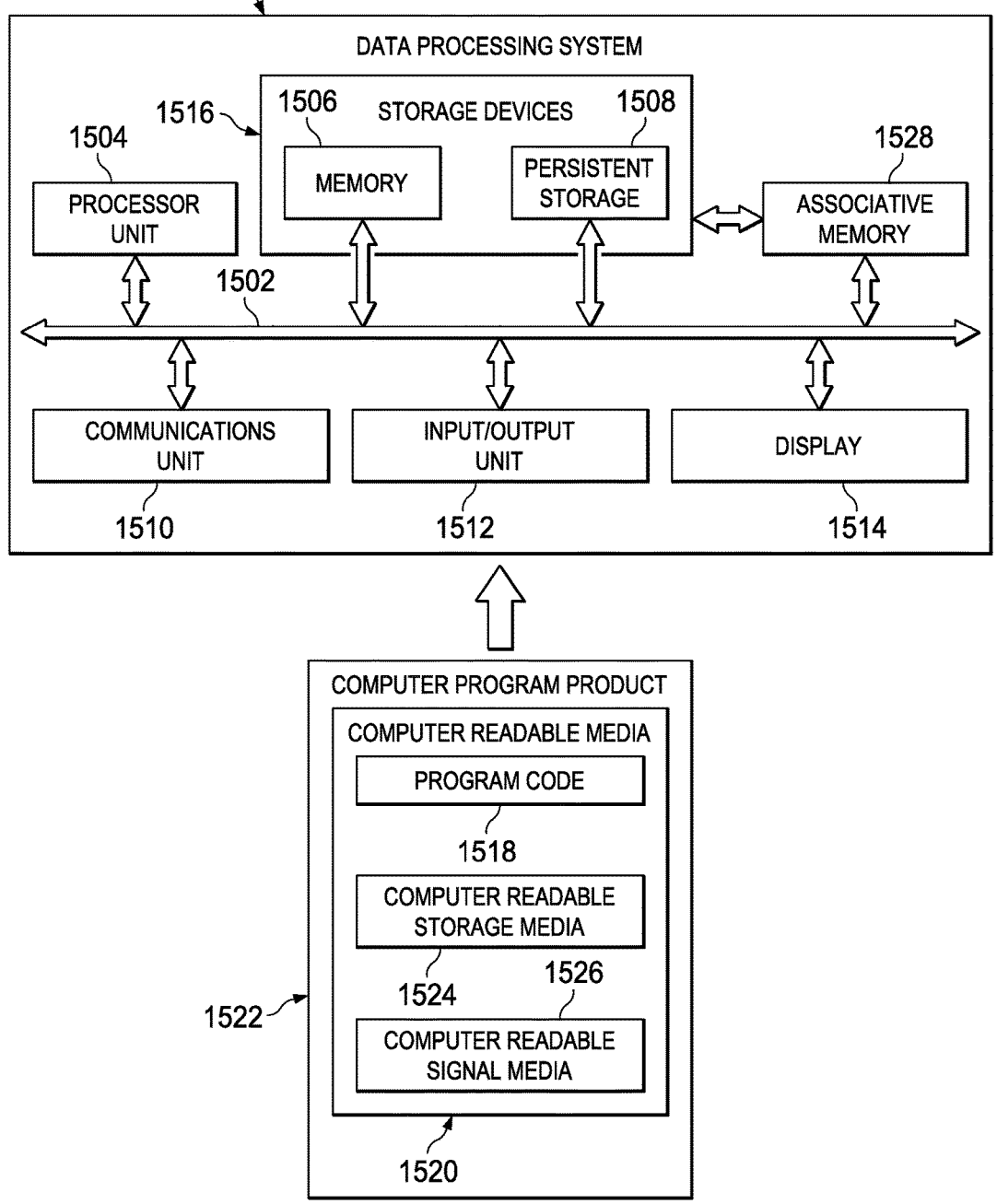
FIG. 15 illustrates a data processing system, in accordance with an illustrative embodiment.

Turning now to FIG. 15, an illustration of a data processing system is depicted in accordance with an illustrative embodiment. Data processing system 1500 in FIG. 15 is an example of a data processing system that may be used to implement the illustrative embodiments, such as kinematic detection system 102 of FIG. 1, operation 1204 or optional plug-in laptop 920, of FIG. 9, computer 1304 of FIG. 13, processor 1410 of FIG. 14, computer readable media 1520 of FIG. 15, or any other module or system or process disclosed herein. In this illustrative example, data processing system 1500 includes communications fabric 1502, which provides communications between processor unit 1504, memory 1506, persistent storage 1508, communications unit 1510, input/output (I/O) unit 1512, and display 1514.

Processor unit 1504 serves to execute instructions for software that may be loaded into memory 1506. This software may be any of the associative memories described elsewhere herein, or software for implementing the processes described elsewhere herein. Thus, for example, software loaded into memory 1506 may be software for executing method 1100 of FIG. 11, method 1200 of FIG. 12, or for implementing the six steps described above with respect to FIG. 4 through FIG. 8. Processor unit 1504 may be a number of processors, a multi-processor core, or some other type of processor, depending on the particular implementation. A number, as used herein with reference to an item, means one or more items. Further, processor unit 1504 may be implemented using a number of heterogeneous processor systems in which a main processor is present with secondary processors on a single chip. As another illustrative example, processor unit 1504 may be a symmetric multi-processor system containing multiple processors of the same type.

Memory 1506 and persistent storage 1508 are examples of storage devices 1516. A storage device is any piece of hardware that is capable of storing information, such as, for example, without limitation, data, program code in functional form, and/or other suitable information either on a temporary basis and/or a permanent basis. Storage devices 1516 may also be referred to as computer readable storage devices in these examples. Memory 1506, in these examples, may be, for example, a random access memory or any other suitable volatile or non-volatile storage device. Persistent storage 1508 may take various forms, depending on the particular implementation.

For example, persistent storage 1508 may contain one or more components or devices. For example, persistent storage 1508 may be a hard drive, a flash memory, a rewritable optical disk, a rewritable magnetic tape, or some combination of the above. The media used by persistent storage 1508 also may be removable. For example, a removable hard drive may be used for persistent storage 1508.

Communications unit 1510, in these examples, provides for communications with other data processing systems or devices. In these examples, communications unit 1510 is a network interface card. Communications unit 1510 may provide communications through the use of either or both physical and wireless communications links.

Input/output (I/O) unit 1512 allows for input and output of data with other devices that may be connected to data processing system 1500. For example, input/output (I/O) unit 1512 may provide a connection for user input through a keyboard, a mouse, and/or some other suitable input device. Further, input/output (I/O) unit 1512 may send output to a printer. Display 1514 provides a mechanism to display information to a user.

Instructions for the operating system, applications, and/or programs may be located in storage devices 1516, which are in communication with processor unit 1504 through communications fabric 1502. In these illustrative examples, the instructions are in a functional form on persistent storage 1508. These instructions may be loaded into memory 1506 for execution by processor unit 1504. The processes of the different embodiments may be performed by processor unit 1504 using computer implemented instructions, which may be located in a memory, such as memory 1506.

These instructions are referred to as program code, computer usable program code, or computer readable program code that may be read and executed by a processor in processor unit 1504. The program code in the different embodiments may be embodied on different physical or computer readable storage media, such as memory 1506 or persistent storage 1508.

Program code 1518 is located in a functional form on computer readable media 1520 that is selectively removable and may be loaded onto or transferred to data processing system 1500 for execution by processor unit 1504. Program code 1518 and computer readable media 1520 form computer program product 1522 in these examples. In one example, computer readable media 1520 may be computer readable storage media 1524 or computer readable signal media 1526. Computer readable storage media 1524 may include, for example, an optical or magnetic disk that is inserted or placed into a drive or other device that is part of persistent storage 1508 for transfer onto a storage device, such as a hard drive, that is part of persistent storage 1508. Computer readable storage media 1524 also may take the form of a persistent storage, such as a hard drive, a thumb drive, or a flash memory, that is connected to data processing system 1500. In some instances, computer readable storage media 1524 may not be removable from data processing system 1500.

Alternatively, program code 1518 may be transferred to data processing system 1500 using computer readable signal media 1526. Computer readable signal media 1526 may be, for example, a propagated data signal containing program code 1518. For example, computer readable signal media 1526 may be an electromagnetic signal, an optical signal, and/or any other suitable type of signal. These signals may be transmitted over communications links, such as wireless communications links, optical fiber cable, coaxial cable, a wire, and/or any other suitable type of communications link. In other words, the communications link and/or the connection may be physical or wireless in the illustrative examples.

In some illustrative embodiments, program code 1518 may be downloaded over a network to persistent storage 1508 from another device or data processing system through computer readable signal media 1526 for use within data processing system 1500. For instance, program code stored in a computer readable storage medium in a server data processing system may be downloaded over a network from the server to data processing system 1500. The data processing system providing program code 1518 may be a server computer, a client computer, or some other device capable of storing and transmitting program code 1518.

The different components illustrated for data processing system 1500 are not meant to provide architectural limitations to the manner in which different embodiments may be implemented. The different illustrative embodiments may be implemented in a data processing system including components in addition to or in place of those illustrated for data processing system 1500. Other components shown in FIG. 15 can be varied from the illustrative examples shown. The different embodiments may be implemented using any hardware device or system capable of running program code. As one example, the data processing system may include organic components integrated with inorganic components and/or may be comprised entirely of organic components excluding a human being. For example, a storage device may be comprised of an organic semiconductor.

In another illustrative example, processor unit 1504 may take the form of a hardware unit that has circuits that are manufactured or configured for a particular use. This type of hardware may perform operations without needing program code to be loaded into a memory from a storage device to be configured to perform the operations.

For example, when processor unit 1504 takes the form of a hardware unit, processor unit 1504 may be a circuit system, an application specific integrated circuit (ASIC), a programmable logic device, or some other suitable type of hardware configured to perform a number of operations. With a programmable logic device, the device is configured to perform the number of operations. The device may be reconfigured at a later time or may be permanently configured to perform the number of operations. Examples of programmable logic devices include, for example, a programmable logic array, programmable array logic, a field programmable logic array, a field programmable gate array, and other suitable hardware devices. With this type of implementation, program code 1518 may be omitted because the processes for the different embodiments are implemented in a hardware unit.

In still another illustrative example, processor unit 1504 may be implemented using a combination of processors found in computers and hardware units. Processor unit 1504 may have a number of hardware units and a number of processors that are configured to run program code 1518. With this depicted example, some of the processes may be implemented in the number of hardware units, while other processes may be implemented in the number of processors.

As another example, a storage device in data processing system 1500 is any hardware apparatus that may store data. Memory 1506, persistent storage 1508, and computer readable media 1520 are examples of storage devices in a tangible form.

In another example, a bus system may be used to implement communications fabric 1502 and may be comprised of one or more buses, such as a system bus or an input/output bus. Of course, the bus system may be implemented using any suitable type of architecture that provides for a transfer of data between different components or devices attached to the bus system. Additionally, a communications unit may include one or more devices used to transmit and receive data, such as a modem or a network adapter. Further, a memory may be, for example, memory 1506, or a cache, such as found in an interface and memory controller hub that may be present in communications fabric 1502.

Data processing system 1500 may also include associative memory 1528. Associative memory 1528 may be associative memory 104 of FIG. 1, associative memory 700 of FIG. 1, analysis application 1308 of FIG. 13, associative memory 1408 of FIG. 14, or other associative memories described elsewhere herein, and may have the properties described elsewhere herein. Associative memory 1528 may be in communication with communications fabric 1502. Associative memory 1528 may also be in communication with, or in some illustrative embodiments, be considered part of storage devices 1516. While one associative memory 1528 is shown, additional associative memories may be present.

As used herein, the term "associative memory" refers to a plurality of data and a plurality of associations among the plurality of data. The plurality of data and the plurality of associations may be stored in a non-transitory computer readable storage medium. The plurality of data may be collected into associated groups. The associative memory may be configured to be queried based on at least indirect relationships among the plurality of data in addition to direct correlations among the plurality of data. Thus, an associative memory may be configured to be queried based solely on direct relationships, based solely on at least indirect relationships, as well as based on combinations of direct and at least indirect relationships. An associative memory may be a content addressable memory.

Thus, an associative memory may be characterized as a plurality of data and a plurality of associations among the plurality of data. The plurality of data may be collected into associated groups. Further, the associative memory may be configured to be queried based on at least one relationship, selected from a group that includes direct and at least indirect relationships, or from among the plurality of data in addition to direct correlations among the plurality of data. An associative memory may also take the form of software. Thus, an associative memory also may be considered a process by which information is collected into associated groups in the interest of gaining new insight based on relationships rather than direct correlation. An associative memory may also take the form of hardware, such as specialized processors or a field programmable gate array.

As used herein, the term "entity" refers to an object that has a distinct, separate existence, though such existence need not be a material existence. Thus, abstractions and legal constructs may be regarded as entities. As used herein, an entity need not be animate. Associative memories work with entities.

Figure 16:
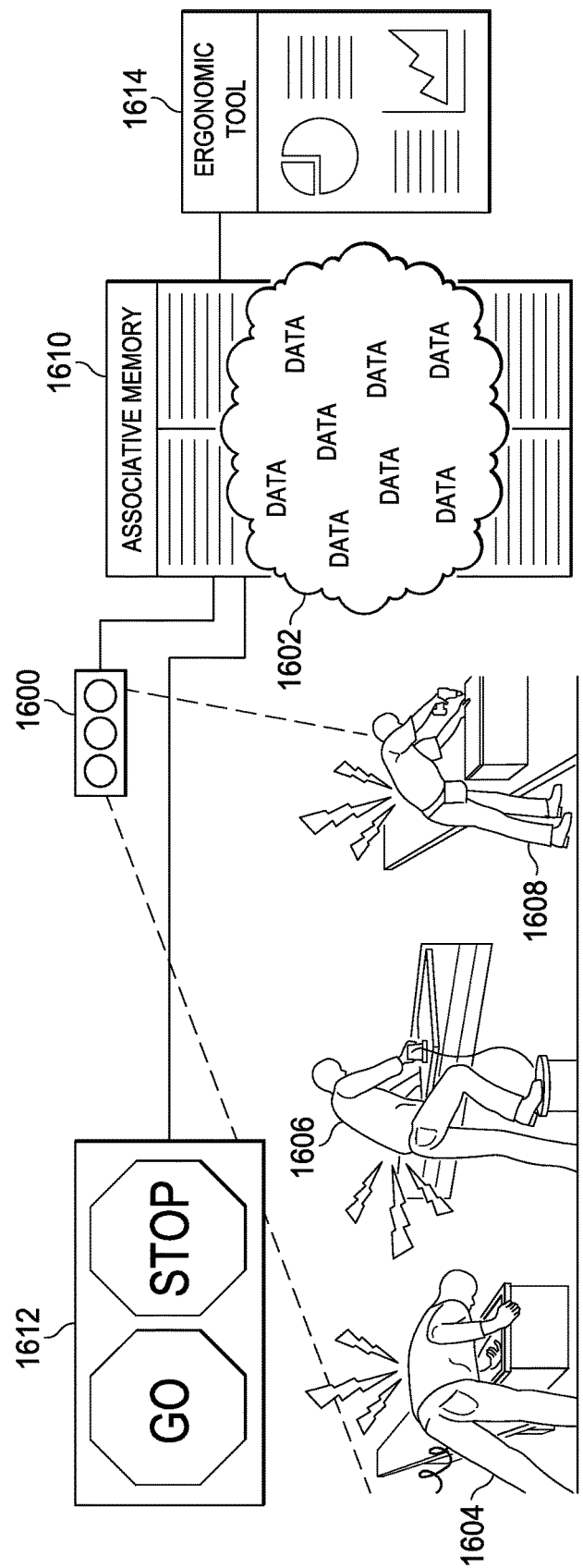
FIG. 16 illustrates a summary procedure for performing ergonomic analysis, in accordance with an illustrative embodiment.

FIG. 16 illustrates a summary procedure for performing ergonomic analysis, in accordance with an illustrative embodiment. An ergonomic analysis may be performed using an associative memory, such as associative memory 1528 of FIG. 15.

The word "Ergonomics" comes from two Greek words "ergon", meaning work, and "nomos" meaning laws. Today, the word is generally used to describe the science of designing the job to fit the worker, not forcing the worker to fit the job. The goal of ergonomics is to improve working conditions and improve worker health. Ergonomic research and development focuses on the work environment and items such as the design and function of workstations, controls, displays, safety devices, tools and lighting to fit the employee's physical requirements, capabilities, and limitations to ensure his or her health and well-being. Ergonomic research and development may also include training the user to correctly position or reposition the user's body to reduce stressors that cause musculoskeletal disorders (MSDs).

As used herein, the terms "ergonomic issue data" or "ergonomic issue" refer to one or more of: evaluating a movement for the desirability or undesirability of the movement from an ergonomic perspective, taking data to evaluate the ergonomics of one or more movements, identifying a type of motion for ergonomic evaluation, or ergonomic questions related to either an individual or a group of individuals or a comparison thereof. Current ergonomic issue data is collected by having one or more persons observe tasks being performed by other persons. Body joint angles are estimated and collected over the length of time it takes to complete the desired tasks.

However, accurate measurements are difficult to make while the person is continually moving. Often the observer is distracted by other activities occurring in the same vicinity. Further, it is difficult to record and accumulate all desirable information in the amount of time the subject is in a less desirable posture. This fact may be an important factor in an ergonomic evaluation. Thus, the resulting data collection may be subjective, not as accurate as desired, and possibly inconsistent across evaluations performed by different evaluators.

Evaluation tools used to address ergonomics in industrial settings are cumbersome, costly and not always effective. A common inadequacy among them is their inability to capture or transfer "live" movements of an individual into a tool or ergonomic device. This task is further complicated if the movement being captured is complex or constantly changing; as is the case with most industrial work.

With concerns to ergonomic analysis, especially within factory-like settings, it is generally most effective to evaluate each issue on a case-by-case basis, because each case has its own unique underlying challenges. As a result, solutions should be both flexible and rigid: Flexible enough to address each individual case while, at the same time, rigid enough to provide useful results.

The illustrative embodiments use motion sensor input device 1600 to collect data 1602 on movements of one or more persons, such as person 1604, person 1606, or person 1608. Motion sensor input device 1600 may be an apparatus used to detect the change in position of an object relative to its surroundings or the change in the surroundings relative to an object.

Then the movements may be fed into associative memory 1610 in order to interpret them. Associative memories are defined above, but briefly again associative memory technology is the process by which information is collected into associated groups in the interest of gaining new insight based on relationships rather than direct correlation. Associative memory 1610 uses pre-recorded ergonomic positions to which to compare the detected movements. As a result, the illustrative embodiments are able to distinguish complicated movements and provide output information 1612 regarding these complicated movements directly to the users or into ergonomic tool 1614. Ergonomic tool 1614 may be an off-the-shelf ergonomic tool in some illustrative embodiments, or may be part of the illustrative embodiments in the form of programming for the associative memory, the CPU device, or other parts of a computer.

The illustrative embodiments are a unique use of a motion sensing input device to capture complex ergonomic movements in unforgiving environments and interpret those movements using an associative memory already trained with predefined ergonomic postures. The illustrative embodiments could be used as an input device for an ergonomic tool or the illustrative embodiments could be used independently to directly notify a user in real time. "Real time" is a time interval that is short compared to time intervals over which a given action is typically taken.

One of several distinguishing features of the illustrative embodiments is the illustrative embodiment's use of memories of ergonomic movements to train associative memory 1610. When evaluating live movements, associative memory 1610 compares the live movements with the trained movements in order to properly identify the new movements. This process is considerably computationally easier than manually measuring the movements quantitatively and using the measurements to calculate positions and movements.

As a result, the illustrative embodiments provide a timely, accurate and cost-effective way of collecting ergonomic data and interpreting it. Furthermore, the illustrative embodiments have other advantages over the known art. For example, the illustrative embodiments may operate in a clandestine fashion, being invisible to the participant being observed, though preferably the user should know in a general sense he or she is being observed. However, the non-invasive nature of the illustrative embodiments increases user comfort.

In addition, the illustrative embodiments make use of inexpensive hardware and centralized software. The illustrative embodiments are extremely flexible and could be trained to recognize many different ergonomic postures. The input mechanisms the illustrative embodiments use can be updated, changed, or improved as desired inexpensively and without changing other components of the system. Thus, the illustrative embodiments may replace older and more cumbersome techniques of performing ergonomic analysis.

Yet further, the illustrative embodiments do not require an onsite ergonomic expert, thereby reducing costs. The illustrative embodiments may be language independent and not restricted to just English applications. The illustrative embodiments are subject matter independent with respects to ergonomics and are universally deployable. Additional advantages and uses are possible.

Figure 17:
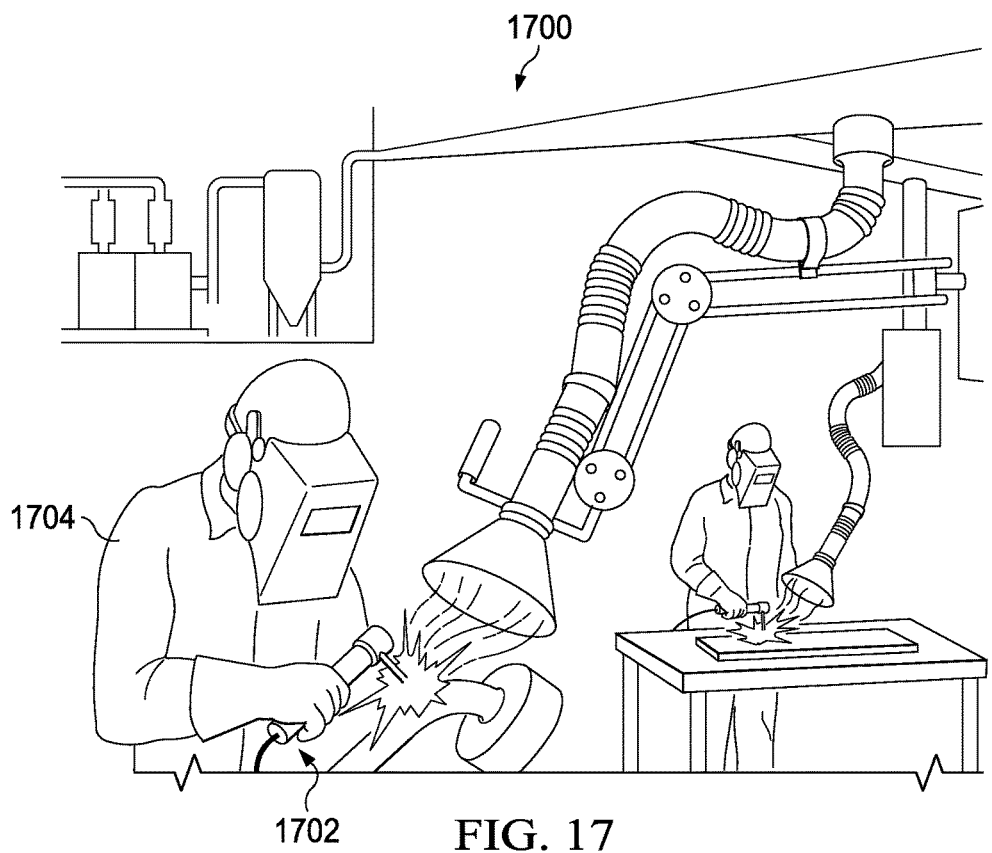
FIG. 17 illustrates an example of a difficult environment in which to perform an ergonomic analysis, in accordance with an illustrative embodiment.

FIG. 17 illustrates an example of a difficult environment in which to perform an ergonomic analysis, in accordance with an illustrative embodiment. Environment 1700 is an example of a difficult environment in which to perform an ergonomic analysis. The methods and devices shown with respect to FIG. 16 also may be used with respect to environment 1700 of FIG. 17.

Environment 1700 represents a factory-like environment. Carrying out an ergonomic analysis in a factory-like environment is difficult. Complicated movements, the number of different movements performed, along with physical obstacles, can make an accurate ergonomic analysis very difficult.

Ergonomic analysis within an industrial setting, such as environment 1700, is nothing like the ergonomic analysis typically performed within offices. The movements made in factories usually involve the entire body, where it can be required to twist and turn in many directions. Furthermore, movements in environment 1700 can occur at different angles, slopes and planes. Still further, unlike an office setting, workers within a factory are usually not stationary, but instead may move from place to place.

An ergonomic analysis can be further complicated within a factory by industrial objects. Production tools and assembly devices in environment 1700 may become natural obstructions when trying to evaluate issues with someone's ergonomic position. Typically, these obstacles cannot be moved. Furthermore, hazardous materials or other environmental factors could also impede an evaluation. For example, as seen in area 1702, a user's wrist position may be obscured by tools, gloves, or factory equipment. However, the wrist position may be of interest when performing an ergonomic analysis of person 1704.

Figure 18:
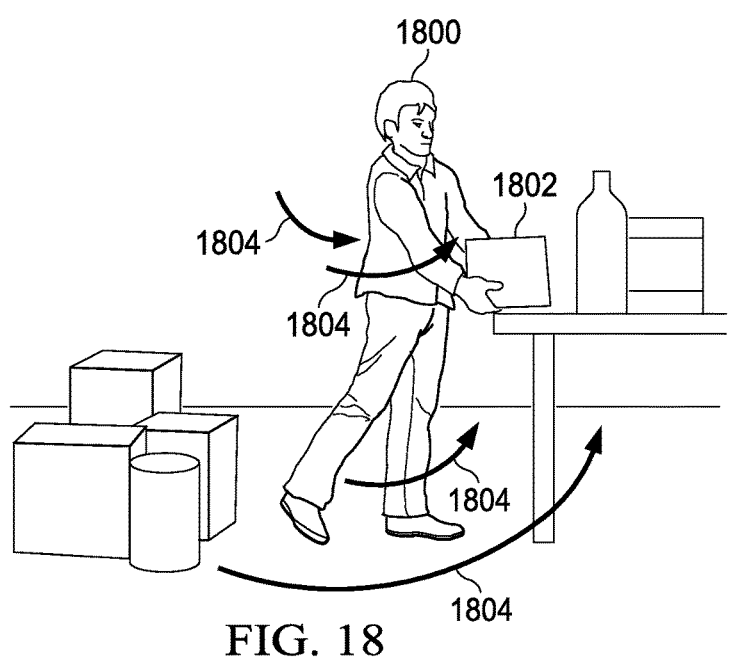
FIG. 18 illustrates an example of lift and carry ergonomic issues, in accordance with an illustrative embodiment.

FIG. 18 illustrates an example of lift and carry ergonomic issues, in accordance with an illustrative embodiment. FIG. 18 is an example of an activity that may be ergonomically evaluated as described with respect to FIG. 16, or may be an activity performed in a difficult environment, such as environment 1700 of FIG. 17.

Ergonomic evaluation evaluates or estimates the possibility of exposure to undesirable outcomes to person 1800 brought on by incorrect or less than desirable movements. In this particular example, the focus of ergonomic evaluation is on correctly repositioning the person's body, actions, and movements in order to reduce levels of physical stress.

FIG. 18 shows person 1800 lifting object 1802 and twisting the person's body at the same time, as indicated by arrows 1804. This action can increase the possibility of back strain for person 1800. To decrease this possibility, person 1800 should place their feet in a walking position with one foot pointing slightly in the direction of the lift. Then, person 1800 may lift object 1802 and shift the weight of the body onto the foot in the turning direction.

Ergonomic factors such as these can be difficult to detect and usually require experts to diagnose. However, such ergonomic factors can involve all aspects of a job, from the physical stresses placed on joints, muscles, nerves, tendons, bones and the like, to environmental factors which can affect hearing, vision, general comfort, and health. In general, increasing ergonomic welfare within a workplace creates a more efficient and safer environment. In turn, a more efficient and safer environment may results in higher productivity.

Figure 19:
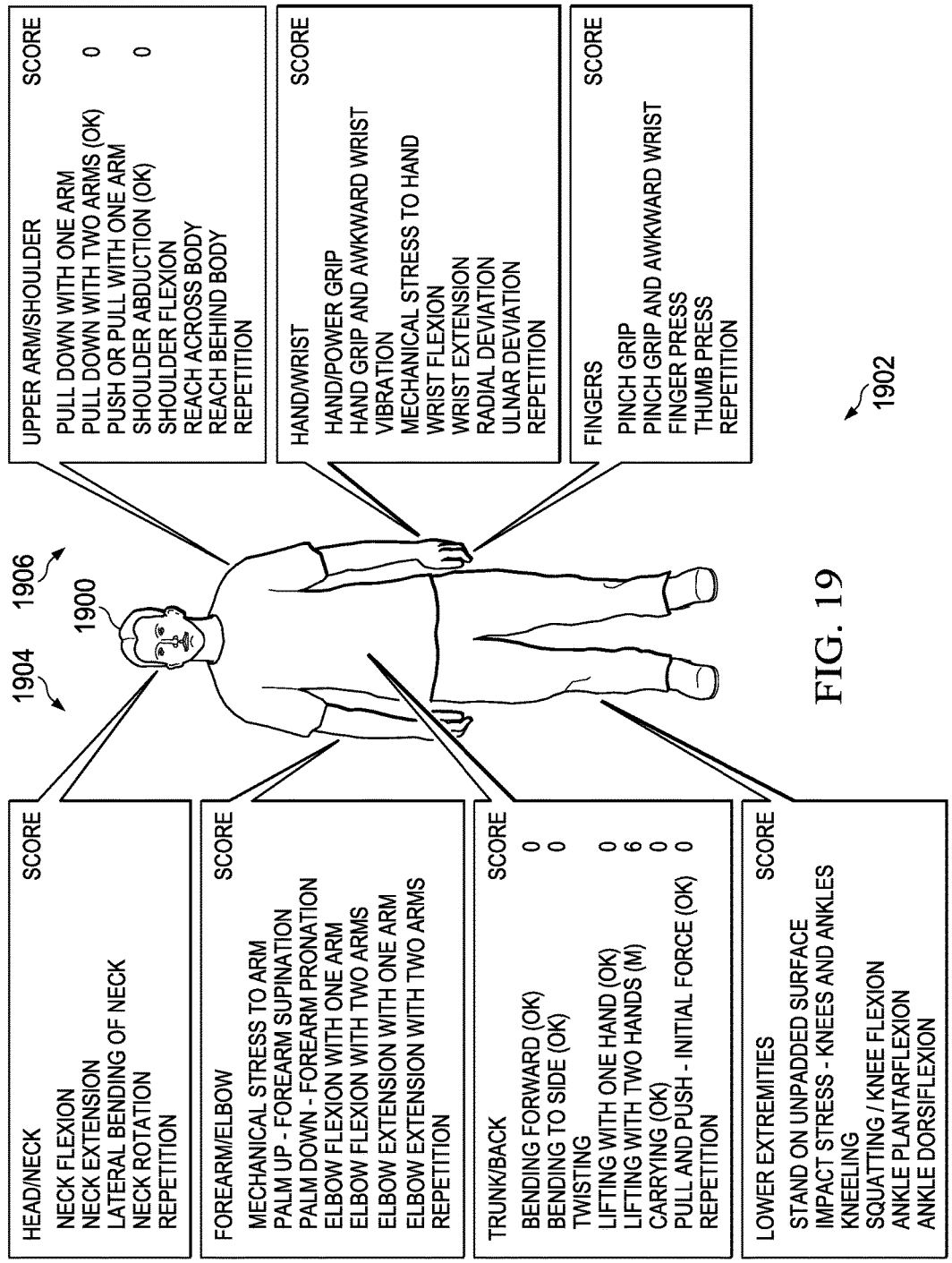
FIG. 19 illustrates an example of an ergonomic checklist, in accordance with an illustrative embodiment.

FIG. 19 illustrates an example of an ergonomic checklist, in accordance with an illustrative embodiment. The illustration of person 1900 may be, for example, persons 1604, 1606, and 1608 of FIG. 16, person 1704 of FIG. 17, or person 1800 of FIG. 18. Checklist 1902, which includes both sets of items shown generally at right side 1904 and left side 1906 of person 1900, may be used with respect to an ergonomic evaluation, as described with respect to FIG. 16 through FIG. 18.

Ergonomic analysis tools help identify factors in ergonomic evaluations. Ergonomic analysis tools may also address specific body parts and the corresponding work they do. Each area of interest may be carefully examined as it pertains to a particular job. The resulting ergonomic evaluation usually creates a more productive and safer environment. However, even the most advanced ergonomic tools are limited by their ability to collect external data. The challenge is describing the position of a body in a manner which an ergonomic tool can understand. To accomplish this goal, it is possible to use a checklist, like the one shown in FIG. 19.

Another possibility is to use a motion sensor, coupled with an associative memory, as described herein. As explained above, the illustrative embodiments can provide an excellent input device for an ergonomic analysis tool. The illustrative embodiments can describe an individual's position or positions by classifying a given movement against other pre-recorded positions in order to determine the movement.

Figure 20:
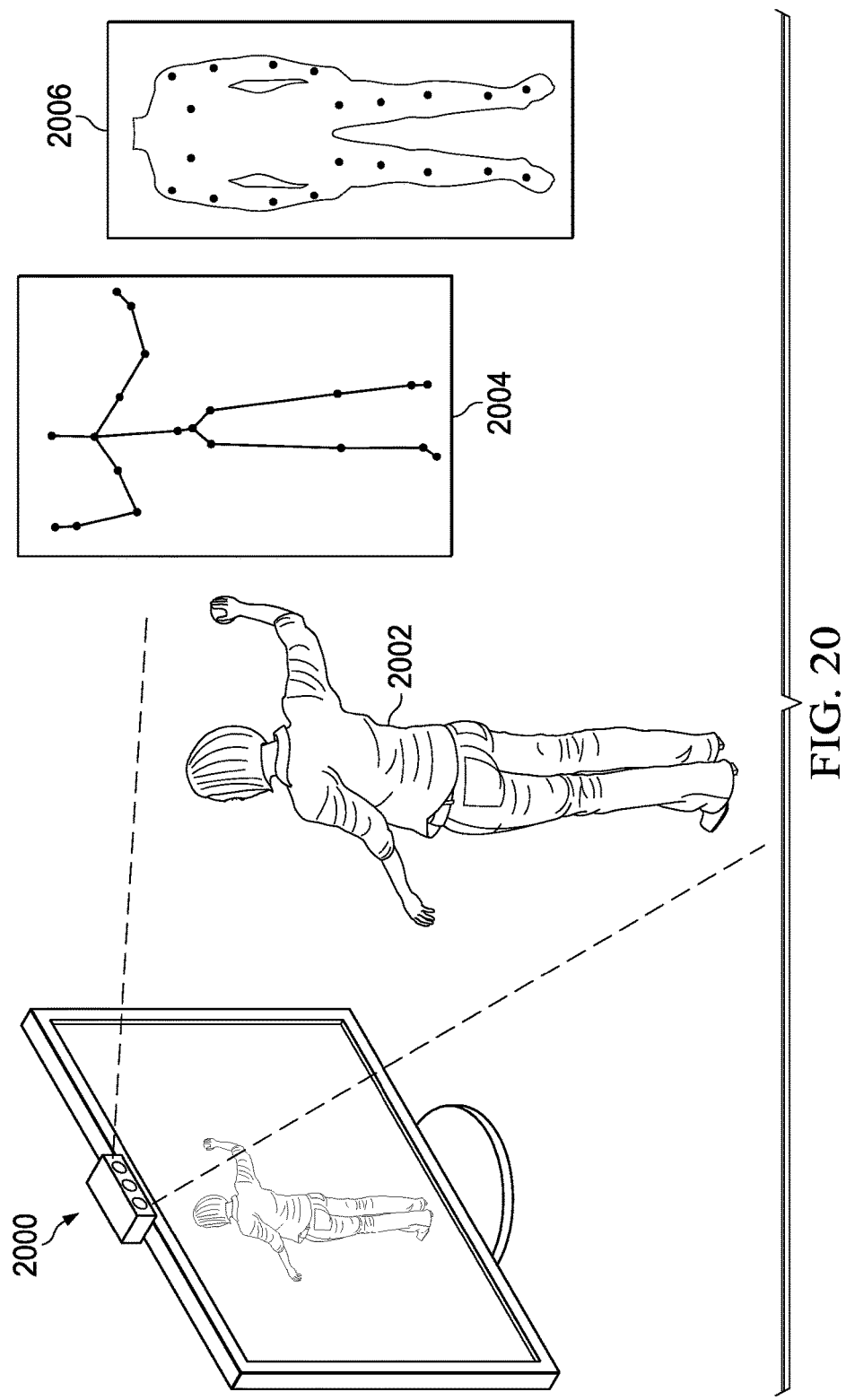
FIG. 20 illustrates an example of a motion sensing input device, in accordance with an illustrative embodiment.

FIG. 20 illustrates an example of a motion sensing input device, in accordance with an illustrative embodiment. Motion sensor input device 2000 may be used with respect to performing ergonomic analysis using an associative memory, as described with respect to FIG. 16 through FIG. 19. Motion sensor input device 2000 may be another example of kinematic detection system 300 of FIG. 3, motion sensor 902 of FIG. 9, motion sensor 1302 of FIG. 13, or kinematic measurement device 1402 of FIG. 14.

The illustrative embodiments may use motion sensor input device 2000 to identify a person's movements, such as the movements of person 2002, who instead could be an object or a robot if the illustrative embodiments call for evaluating the ergonomics of an object or robot. In any case, motion sensor input device 2000 may be used to detect a change in position of person 2002 relative to his or her surroundings, indicated generally at corresponding stick person 2004. Although potentially capable of doing much more, only the motion sensing functionality of this device is needed for some of the illustrative embodiments.

In an illustrative embodiment, motion sensor input device 2000 may include or be connected to software which provides the X-Y or X-Y-Z coordinates of where the movement took place. The motions of certain points could take the form of evaluating points of motion on a corresponding stick person 2004, though these motions may be tracked using non-visual means as described further below. In either case, the illustrative embodiments contemplate using these coordinates to calculate the subject's movements.

To gauge the subject's movements, the invention correlates the coordinates of a position shared by all parties, that is to say it compares hand movements to hand movements. The measurements can be further normalized if needed. The invention could use the distance between parts of the body which are relatively static; such as the center hip to the spine, to normalize the rest of the measurements.

Note that motion sensor input device 2000 is not necessarily limited to a single remote sensor. Motion sensor input device 2000 may take many forms. For example, motion sensor input device 2000 could also take the form of multiple sensors, perhaps in a suit or on clothes, as shown generally at a sensor suit 2006. Motion sensor input device 2000 need not use all sensors for a given application. For example, stored or taken data may be limited to only certain sensors of sensor suit 2006, such as when motions of only a specific part or parts of a person's body are to be captured. Likewise, a camera or other remote sensor could record data only for a certain part or parts of a person's body. A combination of sensor suit 2006, a camera, and/or some other motion sensor could be used in the illustrative embodiments. Motion sensor input device 2000 may also take other forms, and thus the devices shown in FIG. 20 do not necessarily limit the claimed inventions.

Figure 21:
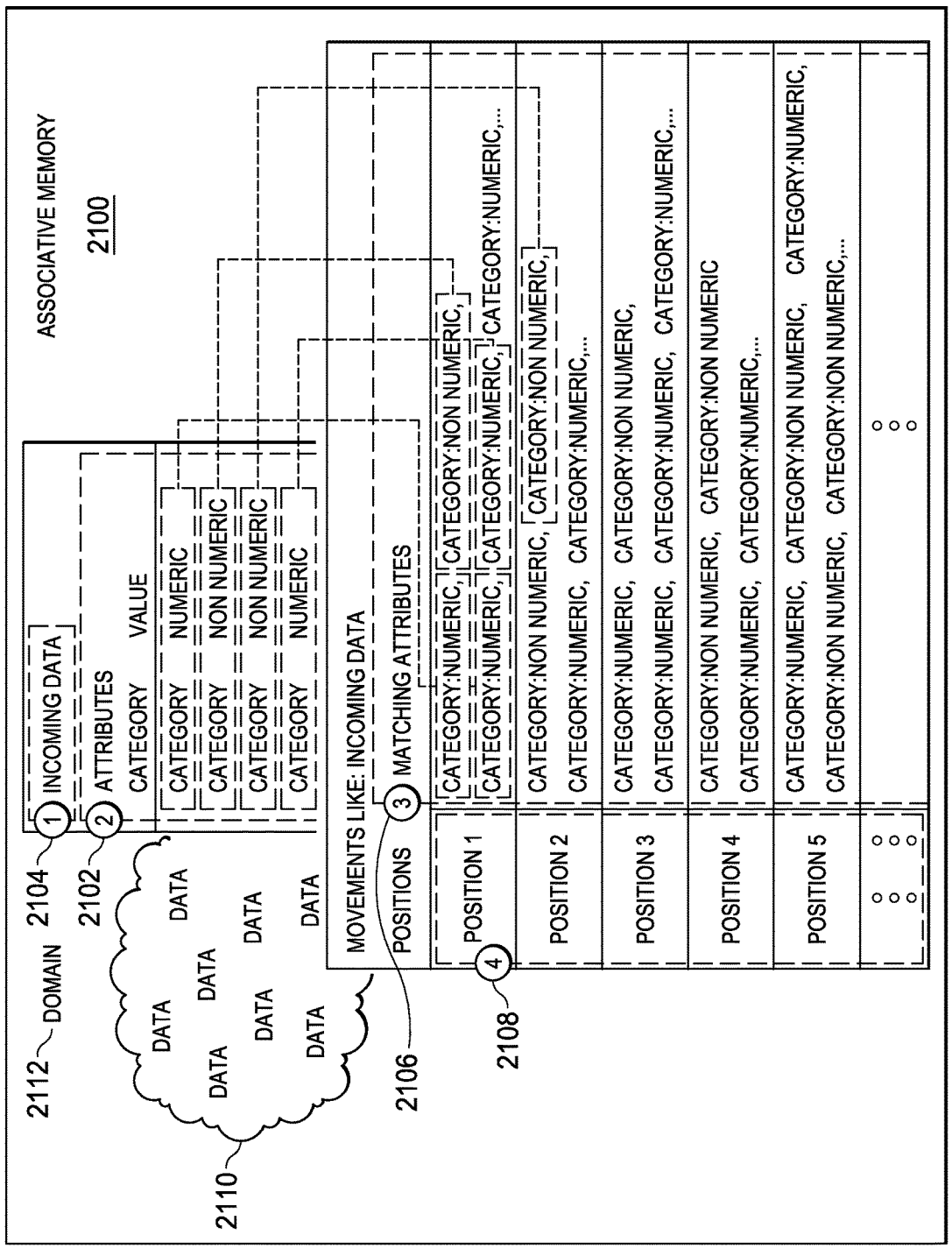
FIG. 21 illustrates an example of matching attributes in an associative memory, in accordance with an illustrative embodiment.

FIG. 21 illustrates an example of matching attributes in an associative memory, in accordance with an illustrative embodiment. Associative memory 2100 may be, for example, associative memory 1610 in FIG. 16, associative memory 1528 of FIG. 15, or other associative memories described herein. Associative memory 2100 may include data 2110 within domain 2112.

The illustrative embodiments collect the measured attributes by translating the coordinates supplied by the motion sensor into a verbiage best suited for the associative memory. In turn, the associative memory may compare measured attributes 2102 (circle 2) of incoming data 2104 (circle 1) to matching attributes 2106 (circle 3) of pre-recorded ergonomic positions, shown generally at 2108 (circle 4). The purpose of the comparison is to determine whether if measured attributes 2102 are similar to matching attributes 2106, which have been pre-determined or pre-recorded as being associated with one or more particular positions. If these groups of attributes are similar to each other, then it may be inferred that measured attributes 2102 correspond to a pre-determined movement which also corresponds to matching attributes 2106. Stated differently, if these groups of attributes are similar to each other, then it can be inferred that the measured movement is the same as or similar to the pre-determined movement.

One of several purposes of the illustrative embodiments is to provide a timely, accurate, and cost-effective method of collecting and interpreting ergonomic data 2110, so the ergonomic data can be displayed directly to a user or fed into an ergonomic analysis tool. Another of several purposes of the illustrative embodiments is to handle complex movements in difficult environments, such as environment 1700 of FIG. 17. Yet another of several purposes of the illustrative embodiments is to perform all of the above processing within real-time. As used herein, "real time" means time spans that are short compared to the actions being taken.

Again, the illustrative embodiments evaluate ergonomic factors and may make ergonomic determinations by using an associative memory to interpret movements typically gathered by a motion sensor device, camera, or a sensor suit. The movement data may be tested by an associative memory classification function to determine if the data matches any pre-recorded ergonomic positions. A match occurs only when the incoming data's attributes equal the attributes of the pre-recorded ergonomic positions. In some illustrative embodiments, an approximate match may be sufficient for a match. Therefore, the number of matches strengthens the result.

While associative memory 2100 may be used as the ergonomic evaluation tool itself, in one aspect of the illustrative embodiments, associative memory 2100 is used only for making a determination regarding classifying a person's movements or object's movements. In this case the associative memory may provide either the classifications or the measurements (or both) to a separate ergonomic tool. Thus, the illustrative embodiments do not necessarily directly define the interface to any particular ergonomic tool. Instead, the illustrative embodiments may provide a method of transferring information.

The illustrative embodiments include the ability to detect movements of a person or object by using an interface to a motion sensing input device. This interface can vary in scope and functionality, but preserves the job of defining the coordinates of a movement in whatever capacity the motion sensing input device can handle. Thus, the illustrative embodiments do not necessarily limit the means used to collect movement information or other information useful to an ergonomic evaluation.

The illustrative embodiments do not necessarily limit the number of people the invention can evaluate with concerns to said position. Thus, while one individual has been shown in FIG. 16 through FIG. 20, the illustrative embodiments contemplate simultaneously evaluating the movements of multiple people.

The illustrative embodiments specifically contemplate ergonomic analysis for difficult environments, such as factory-like settings. However, the illustrative embodiments could be used anywhere there are potential ergonomic issues.

Figure 22:
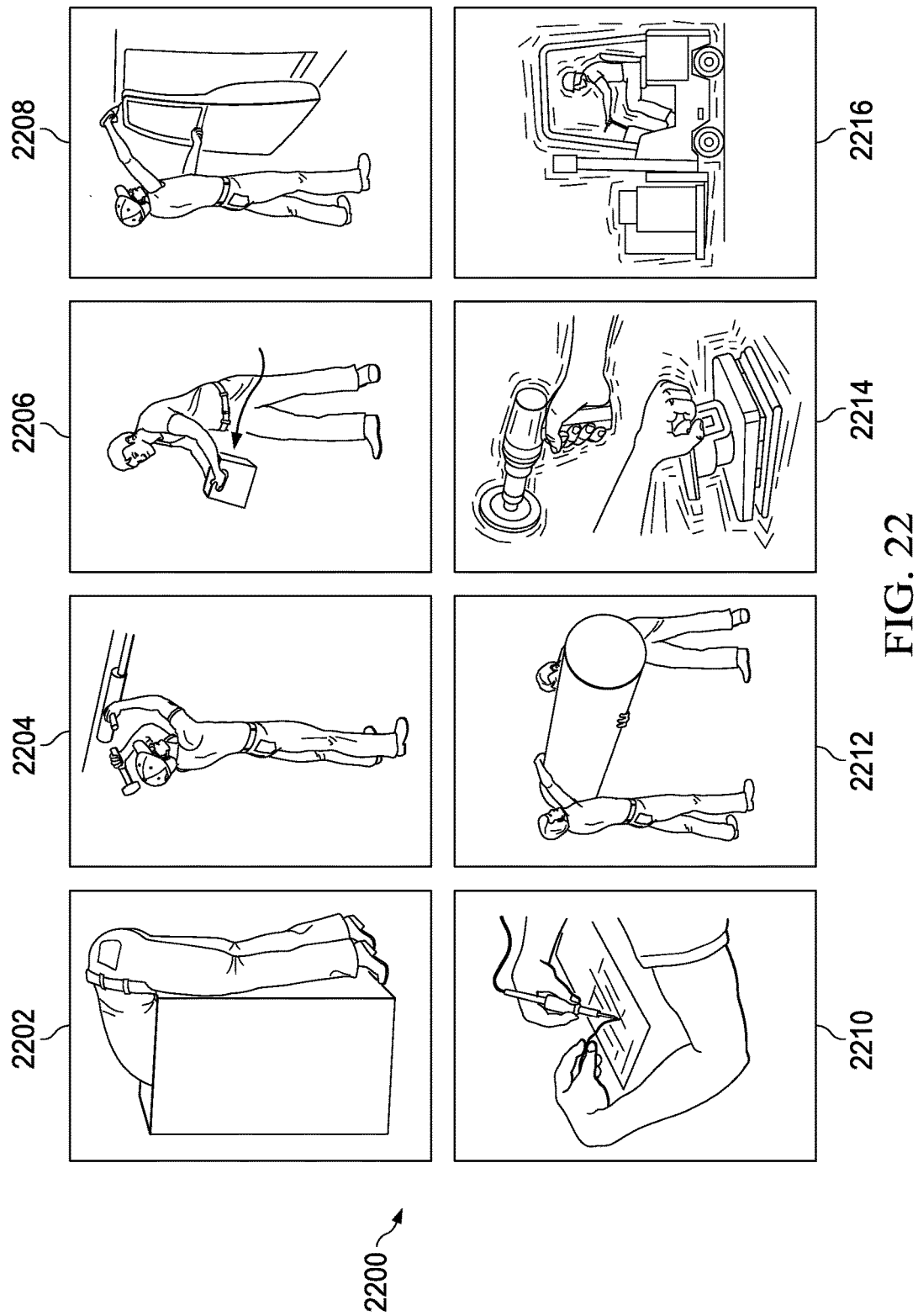
FIG. 22 illustrates examples of some labels used to identify ergonomic issues, in accordance with an illustrative embodiment.

FIG. 22 illustrates examples of some labels used to identify ergonomic issues, in accordance with an illustrative embodiment. The various postures shown in FIG. 22 may be identified using any of the methods and systems described with respect to FIG. 16 through FIG. 21.

FIG. 22 identifies eight typical ergonomic issues that may be addressed using a combination of the illustrative embodiments (to identify the ergonomic issues) with re-tooling or personnel training to mitigate any undesirable ergonomic issues. In a factory setting, such as environment 1700 of FIG. 17, common ergonomic issues 2200 include awkward postures 2202 (such as bending over without bending the knees), overhead work 2204 (which may include extended reaching), twisting and carrying loads (2206), poor shoulder or wrist position (2208), wrist deviations (2210), lifting bulky loads (2212), hand-arm vibration (2214), and whole body vibration (2216). Many other ergonomic issues exist, such as but not limited to typing, body posture at a desk, etc.

With respect to the illustrative embodiments, initially, a subject matter expert may determine which movements have the greatest likelihood for undesirable ergonomic issues at a particular work site. Once identified, these movements may be captured by an associative memory in order to train it, as described above. When trained, the associative memory will be able to recognize new (observed) movements by comparing them to how the associative memory was trained, as described above.

To train the system, an individual may demonstrate a movement, which the system captures. The movement, itself, could be captured by a motion sensor camera or a by an individual wearing a sensor suit. Either mechanism should provide the invention with enough information about the movement to accurately classify it. Other capture mechanisms are also possible.

Typically, a movement is recorded from the input sensor into a storage device. Then, the data from the input sensor is ingested into the associative memory to form the foundation of the training. As part of this process, each movement may associate itself with a label that identifies the movement with particular ergonomic issue; such as "awkward postures" 2202, "overhead work" 2204, or others, as shown in FIG. 22.

When completed, the associative memory has repository of ergonomic positions that it can use to identify new (observed) movements, when introduced. These pre-recorded or pre-determined positions represent truth data used to "train" the classification system.

Because the illustrative embodiments may capture the positions as a series of movements, the underlying classification is more flexible. This flexibility allows a match to occur at any point during the movement in order to conclude that the individual was in fact performing a given movement. As a result, the illustrative embodiments place the emphasis of measurement on the mechanics of the movement, rather than its nuances.

Figure 23:
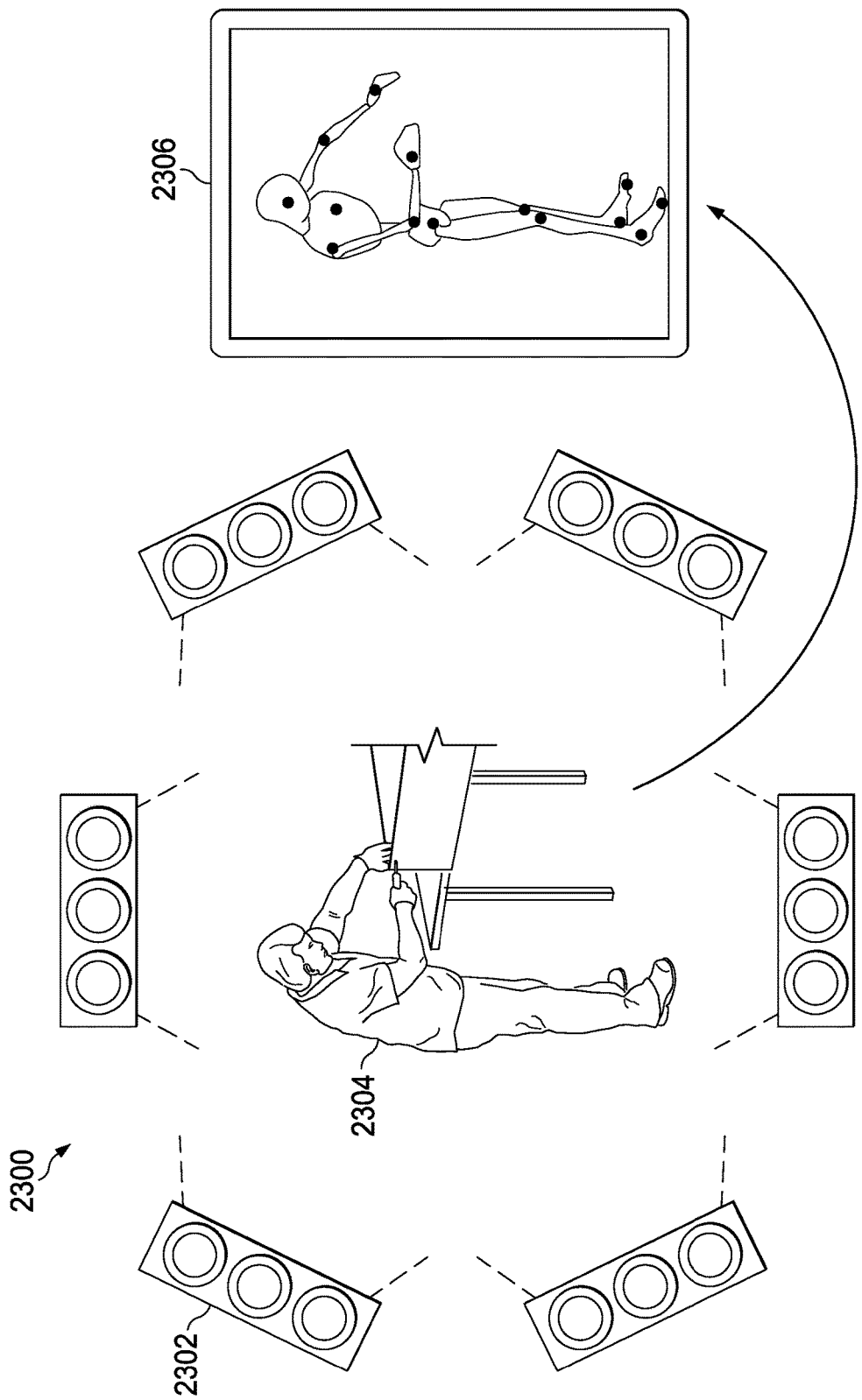
FIG. 23 illustrates an example of ergonomic analysis using motion capture, in accordance with an illustrative embodiment.

FIG. 23 illustrates an example of ergonomic analysis using motion capture, in accordance with an illustrative embodiment. Motion capture system 2300 may be, for example, motion sensor input device 2000 of FIG. 20.

Once the training of the associative memory is complete, as described above, ergonomic analysis is ready to be performed. One or more motion sensors, 2302, are set up in the area of intended use. Then, the sensors capture the movements and/or positions of individual 2304. The captured motions and/or positions may be displayed on a computer system, or otherwise recorded, as shown at display 2306. At this point, the associative memory evaluates the observation captured by the one or more motions sensors 2302 to determine if the observation is, in fact, ergonomically correct.

Optionally, an alert may be generated to alert the user or some other person, or possibly software, if the observation represents an ergonomically incorrect or undesirable movement or position. This alert could take many forms, such as but not limited to an audio alert, a visual alert, or a written report.

Figure 24:
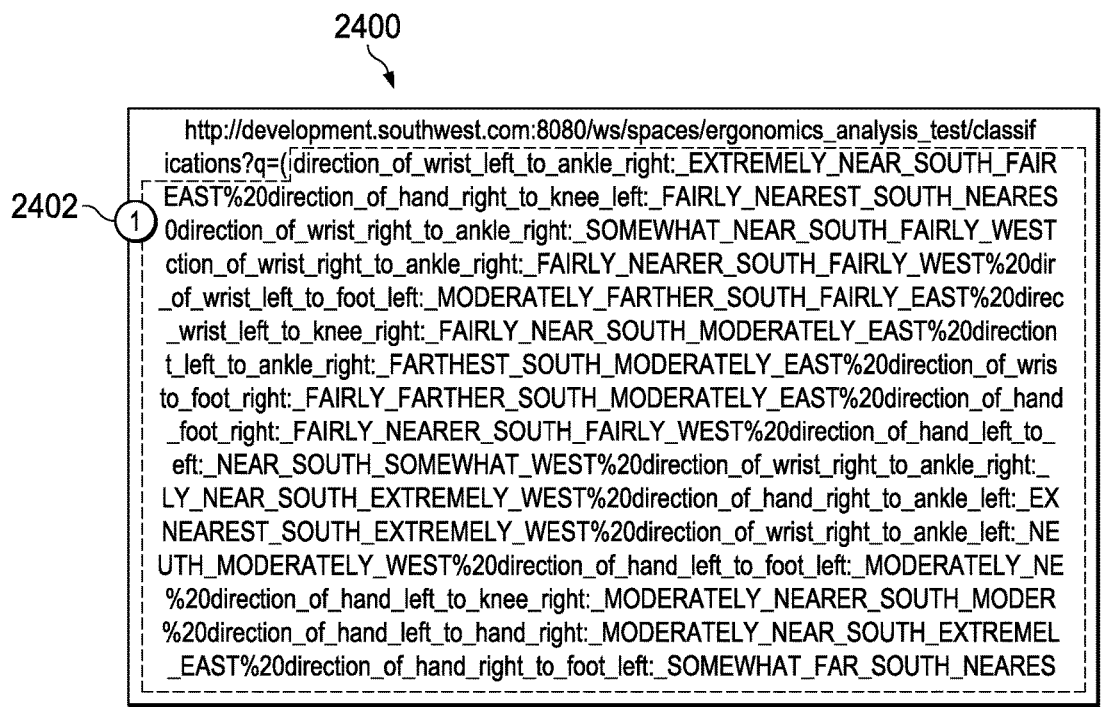
FIG. 24 illustrates an example of a classification call by an associative memory, in accordance with an illustrative embodiment.

FIG. 24 illustrates an example of a classification call by an associative memory, in accordance with an illustrative embodiment. FIG. 24 represents a classification call performed by an associative memory when identifying a new observed movement (such as classification based on data received from a motion sensor capture system), as described above with respect to FIG. 16 through FIG. 23.

In an illustrative embodiment, each new observation provides the associative memory with a set coordinates, typically located at points of articulation on the person observed. This information is transformed into a word-like verbiage and is used to build the foundation of the classification call. The coordinates themselves can also be further manipulated to give the call more relevance. For example, locations, distances, and directions could be calculated from these coordinates to provide greater detail.

Using the manipulated coordinates, the associative memory constructs a classification call. The syntax of this call can vary depending on the underlying rules of the particular classification system used. FIG. 24 specifically shows an example of an associative memory classification call. Associative memory classification call 2400 contains attributes, shown in box 2402 shown generally at circle 1, collected from the information described above.

The results of this call may determine which of the training set or sets the new observation most closely resembles. Using this information, the associative memory can conclude what position or motion was captured. Yet further, in some cases, the associative memory may also determine whether the position or motion was ergonomically correct or ergonomically undesirable.

Furthermore, the results could be fed from the associative memory into an ergonomic analysis tool or other hardware or software as input. Such input may allow the ergonomic analysis tool to decide the correctness of the position captured. Thus, the associative memory itself may or may not perform the ergonomic analysis, but in some cases may only be a device for providing input to other ergonomic tools.

Note that some of the terms in associative memory classification call are not limited to single words, but may also be phrases. Typically, entity values are single words, but an associative memory can be configured to handle phrases through the use of name lists or character substitutions, such as by replacing a space with an underscore.

Figure 25:
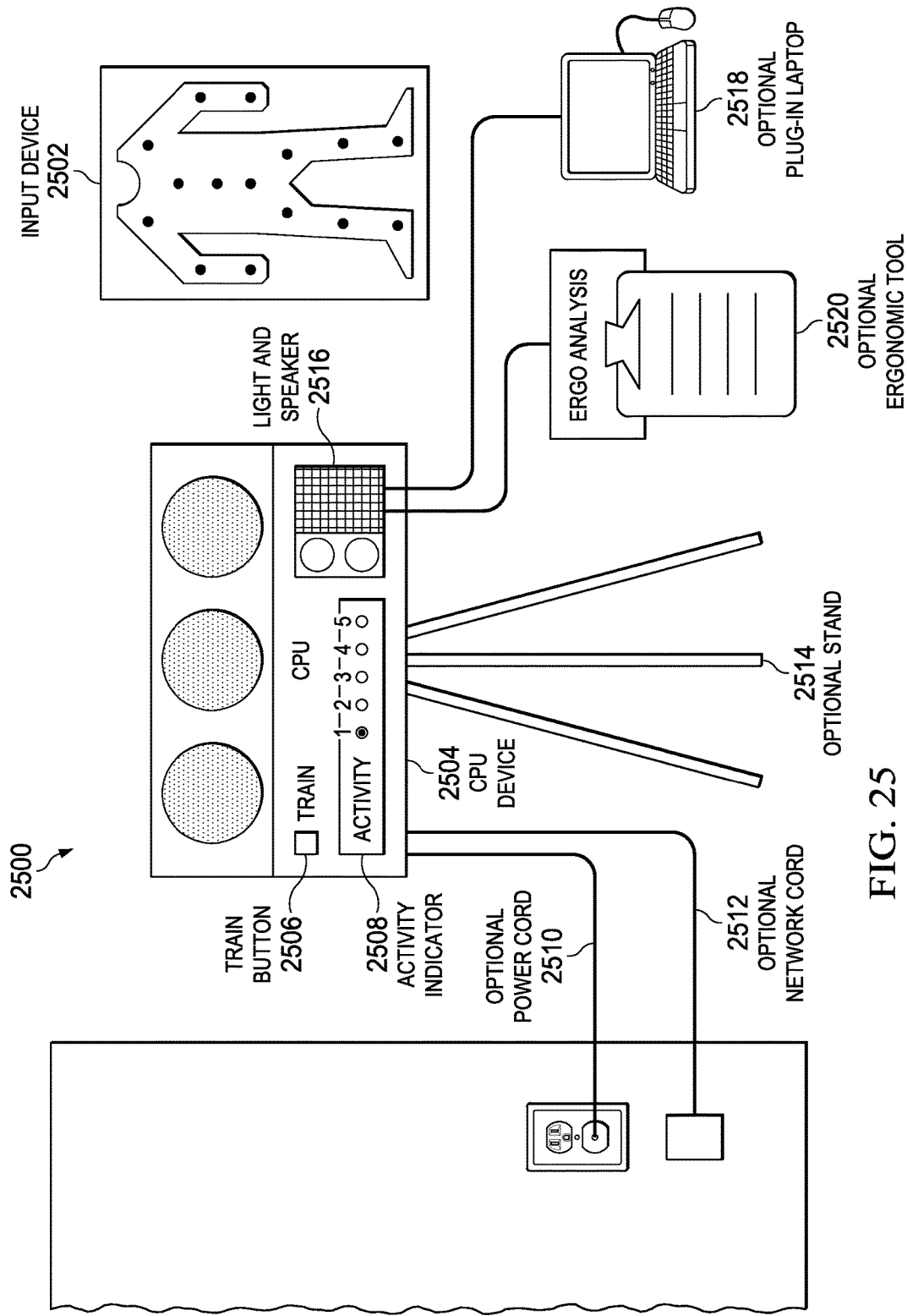
FIG. 25 illustrates one possible physical embodiment of the illustrative embodiments, in accordance with an illustrative embodiment.

FIG. 25 illustrates one possible physical embodiment of the illustrative embodiments, in accordance with an illustrative embodiment. FIG. 25 is an alternative embodiment to kinematic detection system 900 shown in FIG. 9. Ergonomic evaluation system 2500 has been designed specifically for the ergonomic evaluation techniques described with respect to FIG. 16 through FIG. 24. Ergonomic evaluation system 2500 is exemplary only; other ergonomic evaluation systems and hardware are possible. For example, in some cases, the associative memory itself can perform the ergonomic analysis, as described above.

Ergonomic evaluation system 2500 may use either a motion sensor camera or a sensor suit as input device 2502 to connect to a CPU device 2504 containing or executing the associative memory. "CPU" stands for "central processing unit," but may also refer to a computer generally. CPU device 2504 may have train button 2506 used to switch to "training" mode. In an illustrative embodiment, activity indicator 2508 may allow the user to select a selection of one or more pre-recorded ergonomic positions.

Ergonomic evaluation system 2500 may include optional power cord 2510 or a battery. Ergonomic evaluation system 2500 may also include optional network cord 2512 or a wireless device connecting it to a network. In this manner an associative memory, database, or any other system credentials could be accessed remotely. However, it is possible to place all desirable software for the illustrative embodiments within CPU device 2504 itself.

Ergonomic evaluation system 2500 may include optional stand 2514 or be placed somewhere else secure. Ergonomic evaluation system 2500 may include light and speaker 2516 used to indicate the detection of ergonomic movements or as an alarm or alert to a user. In some illustrative embodiments only a light or only a speaker may be present. In other illustrative embodiments, neither is present and the measured movements are either recorded or sent to optional ergonomic tool 2520.

Optionally, optional plug-in laptop 2518 could be used to help configure, update, or optimize the invention. Optional plug-in laptop 2518 may be replaced with a desktop computer, a tablet computer, or any other desirable computing device. As indicated above, ergonomic evaluation system 2500 may include optional ergonomic tool 2520, which performs ergonomic evaluations of motions or positions captured by input device 2502 and classified by the associative memory of CPU device 2504.

FIG. 26 illustrates an example of an entity comparison using an associative memory, in accordance with an illustrative embodiment. Entity comparison 2600 may be another example of entity comparison 1000 of FIG. 10. However, entity comparison 2600 is described with respect to the ergonomic analysis illustrative embodiments described with respect to FIG. 16 through FIG. 25.

One possible implementation of the illustrative embodiments is to use an inexpensive motion sensor to capture the activities of interest and a SQL ("structured query language") database to record them. Then, an associative memory could be used to classify new observations, supplied by the motion sensor, against the pre-recorded observations.

For this implementation, a user would setup a predefined database and insert the training data, captured by the motion sensor. An entity category of the training data would be labeled accordingly, perhaps corresponding to each position's ergonomic assessment. Then this data would be ingested into an associative memory for the purpose of classifying new observations against it, using the selected label as the general classifier.

Once ingested, the system could be used to capture movement data from a motion sensor and perform an entity comparison with the training data to see if the movement data resembles any of the pre-recorded ergonomic movements. The result category of the entity comparison would be set to the label previously identified. As a result, the new observation would adopt the label of the movement which it most identifies with. This process is shown in FIG. 26 with respect to attaching the label "overhead" 2602 to common attributes 2604, which are attributes in common with both the observed data and the pre-recorded data which is associated with an "overhead" position.

Typically, the results of an entity comparison are an ordered list of entities that are "like" or "similar to" the original or sought entity. An associative memory collects all the matching attributes among these entities to formulate the list. The order of that list depends on the significance of the matching attributes. Additionally, the ranking of members of the list correlates to the number of attributes found.

The illustrative embodiments described with respect to FIG. 16 through FIG. 25 may be used by individuals, companies, governments, or other organizations that are interested in collecting ergonomic information with respect to how employees are performing their daily tasks. The illustrative embodiments may provide an efficient way to perform an ergonomic analysis in areas where such ergonomic analysis might be difficult. In particular, the illustrative embodiments may benefit any business which manufactures products in factory-like settings. The illustrative embodiments may bring the ergonomic analysis typically performed in office building into the factories.

Furthermore, the illustrative embodiments may be used as an input device for an ergonomic analysis tool. As a result, manufacturers of these tools could use this technology to create a better product. The illustrative embodiments also may save costs and improve the health and well-being of employees by reducing or eliminating undesirable ergonomic behaviors and/or environments.

For example, the illustrative embodiments may provide a cost efficient way of limiting undesirable ergonomic behaviors or environments, representing cost avoidance. The illustrative embodiments may be used to evaluate safety goals, representing cost savings.

The illustrative embodiments may be used within factories to benchmark safety goals and showcase examples of desirable versus undesirable postures, representing cost avoidance. The illustrative embodiments may be used to limit or prevent the frequency of repetitive motion injuries, representing cost avoidance.

The illustrative embodiments may be used to evaluate ergonomic factors in areas where such factors are difficult to diagnose, such as paint hangers, factory settings, and others. The illustrative embodiments may be incorporated with other autonomous products.

Figure 27:
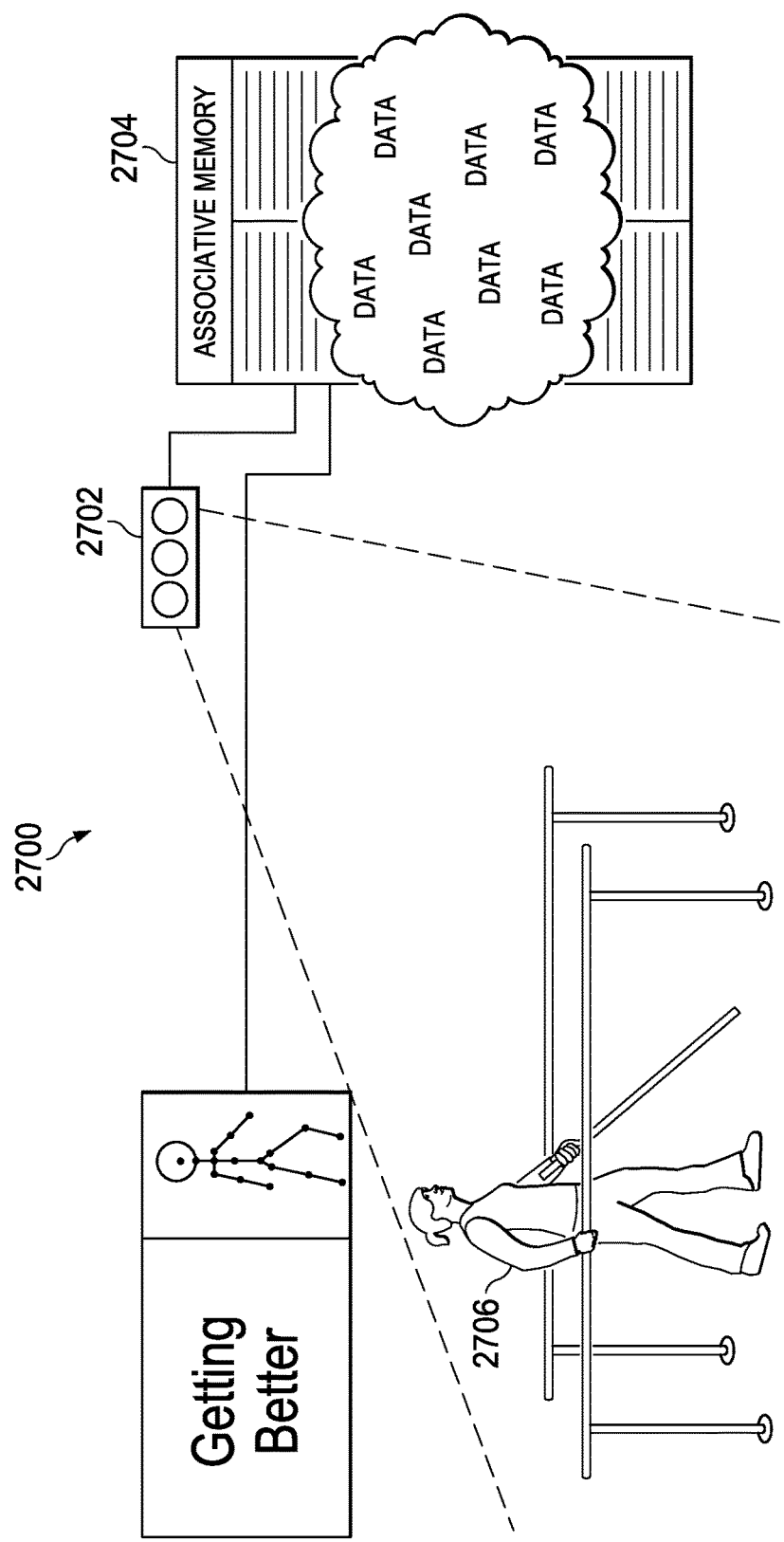
FIG. 27 illustrates a summary procedure for aiding physical therapy using a motion sensing input device, in accordance with an illustrative embodiment.

FIG. 27 illustrates a summary procedure for aiding physical therapy using a motion sensing input device, in accordance with an illustrative embodiment. Motion capture system 2700 may be similar to motion capture system 2300 of FIG. 23, but used in the context of improving physical therapy. As used herein the term "physical therapy" is defined as the treatment of disease, injury, or deformity by physical methods such as massage, heat treatment, and exercise rather than by drugs or surgery.

The purpose of the illustrative embodiments described with respect to FIG. 27 through FIG. 32 and FIG. 35 is to provide feedback to an individual during physical therapy, in hopes of improving their recovery. To accomplish this purpose, the illustrative embodiments evaluate movements, typically gathered by a motion sensor camera, by using an associative memory. The movement data is tested by an associative memory classification to see if the movement data matches any pre-recorded movements. A match occurs only when the incoming data's attributes equal the attributes of the pre-recorded movements. The number of matches strengthens the result. In a different illustrative embodiment, a match may occur when the incoming data's attributes are sufficiently close to the attributes of the pre-recorded movements.

The illustrative embodiments may use motion sensor input device 2702 and associative memory 2704 to train associative memory 2704 with the correct movements needed to improve mobility in patient 2706. Then, during physical therapy, the motion sensor input device 2702 collects the movements of patient 2706. Then, associative memory 2704 classifies the movements of patient 2706 based on the training of the associative memory in order to provide real-time feedback. In this manner, patient 2706 may be informed whether he or she is performing the instructed physical therapy correctly or incorrectly. Accordingly, the illustrative embodiments may be used to improve the recovery time of patient 2706.

Stated differently, a purpose of the illustrative embodiments is to help facilitate the process of physical therapy for patients recovering from surgery, injury, or a variety of medical conditions. A common component of physical therapy is to repetitively move the injured body part in a correct and consistent fashion, so its mobility and strength can be improved. The tasks assigned during physical therapy can be very mundane and frustrating for the patient. The tasks may involve working stiff or injured muscles and joints repetitively. As a result, the tasks may not be performed correctly, which in turn may result in delayed recovery time.

Furthermore, physical therapy can be extremely frustrating for children. Unlike adults, children may not understand the long-term benefits of such therapies, and as a result, may not participate as sincerely as they should. The illustrative embodiments also address the motivational aspect of physical therapy by providing feedback to a patient. Thus, the patient may immediately feel the reward that the movement is being performed correctly. Some patients may wish receive positive feedback from the illustrative embodiments. Thus, the illustrative embodiments not only physically help patient 2706 perform the movements correctly, and thereby improve the effectiveness of physical therapy, but also motivate the patient to perform difficult physical therapy.

Currently, tools designed for physical therapy are limited. Most tools aid in the therapy itself, rather than focusing on patient's participation. For example, physical apparatuses exist which can help patients complete a range of motion or assist them with mobility. However, current apparatuses do not provide instant or accurate feedback or encouragement. For that, patients typically have to rely on an onsite specialist, therapist, or physician. Furthermore, tools used in physical therapy are usually cumbersome, costly, and not always effective.

Returning to FIG. 27, motion sensor input device 2702 may be an apparatus used to detect the change in position of an object relative to its surroundings or the change in the surroundings relative to an object. Motion sensor input device 2702 may be any of the motion sensors described above with respect to FIG. 1 through FIG. 26.

The illustrative embodiments may use motion sensor input device 2702 coupled with associative memory 2704 to aid with physical therapy. Initially an individual may train the system by demonstrating a progression of a particular movement, such as bending one's knees. Motion sensor input device 2702 captures the movement in its entirety. The data representing this movement is provided to associative memory 2704 as training data. Then, using this training data as a foundation, associative memory 2704 classifies the movements of patient 2706. The newly measured movements will correlate with one of the pre-recorded movements within the trained progression. The results of the classification will tell the patient how well he or she is doing with regards to completing that movement correctly.

In an illustrative embodiment, associative memory 2704 may be trained with a range of motions, for a particular type of physical therapy. Each of the motions within the range may be provided with a label indicating the desirability of the motion. For example, for physical therapy of the knee, ten motions could be trained, each with labels from "least favorable" to "most favorable", though other terms may be used. The "least favorable" motion may represent a low range of motion whereas the "most favorable" motion may represent a full range of motion for a normal knee. Associative memory may classify an observed movement by patient 2706 against any of these trained movements.

Associative memory 2704 or an external ergonomic tool may then output the degree of motion that has been performed by patient 2706. Alternatively or in addition, associative memory 2704 or an external ergonomic tool may output whether the motion being performed by patient 2706 represents an improvement or a regression with respect to earlier knee motions performed by the patient. For example, the output could be "getting better" or "needs improvement" or "try again", or any other desired feedback for patient 2706. For diagnostic purposes, a trained physical therapist could receive information comparing the performance of patient 2706 relative to other patients or to study data, or could compare the rate of improvement of patient 2706 in a similar manner. These examples do not necessarily limit the claimed invention, as many other examples and variations exist.

One of several novel aspects of the illustrative embodiments is that the associative memory uses memories of a movement's progression to train itself. Then, when evaluating "live" movements, the associative memory compares those movements with the trained movements in order to properly identify how much the patient has improved.

Another of several novel aspects of the illustrative embodiments is that illustrative embodiments may operate in a non-obtrusive fashion, being invisible to the participant being observed. Preferably patient 2706 knows that his or her movements are being recorded, but because the process is non-obtrusive and non-invasive, patient comfort may be increased.

Another of several novel aspects of the illustrative embodiments is that illustrative embodiments may use inexpensive hardware and centralized software. The illustrative embodiments may also be used within existing physical therapy tools and techniques.

Another of several novel aspects of the illustrative embodiments is that illustrative embodiments are extremely flexible. The illustrative embodiments may be trained to recognize many different movements with concerns to physical therapy.

Another of several novel aspects of the illustrative embodiments is that illustrative embodiments may be updated, changed or improved as desired. Thus, the illustrative embodiments may replace older and more-cumbersome techniques used to inform or update patients.

Another of several novel aspects of the illustrative embodiments is that illustrative embodiments may not necessarily require an onsite expert, therapist, or physician. In addition, the illustrative embodiments may be used with respect to multiple patients simultaneously. Thus, the illustrative embodiments may reduce costs. Likewise, the illustrative embodiments may be independent and subject matter independent with respects to physical therapy. Thus, the illustrative embodiments may be universally deployable.

The illustrative embodiments are not limited to a particular type of physical therapy. The illustrative embodiments may also be carried by a person in order to give continual feedback to that person with respect to movements that may be difficult to that person, such as walking or running. The illustrative embodiments may also be used for sports-related activities, such as assisting a baseball pitcher to correctly throw a baseball. Thus, the illustrative embodiments may be used to aid healthy individuals perform a certain activity better, as well as to help patients improve their health via physical therapy. Likewise, the illustrative embodiments may be used to help train physical therapists perform physical therapy correctly. The illustrative embodiments are not limited by the aids or devices used with physical therapy.

Figure 28:
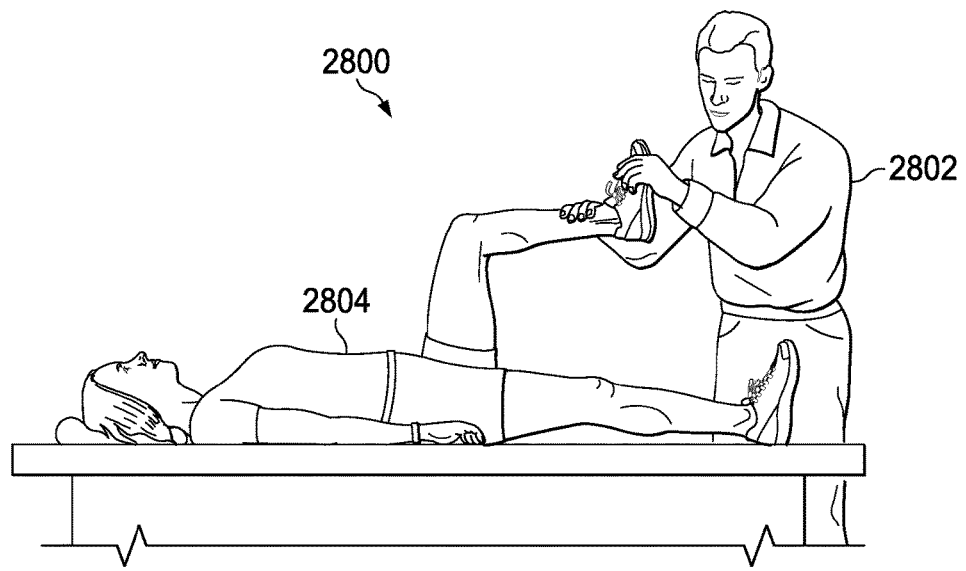
FIG. 28 illustrates an example of a form of physical therapy, in accordance with an illustrative embodiment.

FIG. 28 illustrates an example of a form of physical therapy, in accordance with an illustrative embodiment. Physical therapy 2800 may be, for example, the physical therapy described with respect to FIG. 27.

As described above, physical therapy is the treatment of an injury or paralysis by using physical methods rather than using drugs or surgery. The goal of the therapy is to improve mobility and/or strength, and restore the afflicted area's functionality.

Physical therapy 2800 may be a repetitive process one endures to correct a mobility or strength problem. This process can take days, weeks, or even months or longer to complete and may involve the help of another individual. For example, physical therapist 2802 may assist patient 2804 to perform the required movements.

A fundamental aspect of physical therapy is patient participation. If the patient does not participate in the process, the beneficial value of physical therapy may be diminished or even eliminated. As a result, the patient should be involved in the therapy as much as possible. A common technique is to set goals for the patient. It is recommended a patient identify his or her goals during the initial examination and then adhere to them as the therapy progresses. The illustrative embodiments can assist with this process, while decreasing the time physical therapist 2802 must spend with patient 2804.

Figure 29:
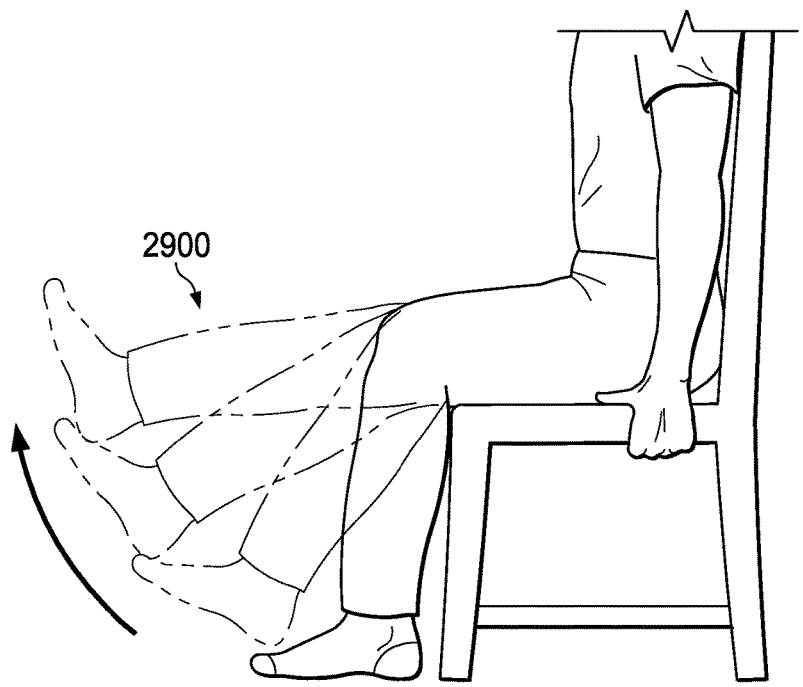
FIG. 29 illustrates an example of a movement in its entirety, in accordance with an illustrative embodiment.

FIG. 29 illustrates an example of a movement in its entirety, in accordance with an illustrative embodiment. Movement 2900 may be conducted as part of physical therapy, such as physical therapy 2800 of FIG. 28.

The associative memory may be trained by an individual, such as a trained physical therapist rather than a patient. The physical therapist can demonstrate the desirable correct movement for a particular proscribed therapy. Each demonstration should show the full range of motion used to complete each movement in its entirety.

Figure 30:
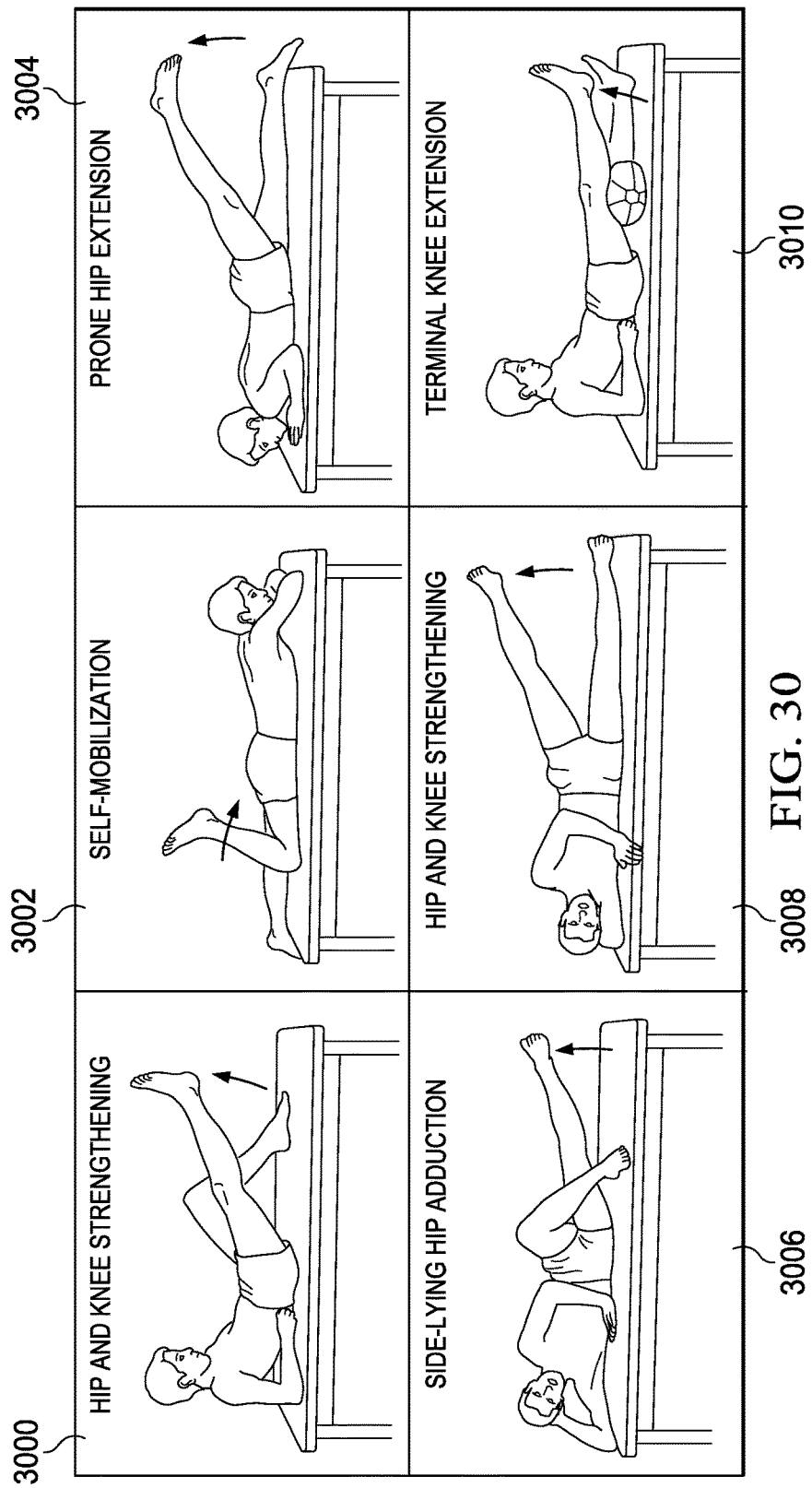
FIG. 30 illustrates examples of physical therapy involving the knees, in accordance with an illustrative embodiment.

FIG. 30 illustrates examples of physical therapy involving the knees, in accordance with an illustrative embodiment. Each of movement 3000, movement 3002, movement 3004, movement 3006, movement 3008, and movement 3010 may be a movement, such as movement 2900 of FIG. 29, for physical therapy, such as physical therapy 2800 of FIG. 28.

The illustrative embodiments can handle multiple movements, as long as each movement is labeled accordingly. For example, if a patient injured their knees, an individual could demonstrate a series of movements, all which involve bending their knees, as outlined in FIG. 30. Each movement outlined in FIG. 6 could be labeled as follows: movement 3000 could be labeled Hip and Knee Strengthening; movement 3002 could be labeled Self-Mobilization; movement 3004 could be labeled Prone Hip Extension; movement 3006 could be labeled Side-Lying Hip Adduction; movement 3008 could be labeled Hip and Knee Strengthening; and movement 3010 could be labeled Terminal Knee Extension.

Typically each movement may recorded from the input sensor into a storage device. Then, each movement is ingested into an associative memory to form the foundation of the training. As part of this process, each movement may be associated with a label that identifies the movement with a particular therapy, such as "Hip and Knee Strengthening", "Self-Mobilization", as described above.

The illustrative embodiments may be varied. For example, different movements may be trained and later classified. More or fewer movements may be trained and later classified. Sequences of different moves may be trained and later classified. Other body parts may be trained and later classified as described above, with any of the above variations. Likewise, robotic movements or sequences of movements may be trained and later classified. Thus, the illustrative embodiments are not necessarily limited to the specific examples described with respect to FIG. 28 through FIG. 30.

Figure 31:
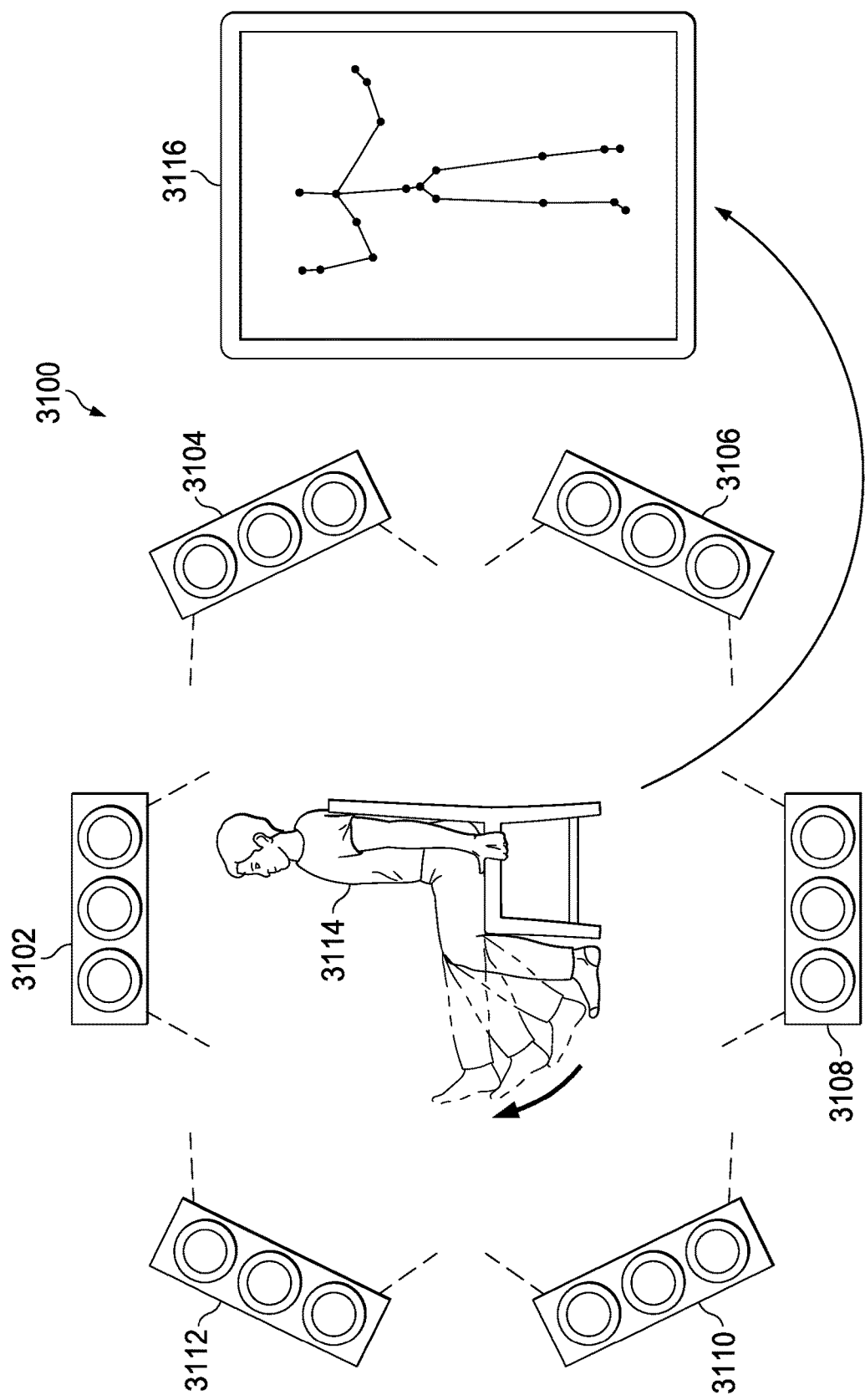
FIG. 31 illustrates an example of a movement during physical therapy as captured by a motion sensor, in accordance with an illustrative embodiment.

FIG. 31 illustrates an example of a movement during physical therapy as captured by a motion sensor, in accordance with an illustrative embodiment. FIG. 31 may be a variation of motion capture system 2300 shown in FIG. 23, modified for use in physical therapy.

Once training of the associative memory is complete, as described above with respect to FIG. 30, the associative memory or physical therapy evaluation tool is ready for use. In an illustrative embodiment, first setup one or more motion sensors in area of intended use 3100. The one or more motion sensors could be, for example, motion sensor 3102, motion sensor 3104, motion sensor 3106, motion sensor 3108, motion sensor 3110, or motion sensor 3112. Then, use one or more of these sensors to capture the movements of individual 3114. The captured motions and/or positions may be displayed on a computer system, or otherwise recorded, as shown at display 3116. At this point, the associative memory evaluates the observation captured by the sensors to determine if the observation is, in fact, a correctly performed physical therapy movement.

Optionally, an alert may be generated to alert the user or some other person, or possibly software, if the observation represents a correct or desired movement or position, or represents undesirable movement or position. This alert could take many forms, such as but not limited to an audio alert, a visual alert, or a written report.

Each new observation provides the associative memory with a new set coordinates, typically located at points of articulation, such as the points of articulation shown at display 3116. This information is transformed into a word-like verbiage and used to build the foundation of subsequent classification calls. The coordinates themselves can also be manipulated to give the classification call more relevance. For example, locations, distances and directions could be calculated from these coordinates to provide greater detail.

Using the manipulated coordinates, the associative memory may construct a classification call, such as for example associative memory classification call 2400 of FIG. 24. The syntax of this call can vary depending on the underlying rules of the particular classification system used. The classification call contains attributes collected from the information described above.

The results of this call may determine which of the training sets the new observation most resembles. Using this result, the associative memory can conclude what position was captured. The associative memory can then relay that determination back to the user, such as the patient, the physical therapist, both the patient and the physical therapist, or perhaps other persons. If a physical therapy evaluation tool is available, the results may be fed into such a tool.

Figure 32:
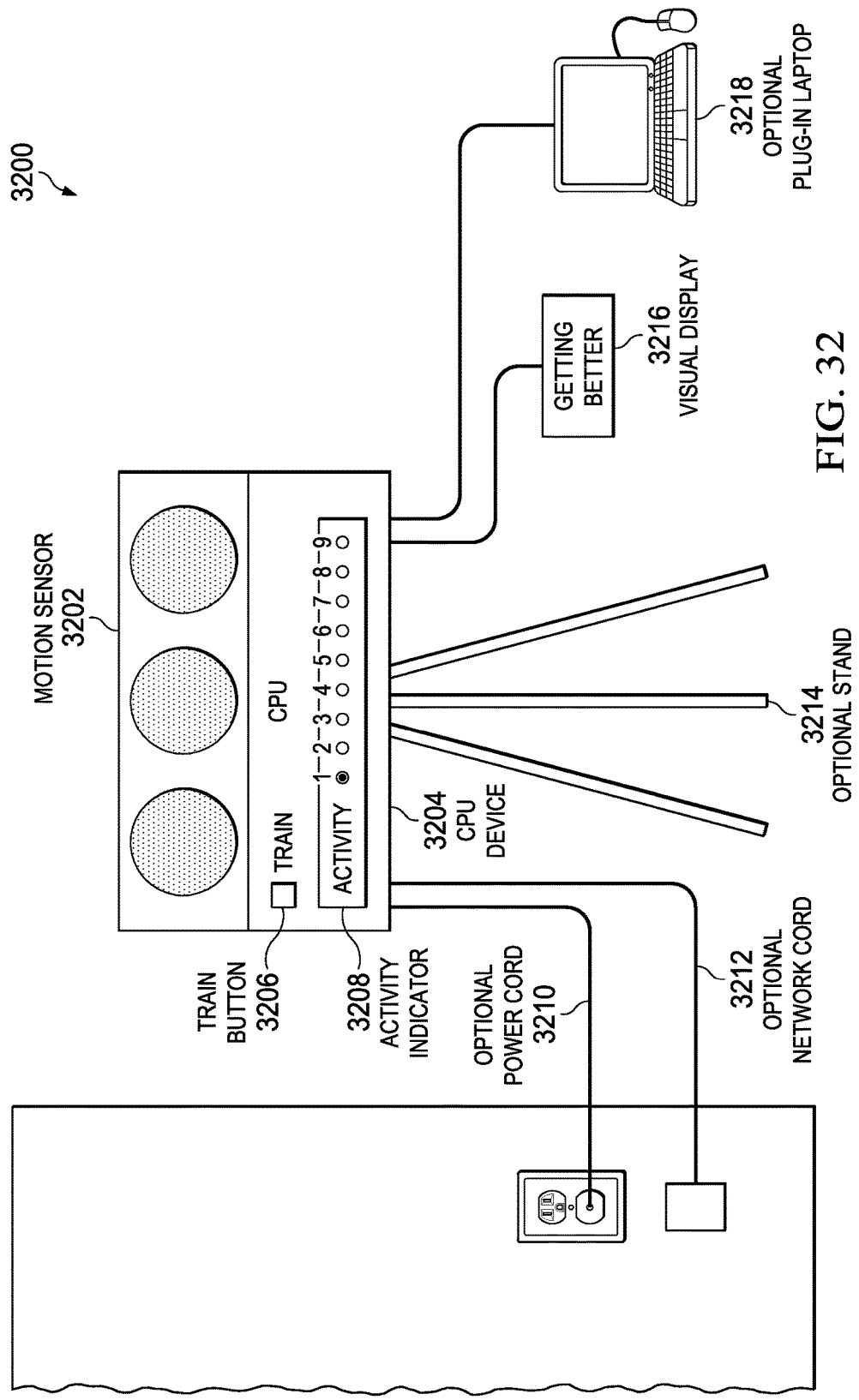
FIG. 32 illustrates an example of one physical embodiment of a motion capture system for use in aiding physical therapy, in accordance with an illustrative embodiment.

FIG. 32 illustrates an example of one physical embodiment of a motion capture system for use in aiding physical therapy, in accordance with an illustrative embodiment. Physical therapy evaluation system 3200 may be a variation of ergonomic evaluation system 2500 of FIG. 25.

One possible physical embodiment of physical therapy evaluation system 3200 is illustrated in FIG. 32. As shown, physical therapy evaluation system 3200 could use either a motion sensor camera or some other device as motion sensor 3202 to connect to CPU device 3204, which may contain the associative memory. "CPU" stands for "central processing unit", but may also refer to a computer generally. CPU device 3204 may have train button 3206 used to switch to "training" mode to train the associative memory. Activity indicator 3208 may allow the user to select from a selection of pre-recorded therapeutic movements.

As described with respect to the ergonomic evaluation system described with respect to FIG. 20, motion sensor 3202 need not be limited to a single device or necessarily use all available sensors for a given application. For example, stored or taken data may be limited to only certain sensors of a sensor suit, such as when motions of only a specific part or parts of a person's body are to be captured. Likewise, a camera or other remote sensor could record data only for a certain part or parts of a person's body. Motion sensor 3202 may be combination of a sensor suit, a camera, and/or some other motion sensor in the illustrative embodiments.

Physical therapy evaluation system 3200 could include optional power cord 3210 or a battery. Physical therapy evaluation system 3200 could also include optional network cord 3212 or a wireless device connecting it to a network. In this manner, a remote associative memory, database, or any other system credentials could be accessed. However, it is possible to place all the desired software for operation of physical therapy evaluation system 3200 within CPU device 3204 itself.

Physical therapy evaluation system 3200 could include optional stand 3214 or be placed somewhere secure. Visual display 3216 may be connected to motion sensor 3202 and/or CPU device 3204. Visual display 3216 may be used to display information regarding the physical therapy, such as but not limited to the progress of the patient's recovery. Finally, optional plug-in laptop 3218 could be used to help configure, update, or optimize the associative memory or the data it stores. Optional plug-in laptop 3218 could be CPU device 3204, or be in addition to CPU device 3204. Optional plug-in laptop 3218 could be replaced by a desktop, a tablet computer, or some other computing device.

One possible implementation of physical therapy evaluation system 3200 may use an inexpensive motion sensor to capture the activities of interest and a SQL database to record them. Then an associative memory could be used to classify new observations, supplied by the motion sensor, against the pre-recorded ones.

For this implementation, a user would setup a predefined database and insert the training data, captured by the motion sensor. An entity category of the training data would have to be labeled accordingly, perhaps corresponding to each movement's therapeutic position. Then, using an associative memory, a user would cause this data to be ingested into the associative memory for the purpose of classifying new observations against it, using the selected label as the general classifier.

Once ingested, physical therapy evaluation system 3200 could be used to capture movement data from a motion sensor and perform an entity comparison with the training data to see if it resembles any of the pre-recorded movements. The result category of the entity comparison would be set to the label previously identified. As a result, the new observation would adopt the label of the movement with which it most identifies.

Typically, the results of an entity comparison are an ordered list of entities that are "like" or "similar to" the original or sought entity. An associative memory collects all the matching attributes among these entities to formulate the list. The order of that list depends on the significance of the matching attributes. Additionally, its ranking correlates to the number of attributes found.

For an entity comparison to perform like a classification, the resulting category should be changed to match the classifier. Usually, an entity comparison returns a list of similar entities, such as flights like flight 207 would return flights. However, if it is desired to perform like a classification, the returning type should to be something else; in particular, it should be changed to the classifier.

In any case, the illustrative embodiments with respect to FIG. 27 through FIG. 32 are helpful to hospitals, clinics, and other facilities in which physical therapy takes place. Any institution interested in physical therapy could benefit from this technology. Because the underlying technology is so flexible, the illustrative embodiments could be incorporated into many different areas of the medical field. The illustrative embodiments could also be used by companies, government entities, or other organizations to lower costs by reducing the amount of time a physical therapist must spend with a patient. The illustrative embodiments may improve patient health and reduce recovery times by helping ensure that physical therapy exercises are performed correctly.

Furthermore, one of its distinguishing traits of this the illustrative embodiments is the ability to recognize improvements among a range of movements. In other words, the illustrative embodiments may be used to track the improvement of a patient over time. Typically, this kind of analysis would involve an expert.

Figure 33:
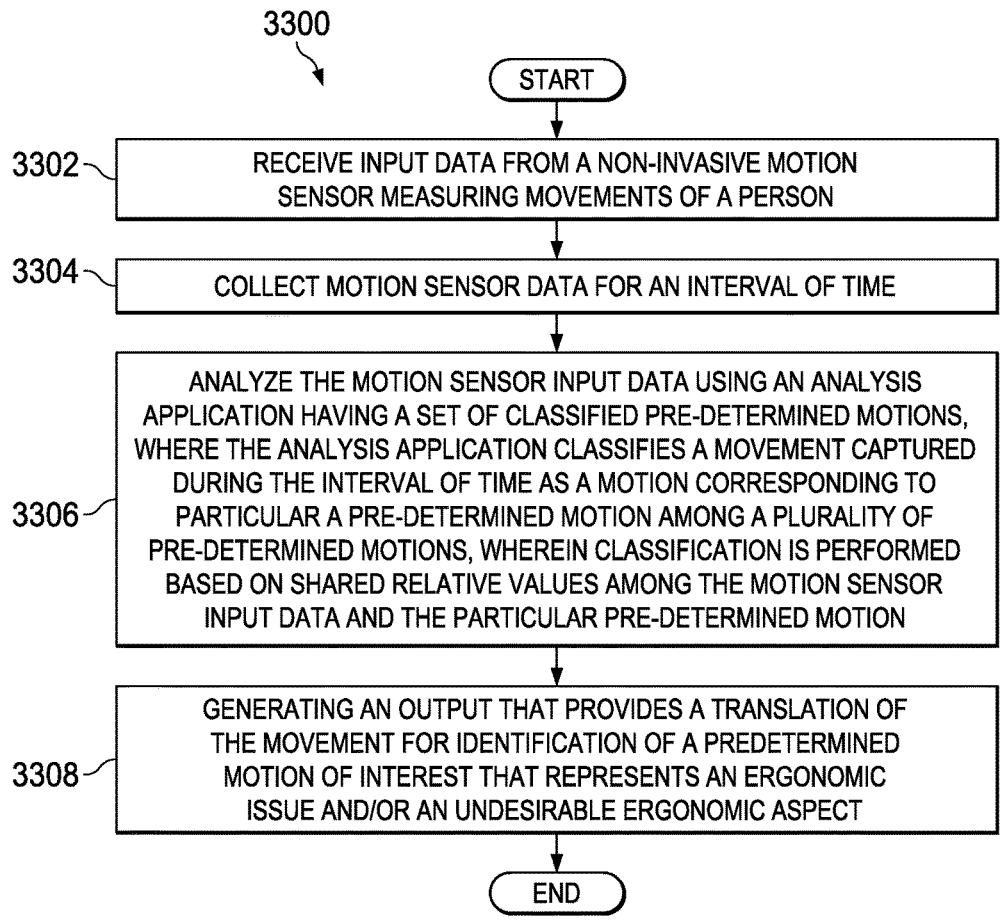
FIG. 33 is a flowchart of a method for identifying a motion of interest of an individual, in accordance with an illustrative embodiment.

FIG. 33 is a flowchart of a method for identifying a motion of interest of an individual, in accordance with an illustrative embodiment. Method 3300 may be a variation of the ergonomic evaluation methods described with respect to FIG. 16 through FIG. 26.

Method 3300 may be a method for identifying a motion of interest of an individual. Method 3300 may include receiving input data from a non-invasive motion sensor measuring movements of a person (operation 3302). The input data may be received by an associative memory, or possibly some other device. Thus, method 3300 may include collecting motion sensor data for an interval of time (operation 3304). This motion sensor data may be collected by the associative memory, or by some other storage and then provided to an associative memory.

Next, method 3300 includes analyzing the motion sensor input data using an analysis application having a set of classified pre-determined motions, where the analysis application classifies a movement captured during the interval of time as a motion corresponding to particular a pre-determined motion among a plurality of pre-determined motions, wherein classification is performed based on shared relative values among the motion sensor input data and the particular pre-determined motion (operation 3306). Operation 3306 is typically performed by an associative memory.

Method 3300 may further include generating an output that provides a translation of the movement for identification of a predetermined motion of interest that represents an ergonomic issue and/or an undesirable ergonomic aspect (operation 3308). This operation may be performed by an associative memory. In an illustrative embodiment, the process may terminate thereafter.

However, method 3300 may be further varied. For example, method 3300 may further include generating an alert output when the predetermined motion of interest exceeds a predetermined threshold. In another illustrative embodiment, method 3300 may further include notifying a user that the individual's movements represent an ergonomic issue. In an illustrative embodiment, the user is the individual.

In an illustrative embodiment, the analysis application comprises an associative memory comprising a plurality of data and a plurality of associations among the plurality of data. In this case, the plurality of data is collected into associated groups and the associative memory is configured to be queried based on at least indirect relationships among the plurality of data.

In an illustrative embodiment, method 3300 may include other operations. For example, in an illustrative embodiment, method 3300 may further include the motion as a second pre-determined motion in the plurality of pre-determined motions. Then, method 3300 includes receiving second input data from the non-invasive motion sensor. Then, method 3300 includes collecting second motion sensor data for a second interval of time. Then, method 3300 includes analyzing the second motion sensor input data using the analysis application. In this case, the analysis application classifies a second movement captured during the second interval of time as a second motion corresponding to a second pre-determined motion among the plurality of pre-determined motions. Classification may be performed based on shared relative values among the second motion sensor input data and the second pre-determined motion. Finally, in this particular illustrative embodiment, method 3300 may include generating a second output that provides a second translation of the movement for identification of a second predetermined motion of interest that represents a second ergonomic issue.

In still other illustrative embodiments, method 3300 may include determining a level of undesirable ergonomic aspects of the movement. Similarly, method 3300 may include, responsive to the level of undesirable ergonomic aspects exceeding a threshold, notifying a user that the level has exceeded a threshold.

In an illustrative embodiment, method 3300 may include providing the output to an ergonomic tool. In this case, method 3300 may include using the ergonomic tool to assess an overall level of ergonomic issues of the person. Thus, the illustrative embodiments may evaluate whether a person is performing physical actions within a range of motions considered to be ergonomically desirable, or a range of motions considered to be ergonomically undesirable. The illustrative embodiments may also indicate to a person whether the person is improving or worsening in their motions with respect to the desirability or undesirability of those motions, from an ergonomic perspective.

In a still different illustrative embodiment, method 3300 may include re-training the analysis application to include the motion in the plurality of pre-determined motions. In an illustrative embodiment, the shared relative values comprise qualitative descriptions of movements of the individual, as opposed to quantitative measurements of body part positions of the individual.

Other variations are possible. Thus, the above examples do not necessarily limit the claimed inventions.

Figure 34:
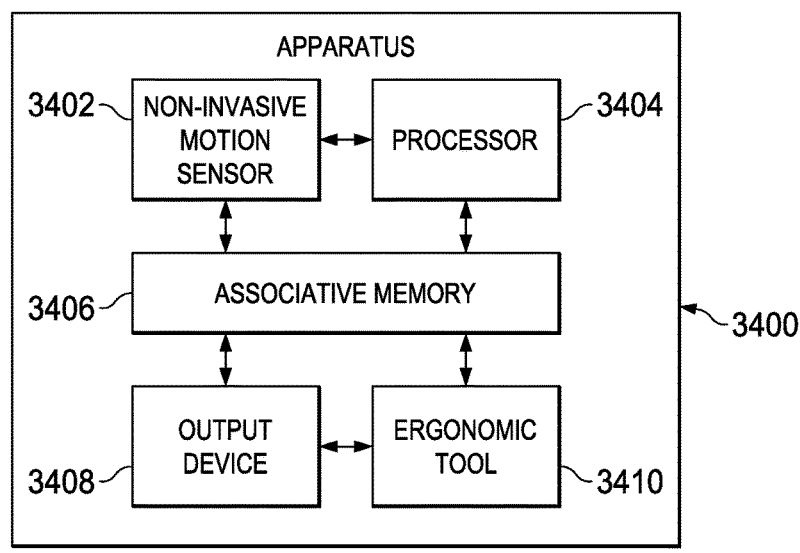
FIG. 34 is a block diagram of an apparatus for identifying a motion of interest of an individual, in accordance with an illustrative embodiment.

FIG. 34 is a block diagram of an apparatus for identifying a motion of interest of an individual, in accordance with an illustrative embodiment. Apparatus 3400 may be a variation of the apparatuses described with respect to FIG. 16 through FIG. 26.

Apparatus 3400 may be an apparatus for identifying a motion of interest of an individual. Apparatus 3400 may include non-invasive motion sensor 3402. Apparatus 3400 may also include processor 3404 in communication with non-invasive motion sensor 3402. Processor 3404 may be configured to collect motion sensor data of a person for an interval of time.

Apparatus 3400 may also include associative memory 3406. Associative memory 3406 may be configured to analyze the motion sensor input data. Associative memory 3406 may also include storage for a set of classified pre-determined motions. Associative memory 3406 may be configured to classify a movement captured during the interval of time as a motion corresponding to a particular pre-determined motion among a plurality of pre-determined motions. Classification may be performed by comparing shared relative values among the motion sensor input data and the particular pre-determined motion.

Apparatus 3400 may also include output device 3408. Output device 3408 may be configured to generate an output that provides a translation of the movement for identification of a predetermined motion of interest that represents an ergonomic issue. This output device 3408 may be a physical alert device. However, the physical alert device may be separate from output device 3408. The physical alert device may produce audio, visual, and/or other stimuli to alert a user. In an example, the physical alert device may trigger when the movement exceeds a pre-determined threshold.

In a different illustrative embodiment, apparatus 3400 may also include ergonomic tool 3410. Ergonomic tool 3410 may be configured to ergonomically evaluate movements of the person. Ergonomic tool 3410 may receive as input the output of output device 3408, but may also receive such input directly from associative memory 3406.

Apparatus 3400 may be further varied. For example, output device 3408 may be configured to notify, responsive to the ergonomic aspect exceeding a threshold, a user that the level of the ergonomic aspect has exceeded a threshold.

As used herein, the term "ergonomic aspect" refers to a range of a particular motion. For example, a threshold for an ergonomic aspect may be a range of motion beyond which the motion as a whole is considered undesirable. In another example, a threshold for an ergonomic aspect may be a range of motion within which the motion is considered acceptable or desirable.

For example, usually when a person lifts an object using his or her legs, the person still bends at the hip to some degree. In another example, if the person's knees were locked and the person bends over to lift the object using his or her back, then the degree of bending, or the range of motion of back movement (ergonomic aspect), may be considered undesirable from an ergonomic perspective. However, if the person's back had bent within a particular acceptable range within a threshold while lifting the object, then the movement (ergonomic aspect) could be considered ergonomically acceptable or desirable.

In another illustrative embodiment, associative memory 3406 may be configured to compare the shared relative values by comparing shared qualitative descriptions of movements of the individual to qualitative descriptions of the pre-determined motion, as opposed to comparing quantitative measurements of body part positions of the individual to quantitative pre-determined body part positions in the pre-determined motion.

Additional variations are also possible. Thus, the claimed inventions are not necessarily limited by the examples described above.

Figure 35:
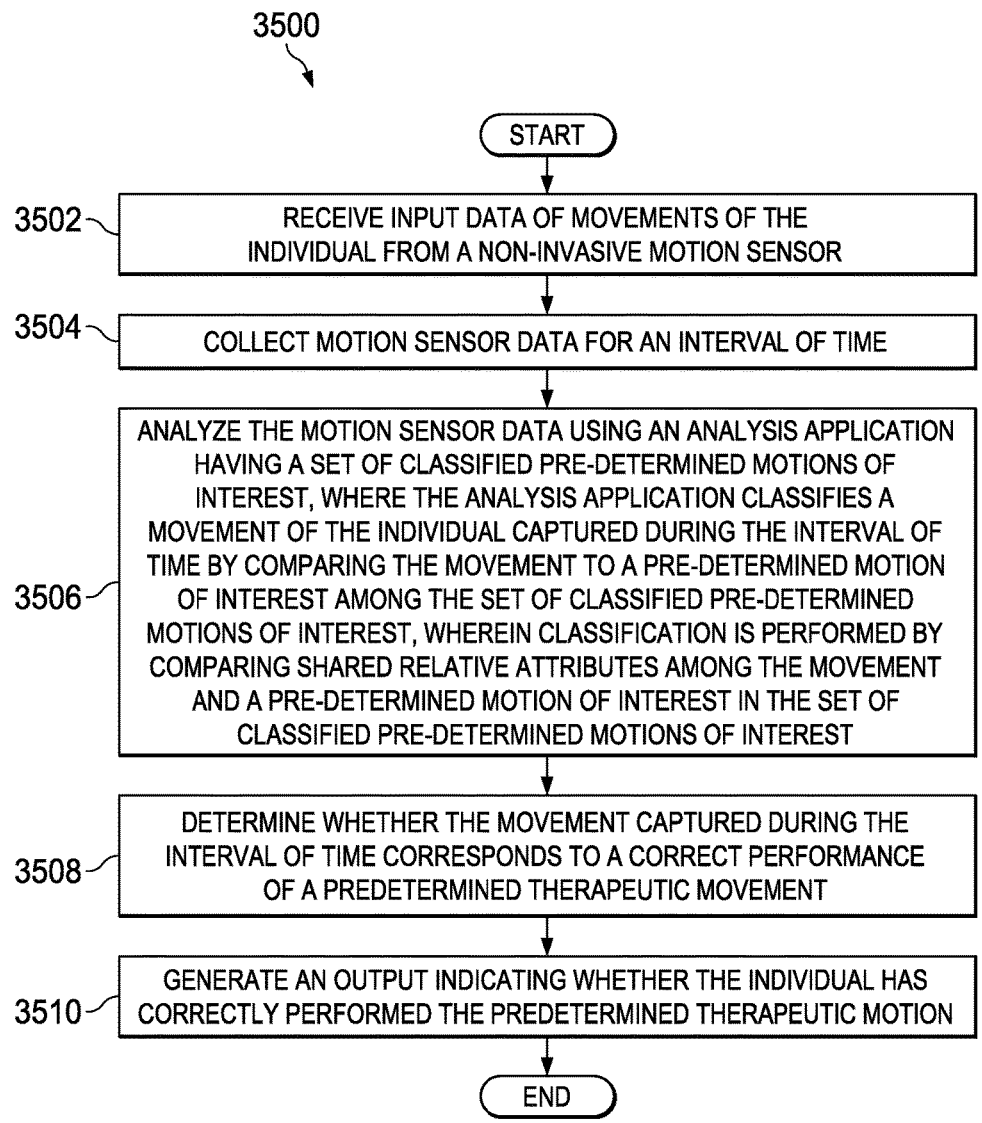
FIG. 35 is a flowchart of a method for assisting physical therapy for a motion of interest of an individual, in accordance with an illustrative embodiment.

FIG. 35 is a flowchart of a method for assisting physical therapy for a motion of interest of an individual, in accordance with an illustrative embodiment. Method 3500 is a variation of the physical therapy improvement methods described with respect to FIG. 27 through FIG. 32.

Thus, method 3500 may be characterized as a method for assisting physical therapy for a motion of interest of an individual. Method 3500 may include receiving input data of movements of the individual from a non-invasive motion sensor (operation 3502). An associative memory may receive this input data, or it may be received by some other device and later transferred to an associative memory.

Method 3500 may also include collecting motion sensor data for an interval of time (operation 3504). This operation may be performed by the associative memory, or may be performed by some other device and later transferred to an associative memory.

Method 3500 may also include analyzing the motion sensor data using an analysis application having a set of classified pre-determined motions of interest, where the analysis application classifies a movement of the individual captured during the interval of time by comparing the movement to a pre-determined motion of interest among the set of classified pre-determined motions of interest, wherein classification is performed by comparing shared relative attributes among the movement and a pre-determined motion of interest in the set of classified pre-determined motions of interest (operation 3506). An associative memory may perform this operation.

Method 3500 may also include determining whether the movement captured during the interval of time corresponds to a correct performance of a predetermined therapeutic movement (operation 3508). Again, an associative memory may perform this operation.

Method 3500 may also include generating an output indicating whether the individual has correctly performed the predetermined therapeutic motion (operation 3510). Again, an associative memory may perform this operation. In an illustrative embodiment, the process may terminate thereafter.

Method 3500 may be further varied. For example, method 3500 may also include alerting the individual whether the individual has correctly performed the predetermined therapeutic motion. This alert may be performed by an audio signal, a visual signal, some other signal, or a combination of signals. The alert may be provided to a physical therapist or some other use. The alert may be recorded or provided to a tool for evaluating physical therapy. In another illustrative embodiment, results of the classification tell the individual how well he or she is doing with regards to completing the motion of interest correctly. In another illustrative embodiment, results of the classification may tell the individual whether the motion of interest represents a therapeutic improvement relative to one or more prior movements of the individual. Likewise, results of the classification can also indicate to a therapeutic evaluator whether the motion of interest represents a therapeutic improvement that is being performed correctly by the individual. Thus, the claimed inventions are not necessarily limited by the illustrative embodiments described above.

The different illustrative embodiments can take the form of an entirely hardware embodiment, an entirely software embodiment, or an embodiment containing both hardware and software elements. Some embodiments are implemented in software, which includes but is not limited to forms such as, for example, firmware, resident software, and microcode.

Furthermore, the different embodiments can take the form of a computer program product accessible from a computer usable or computer readable medium providing program code for use by or in connection with a computer or any device or system that executes instructions. For the purposes of this disclosure, a computer usable or computer readable medium can generally be any tangible apparatus that can contain, store, communicate, propagate, or transport the program for use by or in connection with the instruction execution system, apparatus, or device.

The computer usable or computer readable medium can be, for example, without limitation an electronic, magnetic, optical, electromagnetic, infrared, or semiconductor system, or a propagation medium. Non-limiting examples of a computer readable medium include a semiconductor or solid state memory, magnetic tape, a removable computer diskette, a random access memory (RAM), a read-only memory (ROM), a rigid magnetic disk, and an optical disk. Optical disks may include compact disk-read only memory (CD-ROM), compact disk-read/write (CD-R/W), and DVD.

Further, a computer usable or computer readable medium may contain or store a computer readable or computer usable program code such that when the computer readable or computer usable program code is executed on a computer, the execution of this computer readable or computer usable program code causes the computer to transmit another computer readable or computer usable program code over a communications link. This communications link may use a medium that is, for example without limitation, physical or wireless.

A data processing system suitable for storing and/or executing computer readable or computer usable program code will include one or more processors coupled directly or indirectly to memory elements through a communications fabric, such as a system bus. The memory elements may include local memory employed during actual execution of the program code, bulk storage, and cache memories which provide temporary storage of at least some computer readable or computer usable program code to reduce the number of times code may be retrieved from bulk storage during execution of the code.

Input/output or I/O devices can be coupled to the system either directly or through intervening I/O controllers. These devices may include, for example, without limitation, keyboards, touch screen displays, and pointing devices. Different communications adapters may also be coupled to the system to enable the data processing system to become coupled to other data processing systems or remote printers or storage devices through intervening private or public networks. Non-limiting examples of modems and network adapters are just a few of the currently available types of communications adapters.

The description of the different illustrative embodiments has been presented for purposes of illustration and description, and is not intended to be exhaustive or limited to the embodiments in the form disclosed. Many modifications and variations will be apparent to those of ordinary skill in the art. Further, different illustrative embodiments may provide different features as compared to other illustrative embodiments. The embodiment or embodiments selected are chosen and described in order to best explain the principles of the embodiments, the practical application, and to enable others of ordinary skill in the art to understand the disclosure for various embodiments with various modifications as are suited to the particular use contemplated.

What is claimed is:

1. A method for improving ergonomic movements of a person operating factory equipment at a factory, comprising:
   receiving input data from a non-invasive motion sensor measuring movements of the person while the person operates the factory equipment;
   collecting, using the non-invasive motion sensor, motion sensor data of the movements of the person for an interval of time;
   analyzing the motion sensor data using an analysis application having a set of classified pre-determined motions, where the analysis application classifies a movement captured during the interval of time as a motion corresponding to particular a pre-determined motion among a plurality of pre-determined motions, wherein classification is performed based on shared relative values among the motion sensor data and the particular pre-determined motion, wherein a classified motion is formed, and wherein the shared relative values comprise qualitative descriptions of the movements of the person as opposed to quantitative measurements of the movements of the person
   comparing the classified motion to a set of pre-determined motions that were pre-determined to be undesirable ergonomic motions in an ergonomic analysis for a factory setting; and
   responsive to the classified motion being among the pre-determined motions that were pre-determined to be undesirable ergonomic motions, monitoring an amount of time for the classified motion, and, using a display to display information to the person and issuing an alert that communicates to the person that the pre-determined motion during the interval of time represents an ergonomically incorrect or undesirable movement for a factory setting.

2. The method of claim 1 further comprising:
   generating an alert output when the classified motion exceeds a predetermined threshold.

3. The method of claim 1 further comprising:
   operating, by the person, the factory equipment.

4. The method of claim 3, wherein, analyzing further comprises:
   converting the motion sensor data into word-like verbiage describing points of articulation of the person, and wherein the shared relative values are additional word-like verbiage describing the points of articulation for the plurality of pre-determined motions, such that analyzing is performed by comparing the word-like verbiage to the additional word-like verbiage.

5. The method of claim 1, wherein the analysis application comprises an associative memory comprising a plurality of data and a plurality of associations among the plurality of data, wherein the plurality of data is collected into associated groups, wherein the associative memory is configured to be queried based on at least indirect relationships among the plurality of data.

6. The method of claim 1 further comprising:
   including the classified motion as a second pre-determined motion in the plurality of pre-determined motions; and
   receiving second input data from the non-invasive motion sensor;
   collecting second motion sensor data for a second interval of time;
   analyzing the second motion motion sensor data using the analysis application, where the analysis application classifies a second movement captured during the second interval of time as a second motion corresponding to a second pre-determined motion among the plurality of pre-determined motions, wherein classification is performed based on shared relative values among the second motion motion sensor data and the second pre-determined motion, wherein a second classified motion is formed;
   comparing the classified motion to a set of pre-determined motions that were pre-determined to be undesirable ergonomic motions in an ergonomic analysis for a factory setting; and
   responsive to the classified motion being among the pre-determined motions, using a display to display information to the person and issuing an alert that communicates to the person that the pre-determined motion represents an ergonomically incorrect or undesirable movement for a factory setting.

7. The method of claim 1 further comprising:
   determining a level of the undesirable ergonomic motion.

8. The method of claim 7 further comprising:
   responsive to the level of the undesirable ergonomic motion exceeding a threshold, notifying a user that the level of the undesirable ergonomic motion has exceeded a threshold.

9. The method of claim 1 further comprising:
   providing an output of the analysis application to an ergonomic tool.

10. The method of claim 9 further comprising:
using the ergonomic tool to assess an overall level of ergonomic issues for the person.

11. The method of claim 1 further comprising:
training the analysis application to include the motion in the plurality of pre-determined motions.

12. An apparatus for identifying a body position of interest of an individual, comprising:
a non-invasive body position sensor;
a processor in communication with the body position sensor, being configured to collect body position sensor data of a person for an interval of time; and
an associative memory configured to analyze the body position sensor data, the associative memory storing a set of classified pre-determined body positions, where the associative memory is configured to classify a movement captured during the interval of time as a body position corresponding to a particular pre-determined body position among a plurality of pre-determined body positions, wherein a classified body position is formed, and wherein the associative memory is further configured to compare the classified body position to a set of pre-determined body positions that were pre-determined to be undesirable ergonomic body positions in an ergonomic analysis for a factory setting, and to monitor an amount of time spent in the classified body position, and wherein the associative memory is further configured, responsive to the classified body position during the interval of time being among the set of pre-determined body positions, to use a display to display information to the person and issue an alert that communicates to the person that the pre-determined body position represents an ergonomically incorrect or undesirable movement for a factory setting, and wherein the associative memory is further configured to compare the classified body position by comparing shared qualitative descriptions of body positions of the individual to qualitative descriptions of the set of pre-determined body positions, as opposed to comparing quantitative measurements of the body positions of the individual to quantitative pre-determined body positions.

13. The apparatus of claim 12 further comprising:
an output device configured to generate an output that provides a translation of the movement for identification of a predetermined body position of interest that represents an undesirable ergonomic movement.

14. The apparatus of claim 13, further comprising:
a physical alert device that triggers when the movement exceeds a pre-determined ergonomic threshold.

15. The apparatus of claim 13 further comprising:
an ergonomic tool configured to ergonomically evaluate movements of the person, wherein the ergonomic tool receives as input the output of the output device.

16. The apparatus of claim 13, wherein the output device is configured to notify, responsive to the undesirable ergonomic movement exceeding a threshold, a user that a level of the undesirable ergonomic movement has exceeded a threshold.

* * * * *

UNITED STATES PATENT AND TRADEMARK OFFICE
CERTIFICATE OF CORRECTION

PATENT NO. : 9,911,031 B2  
APPLICATION NO. : 14/573591  
DATED : March 6, 2018  
INVENTOR(S) : Whelan et al.

Page 1 of 1

It is certified that error appears in the above-identified patent and that said Letters Patent is hereby corrected as shown below:

On the Title Page

Item (57), Abstract, Line 10, correct "to particular a" to read -- to a particular --

In the Specification

Column 2, Line 27, Summary, correct "to particular a" to read -- to a particular --

Column 37, Line 26, Method 3300, correct "to particular a" to read -- to a particular --

Column 41, Line 52, correct "to particular a" to read -- to a particular --

Signed and Sealed this  
Fifteenth Day of January, 2019

Andrei Iancu  
*Director of the United States Patent and Trademark Office*